US009994923B2

(12) United States Patent
Jackson et al.

(10) Patent No.: US 9,994,923 B2
(45) Date of Patent: Jun. 12, 2018

(54) NEUTRALIZING PROPROTEIN CONVERTASE SUBTILISIN KEXIN TYPE 9 (PCSK9) VARIANTS AND USES THEREOF

(75) Inventors: Simon Mark Jackson, San Carlos, CA (US); Derek Evan Piper, Santa Clara, CA (US)

(73) Assignee: Amgen Inc., Thousand Oaks, CA (US)

( * ) Notice: Subject to any disclaimer, the term of this patent is extended or adjusted under 35 U.S.C. 154(b) by 554 days.

(21) Appl. No.: 12/989,404

(22) PCT Filed: Feb. 20, 2009

(86) PCT No.: PCT/US2009/034775
§ 371 (c)(1),
(2), (4) Date: Dec. 16, 2010

(87) PCT Pub. No.: WO2009/131740
PCT Pub. Date: Oct. 29, 2009

(65) Prior Publication Data
US 2011/0117011 A1    May 19, 2011

Related U.S. Application Data

(60) Provisional application No. 61/125,304, filed on Apr. 23, 2008.

(51) Int. Cl.
| | |
|---|---|
| *A61K 51/00* | (2006.01) |
| *A61K 39/395* | (2006.01) |
| *A61K 38/48* | (2006.01) |
| *C12N 9/64* | (2006.01) |
| *A61K 45/06* | (2006.01) |
| *A61K 31/22* | (2006.01) |
| *A61K 31/366* | (2006.01) |
| *A61K 31/40* | (2006.01) |
| *A61K 31/405* | (2006.01) |
| *A61K 31/44* | (2006.01) |
| *A61K 31/47* | (2006.01) |
| *A61K 31/505* | (2006.01) |
| *A61K 38/00* | (2006.01) |

(52) U.S. Cl.
CPC ...... *C12Y 304/21061* (2013.01); *A61K 31/22* (2013.01); *A61K 31/366* (2013.01); *A61K 31/40* (2013.01); *A61K 31/405* (2013.01); *A61K 31/44* (2013.01); *A61K 31/47* (2013.01); *A61K 31/505* (2013.01); *A61K 38/482* (2013.01); *A61K 45/06* (2013.01); *C12N 9/6454* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,300,754 | B2 | 11/2007 | Abi Fadel et al. |
| 2008/0008697 | A1 | 1/2008 | Mintier et al. |

FOREIGN PATENT DOCUMENTS

| | | |
|---|---|---|
| WO | WO 07/128121 | 11/2007 |
| WO | WO 08/105797 | 9/2008 |

OTHER PUBLICATIONS

Attwood (Science 290: 471-473, 2000).*
Skolnick et al. (Trends in Biotech. 18: 34-39, 2000).*
Bingham et al., "Proapoptotic effects of NARC 1 (=PCSK9), the gene encoding a novel serine proteinase", Cytometry Part A, 69A: 1123-1131, 2006.
Bottomley et al., "Structural and biochemical characterization of the wild type PCSK9/EGF-AB complex and natural FH mutants", J Biol Chem, Nov. 2008.
International Search Report and Written Opinion dated Nov. 23, 2009 in Application No. PCT/US2009/024775, filed Feb. 20, 2009.
Shan et al., "PCSK9 binds to multiple receptors and can be functionally inhibited by an EGF-A peptide", Biochem. Biophys. Res. Commun., pp. 1-5, 2008.
Zhang et al., "Structural requirements for PCSK9-mediated degredation of the low-density lipoprotein receptor", PNAS, 105(35): 13045-13050, 2008.
Zhao et al., "Molecular characterization of loss-of-function mutations in PCSK9 and identification of a compound heterozygote", Am. J. Hum. Genet, 79, 514-523, 2006.
Benjannet et al., "The porprotein convertase (PC) PCSK9 is inactivated by furin and/or PC5/6A: functional consequences of natural mutations and post-translational modifications", Journal of Biological Chemistry, vol. 281, No. 41, pp. 30561-30572, 2006.
Benjannet et al., "NARC-1/PCSK9 and Its Natural Mutants", Journal of Biological Chemistry, vol. 279, pp. 448846-48875, 2004.
Fan et al., "Self-association for human PCSK9 correlates with its LDLR-degrading activity", Biochemistry, 47:1631-1639, 2008.
Hampton et al., "The self-inhibited structure of full-length PCSK9 at 1.9 A reveals structural homology with resistin within the C-terminal domain", Proc Natl Acad Sci USA, 104(37:14604-14609, 2007.
Horton et al., "Molecular biology of PCSK9: its role in LDL metabolism", Trends Biochem Sci., 32(2):71-77, 2007.
Kwon et al., "Molecular basis for LDL receptor recognition by PCSK9", PNAS, 105:1820-1825, 2008.
Nassoury et al., "The cellular trafficking of the secretory proprotein convertase PCSK9 and its dependence on the LDLR", Traffic, 8(6):718-732, 2007.
Naureckiene et al., "Functional characterization of Narc 1, a novel proteinase related to proteinase K", Archives of Biochemistry and Biophysics, 420:55-67, 2003.
Piper et al., "The crystal structure of PCSK9: A regulator of plasma LDL-Cholesterol", Structure, Current Biology Ltd., vol. 15, No. 5, pp. 545-552, 2007.
Rashid et al., "Decreased plasma cholesterol and hypersensitivity to statins in mice lacking PCSK9", Proceedings of the National Academy of Sciences of USA, National Academy of Science, vol. 102, No. 15, pp. 5374-5379, 2005.
Schmit et al., "A novel splicing variant of proprotein convertase subtilisin/kexin type 9", DNA and Cell Biology, 27:183-189, 2008.
Seidah et al., "The proprotein convertases are potential targets in the treatment of dyslipidemia", J Mol. Med., 85(7):685-696, 2007.

* cited by examiner

*Primary Examiner* — Sharon X Wen
(74) *Attorney, Agent, or Firm* — Melissa A. Shaw

(57) ABSTRACT

Neutralizing PCSK9 variants that interact with low density lipoprotein receptor (LDLR) are described. Methods and compositions for treating disorders by administering a pharmaceutically effective amount of a neutralizing PCSK9 variant are described.

19 Claims, 38 Drawing Sheets

QEDEDGDYEELVLALRSEEDGLAEAPEHGTTATFHRCAKDPWRLPGTYVVVLKEETHLSQS
ERTARRLQAQAARRGYLTKILHVFHGLLPGFLVKMSGDLLELALKLPHVDYIEEDSSVFAQ
SIPWNLERITPPRYRADEYQPPDGGSLVEVYLLDTSIQSDHREIEGRVMVTDFENVPEEDG
TRFHRQASKCDSHGTHLAGVVSGRDAGVAKGASMRSLRVLNCQGKGTVSGTLIGLEFIRKS
QLVQPVGPLVVLLPLAGGYSRVLNAACQRLARAGVVLVTAAGNFRDDACLYSPASAPEVIT
VGATNAQDQPVTLGTLGTNFGRCVDLFAPGEDIIGASSDCSTCFVSQSGTSQAAAHVAGIA
AMMLSAEPELTLAELRQRLIHFSAKDVINEAWFPEDQRVLTPNLVAALPPSTHGAGWQLFC
RTVWSAHSGPTRMATAIARCAPDEELLSCSSFSRSGKRRGERMEAQGGKLVCRAHNAFGGE
GVYAIARCCLLPQANCSVHTAPPAEASMGTRVHCHQQGHVLTGCSSHWEVEDLGTHKPPVL
RPRGQPNQCVGHREASIHASCCHAPGLECKVKEHGIPAPQGQVTVACEEGWTLTGCSALPG
TSHVLGAYAVDNTCVVRSRDVSTTGSTSEEAVTAVAICCRSRHLAQASQELQ

SEQ ID NO:1

FIG. 1A

```
              10        20        30        40        50
         ----------|---------|---------|---------|---------|
Query  : atgggcaccgtcagctccaggcggtcctggtggccgctgccactgctgct   SEQ ID NO:2
Frame1 : M  G  T  V  S  S  R  R  S  W  W  P  L  P  L  L  L   SEQ ID NO:3

60        70        80        90       100
         ----------|---------|---------|---------|---------|
Query  : gctgctgctgctgctcctgggtcccgcgggcgcccgtgcgcaggaggacg
Frame1 : L  L  L  L  L  L  G  P  A  G  A  R  A  Q  E  D  E 110       120       130       140       150
         ----------|---------|---------|---------|---------|
Query  : aggacggcgactacgaggagctggtgctagccttgcgctccgaggaggac
Frame1 : D  G  D  Y  E  E  L  V  L  A  L  R  S  E  E  D 50       160       170       180       190       200
         ----------|---------|---------|---------|---------|
Query  : ggcctggccgaagcacccgagcacggaaccacagccaccttccaccgctg
Frame1 : G  L  A  E  A  P  E  H  G  T  T  A  T  F  H  R  C 210       220       230       240       250
         ----------|---------|---------|---------|---------|
Query  : cgccaaggatccgtggaggttgcctggcacctacgtggtggtgctgaagg
Frame1 : A  K  D  P  W  R  L  P  G  T  Y  V  V  V  L  K  E 50       260       270       280       290       300
         ----------|---------|---------|---------|---------|
Query  : aggagacccacctctcgcagtcagagcgcactgcccgccgcctgcaggcc
Frame1 : E  T  H  L  S  Q  S  E  R  T  A  R  R  L  Q  A 310       320       330       340       350
         ----------|---------|---------|---------|---------|
Query  : caggctgcccgccggggatacctcaccaagatcctgcatgtcttccatgg
Frame1 : Q  A  A  R  R  G  Y  L  T  K  I  L  H  V  F  H  G 50       360       370       380       390       400
         ----------|---------|---------|---------|---------|
Query  : ccttcttcctggcttcctggtgaagatgagtggcgacctgctggagctgg
Frame1 : L  L  P  G  F  L  V  K  M  S  G  D  L  L  E  L  A 410       420       430       440       450
         ----------|---------|---------|---------|---------|
Query  : ccttgaagttgccccatgtcgactacatcgaggaggactcctctgtcttt
Frame1 : L  K  L  P  H  V  D  Y  I  E  E  D  S  S  V  F 50       460       470       480       490       500
         ----------|---------|---------|---------|---------|
Query  : gcccagagcatcccgtggaacctggagcggattacccctccgcggtaccg
Frame1 : A  Q  S  I  P  W  N  L  E  R  I  T  P  P  R  Y  R 510       520       530       540       550
         ----------|---------|---------|---------|---------|
Query  : ggcggatgaataccagccccccgacggaggcagcctggtggaggtgtatc
Frame1 : A  D  E  Y  Q  P  P  D  G  G  S  L  V  E  V  Y  L
```

FIG. 1B$_1$

```
                 50       560        570        580        590        600
                  ---------|---------|---------|---------|---------|
Query  : tcctagacaccagcatacagagtgaccaccgggaaatcgagggcagggtc
Frame1 :   L  D  T  S  I  Q  S  D  H  R  E  I  E  G  R  V 610        620        630        640        650
                  ---------|---------|---------|---------|---------|
Query  : atggtcaccgacttcgagaatgtgcccgaggaggacgggacccgcttcca
Frame1 :   M  V  T  D  F  E  N  V  P  E  E  D  G  T  R  F  H 50       660        670        680        690        700
                  ---------|---------|---------|---------|---------|
Query  : cagacaggccagcaagtgtgacagtcatggcacccacctggcagggtgg
Frame1 :   R  Q  A  S  K  C  D  S  H  G  T  H  L  A  G  V  V 710        720        730        740        750
                  ---------|---------|---------|---------|---------|
Query  : tcagcggccgggatgccggcgtggccaagggtgccagcatgcgcagcctg
Frame1 :   S  G  R  D  A  G  V  A  K  G  A  S  M  R  S  L 50       760        770        780        790        800
                  ---------|---------|---------|---------|---------|
Query  : cgcgtgctcaactgccaagggaagggcacggttagcggcaccctcatagg
Frame1 :  R  V  L  N  C  Q  G  K  G  T  V  S  G  T  L  I  G 810        820        830        840        850
                  ---------|---------|---------|---------|---------|
Query  : cctggagtttattcggaaaagccagctggtccagcctgtggggccactgg
Frame1 :   L  E  F  I  R  K  S  Q  L  V  Q  P  V  G  P  L  V 50       860        870        880        890        900
                  ---------|---------|---------|---------|---------|
Query  : tggtgctgctgcccctggcgggtgggtacagccgcgtcctcaacgccgcc
Frame1 :   V  L  L  P  L  A  G  G  Y  S  R  V  L  N  A  A 910        920        930        940        950
                  ---------|---------|---------|---------|---------|
Query  : tgccagcgcctggcgagggctggggtcgtgctggtcaccgctgccggcaa
Frame1 :   C  Q  R  L  A  R  A  G  V  V  L  V  T  A  A  G  N 50       960        970        980        990        1000
                  ---------|---------|---------|---------|---------|
Query  : cttccgggacgatgcctgcctctactccccagcctcagctcccgaggtca
Frame1 :   F  R  D  D  A  C  L  Y  S  P  A  S  A  P  E  V  I 1010       1020       1030       1040       1050
                  ---------|---------|---------|---------|---------|
Query  : tcacagttggggccaccaatgcccaggaccagccggtgaccctggggact
Frame1 :   T  V  G  A  T  N  A  Q  D  Q  P  V  T  L  G  T 50       1060       1070       1080       1090       1100
                  ---------|---------|---------|---------|---------|
Query  : ttggggaccaactttggccgctgtgtggacctctttgccccaggggagga
Frame1 :   L  G  T  N  F  G  R  C  V  D  L  F  A  P  G  E  D
```

FIG. 1B$_2$

```
            100       1110      1120      1130      1140      1150
          ---------|---------|---------|---------|---------|---------|
Query   : catcattggtgcctccagcgactgcagcacctgctttgtgtcacagagtg
Frame1  :  I  I  G  A  S  S  D  C  S  T  C  F  V  S  Q  S  G 150       1160      1170      1180      1190      1200
          ---------|---------|---------|---------|---------|---------|
Query   : ggacatcacaggctgctgcccacgtggctggcattgcagccatgatgctg
Frame1  :  T  S  Q  A  A  A  H  V  A  G  I  A  A  M  M  L 200       1210      1220      1230      1240      1250
          ---------|---------|---------|---------|---------|---------|
Query   : tctgccgagccggagctcaccctggccgagttgaggcagagactgatcca
Frame1  :  S  A  E  P  E  L  T  L  A  E  L  R  Q  R  L  I  H 250       1260      1270      1280      1290      1300
          ---------|---------|---------|---------|---------|---------|
Query   : cttctctgccaaagatgtcatcaatgaggcctggttccctgaggaccagc
Frame1  :  F  S  A  K  D  V  I  N  E  A  W  F  P  E  D  Q  R 300       1310      1320      1330      1340      1350
          ---------|---------|---------|---------|---------|---------|
Query   : gggtactgaccccaacctggtggccgccctgccccccagcacccatggg
Frame1  :  V  L  T  P  N  L  V  A  A  L  P  P  S  T  H  G 350       1360      1370      1380      1390      1400
          ---------|---------|---------|---------|---------|---------|
Query   : gcaggttggcagctgttttgcaggactgtgtggtcagcacactcggggcc
Frame1  : A  G  W  Q  L  F  C  R  T  V  W  S  A  H  S  G  P 400       1410      1420      1430      1440      1450
          ---------|---------|---------|---------|---------|---------|
Query   : tacacggatggccacagccatcgcccgctgcgccccagatgaggagctgc
Frame1  :  T  R  M  A  T  A  I  A  R  C  A  P  D  E  E  L  L 450       1460      1470      1480      1490      1500
          ---------|---------|---------|---------|---------|---------|
Query   : tgagctgctccagtttctccaggagtgggaagcggcggggcgagcgcatg
Frame1  :  S  C  S  S  F  S  R  S  G  K  R  R  G  E  R  M 500       1510      1520      1530      1540      1550
          ---------|---------|---------|---------|---------|---------|
Query   : gaggcccaaggggggcaagctggtctgccgggcccacaacgcttttgggggg
Frame1  :  E  A  Q  G  G  K  L  V  C  R  A  H  N  A  F  G  G 550       1560      1570      1580      1590      1600
          ---------|---------|---------|---------|---------|---------|
Query   : tgagggtgtctacgccattgccaggtgctgcctgctaccccaggccaact
Frame1  :  E  G  V  Y  A  I  A  R  C  C  L  L  P  Q  A  N  C 600       1610      1620      1630      1640      1650
          ---------|---------|---------|---------|---------|---------|
Query   : gcagcgtccacacagctccaccagctgaggccagcatggggacccgtgtc
Frame1  :  S  V  H  T  A  P  P  A  E  A  S  M  G  T  R  V
```

FIG. 1B₃

```
             650       1660      1670      1680      1690      1700
         ---------|---------|---------|---------|---------|
Query  : cactgccaccaacagggccacgtcctcacaggctgcagctcccactggga
Frame1 :  H  C  H  Q  Q  G  H  V  L  T  G  C  S  S  H  W  E 700       1710      1720      1730      1740      1750
         ---------|---------|---------|---------|---------|
Query  : ggtggaggaccttggcacccacaagccgcctgtgctgaggccacgaggtc
Frame1 :  V  E  D  L  G  T  H  K  P  P  V  L  R  P  R  G  Q 750       1760      1770      1780      1790      1800
         ---------|---------|---------|---------|---------|
Query  : agcccaaccagtgcgtgggccacagggaggccagcatccacgcttcctgc
Frame1 :   P  N  Q  C  V  G  H  R  E  A  S  I  H  A  S  C 800       1810      1820      1830      1840      1850
         ---------|---------|---------|---------|---------|
Query  : tgccatgccccaggtctggaatgcaaagtcaaggagcatggaatcccggc
Frame1 :  C  H  A  P  G  L  E  C  K  V  K  E  H  G  I  P  A 850       1860      1870      1880      1890      1900
         ---------|---------|---------|---------|---------|
Query  : ccctcaggggcaggtgaccgtggcctgcgaggagggctggaccctgactg
Frame1 :   P  Q  G  Q  V  T  V  A  C  E  E  G  W  T  L  T  G 900       1910      1920      1930      1940      1950
         ---------|---------|---------|---------|---------|
Query  : gctgcagcgccctccctgggacctcccacgtcctgggggcctacgccgta
Frame1 :    C  S  A  L  P  G  T  S  H  V  L  G  A  Y  A  V 950       1960      1970      1980      1990      2000
         ---------|---------|---------|---------|---------|
Query  : gacaacacgtgtgtagtcaggagccgggacgtcagcactacaggcagcac
Frame1 :   D  N  T  C  V  V  R  S  R  D  V  S  T  T  G  S  T 2010      2020      2030      2040      2050
         ---------|---------|---------|---------|---------|
Query  : cagcgaagaggccgtgacagccgttgccatctgctgccggagccggcacc
Frame1 :   S  E  E  A  V  T  A  V  A  I  C  C  R  S  R  H  L 50       2060      2070      2080      2090      2100
         ---------|---------|---------|---------|---------|
Query  : tggcgcaggcctcccaggagctccag                    SEQ ID NO: 2
Frame1 :  A  Q  A  S  Q  E  L  Q                       SEQ ID NO: 3
```

FIG. 1B$_4$

```
                              1                                                50
rat PCSK9        (1)    MGIRCSTWLRWPLS----PQLLLLLLLCPTGSRAQDEDGDYEELMLALPS
cyno PCSK9       (1)    MGTVSSRRSWWPLP----LPLLLLLLLLGPAGARAQEDEDGDYEELVLALRS
human PCSK9      (1)    MGTVSSRRSWWPLP----LLLLLLLLLLGPAGARAQEDEDGDYEELVLALRS
guinea pig PCSK9 (1)    MRTRGPAPAWWPML----LLLMLGPAPAGAQARDSEDGDHEGLAFAFPP
hamster PCSK9    (1)    MGTSCSARPRWLLS----PLLLLLLLRYMGASAQDEDAEYEELMLTLQS
mouse PCSK9      (1)    MGTHCSAWLRWPLLPPLLPPPLLLLLLLCPTGAGAQDEDGDYEELMLALPS
Concensus        (1)    MGT CSARSWWPL    PLLLLLLLPAGAAAAQDEDGDYEELMLALPS
                        51                                              100
rat PCSK9        (47)   QEDSLVDEASHV---ATATFRRCSKEAWRLPGTYVVVLMEETQRLQVEQT
cyno PCSK9       (48)   EEDGLADAPEHG---ATATFHRCAKDPWRLPGTYVVVLKEETHRSQSERT
human PCSK9      (48)   EEDGLAEAPEHG---TTATFHRCAKDPWRLPGTYVVVLKEETHLSQSERT
guinea pig PCSK9 (46)   EEDGPAEAAPHVP---TAPFHRCSKDAWRLPGTYLVVLKEGTHRGQTKHT
hamster PCSK9    (47)   QDDGLADETDEAPQGATAAFHRCPEEAWRVPGTYIVMLAEEAQWHIEQT
mouse PCSK9      (51)   QEDGLADEAAHV---ATATFRRCSKEAWRLPGTYIVVLMEETQRLQIEQT
Consensus        (51)   QEDGLADEAEHV    ATATFHRCSKDAWRLPGTYVVVLKEETQRLQSEQT
                        101                                             150
rat PCSK9        (94)   AHRLQTWAARRGYVIKVLHVFYDLFPGFLVKMSSDLLGLALKLPHVEYIE
cyno PCSK9       (95)   ARRLQAQAARRGYLTKILHVFHHLLPGFLVKMSGDLLELALKLPHVDYIE
human PCSK9      (95)   ARRLQAQAARRGYLTKILHVFHGLLPGFLVKMSGDLLELALKLPHVDYIE
guinea pig PCSK9 (93)   AHRLQAKAARRGYVTTVLHLFHHLVPGFLVKMSGDLLDMALRLPLVQYIE
hamster PCSK9    (97)   MHRLQTQAARRGYVIKIQHIFYDFLPAFVVKMSSDLLDLALKLPHVKYIE
mouse PCSK9      (98)   AHRLQTRAARRGYVIKVLHIFYDLFPGFLVKMSSDLLGLALKLPHVEYIE
Consensus        (101)  AHRLQTQAARRGYVTKILHVFHDLLPGFLVKMSSDLLDLALKLPHVDYIE
                        151                                             200
rat PCSK9        (144)  EDSLVFAQSIPWNLERIIPAWQQTEEDSS----PDGSSQVEVYLLDTSIQ
cyno PCSK9       (145)  EDSSVFAQSIPWNLERITPARYRADEYQP----PKGGSIVEVYLLDTSIQ
human PCSK9      (145)  EDSSVFAQSIPWNLERITPPRYRADEYQP----PDGGSLVEVYLLDTSIQ
guinea pig PCSK9 (143)  EDSSVFAQSVPWNLERILPVRHQAKEYSAP----SHPVTVYLLDTSIQ
hamster PCSK9    (147)  EDSLVFAQSIPWNLDRIIPAGRQAQEYSSSRKVPSGSGQVEVYLLDTSIQ
mouse PCSK9      (148)  EDSFVFAQSIPWNLERIIPAWHQTEEDRS---PDGSSQVEVYLLDTSIQ
Consensus        (151)  EDSSVFAQSIPWNLERIIPARHQADEYSS    PDGSSQVEVYLLDTSIQ
                        201                                             250
rat PCSK9        (190)  SGHREIEGRVTITDFNSVPEEDGTRFHRQASKCDSHGTHLAGVVSGRDAG
cyno PCSK9       (191)  SDHREIEGRVMVTDFFESVPEEDGTRFHRQASKCDSHGTHLAGVVSGRDAG
human PCSK9      (191)  SDHREIEGRVMVTDFENVPEEDGTRFHRQASKCDSHGTHLAGVVSGRDAG
guinea pig PCSK9 (187)  SGHREIQGRITVTDFESVPQEDGTRFHRQASKCDSHGTHLAGVVSGRDAG
hamster PCSK9    (194)  SDHREIEGRVTVTDFNSVPEEDGTRFHRQASKCDSHGTHLAGVVSGRDAG
mouse PCSK9      (194)  GAHREIEGRVTITDFNSVPEEDGTRFHRQASKCDSHGTHLAGVVSGRDAG
Consensus        (201)  SDHREIEGRVTVTDFNSVPEEDGTRFHRQASKCDSHGTHLAGVVSGRDAG
```

FIG. 1C

```
                          251                                                              300
rat       PCSK9  (240)    VAKGTSLHSLRVLNCQGKGTVSGTLIGLEFIRKSQLIQPSGPLVLLPLA
cyno      PCSK9  (241)    VAKGAGLRSLRVLNCQGKGTVSGTLIGLEFIRKSQLVQPVGPLVLLPLA
human     PCSK9  (241)    VAKGASMRSLRVLNCQGRGTVSSTLRGLEFIRKSQLAQPVEPLVVLLPLA
guinea pig PCSK9 (237)    VAKGAGLRSLRVLNCQGKGTVSGTLIGLEFIRKSQLVQPVGPLVTLPLA
hamster   PCSK9  (247)    VAKGTIIHGLRVLNCQGKGTVSGILTGLEFIWKSQLMQPSGPQVVLLPLA
mouse     PCSK9  (244)    VAKGTSLHSLRVLNCQGKGTVSGTLIGLEFIRKSQLIQPSGPLVLLPLA
Concensus  (251)          VAKGTSLRSLRVLNCQGKGTVSGTLIGLEFIRKSQLIQPVGPLVVLLPLA
                          301                                                              350
rat       PCSK9  (290)    GGYSRILNTACQRLARTGVVLVAAAGNFRDDACLYSPASAPEVITVGATN
cyno      PCSK9  (291)    GGYSRVFNAACQRLARAGVVLVTAAGNFRDDACLYSPASAPEVITVGATN
human     PCSK9  (291)    GGYSRVLNAACQRLARAGVVLVTAAGNFRDDACLYSPASAPEVITVGATN
guinea pig PCSK9 (287)    GGYSRTLNAACHLLARAGVVLVAAAGNFRDDACLYSPASAPEVITVGATN
hamster   PCSK9  (297)    GRYSRVLNTACQHLARTGVVLVAAAGNFRDDACLYSPASAPEVITVGATD
mouse     PCSK9  (294)    GGYSRILNAACRHLARTGVVLVAAAGNFRDDACLYSPASAPEVITVGATN
Consensus  (301)          GGYSRVLNAACQRLARTGVVLVAAAGNFRDDACLYSPASAPEVITVGATN
                          351                                                              400
rat       PCSK9  (340)    AQDQPVTLGTNFGRCVDLFAPGKDIIGASSDCSTCYMSQSGTSQAAA
cyno      PCSK9  (341)    AQDQPVTLGTNFGRCVDLFAPGEDIIGASSDCSTCFVSRSGTSQAAA
human     PCSK9  (341)    AQDQPVTLGTNFGRCVDLFAPGEDIIGASSDCSTCFVSQSGTSQAAA
guinea pig PCSK9 (337)    AQDQPVTLGTNFGRCVDLFAPGKDIIGASSDCSTCFVSRSGTSQAAA
hamster   PCSK9  (347)    VQDQPVTLGTNFGRCVDLFAPGKDIIGASSDCSACFMSQSGTSQAAA
mouse     PCSK9  (344)    AQDQPVTLGTNFGRCVDLFAPGKDIIGASSDCSTCFMSQSGTSQAAA
Consensus  (351)          AQDQPVTLGTNFGRCVDLFAPGKDIIGASSDCSTCFMSQSGTSQAAA
                          401                                                              450
rat       PCSK9  (390)    HVAGIVAMMLNRDPALTLAELRQRLILFSTKDVINMAWFPEDQRVLTPNR
cyno      PCSK9  (391)    HVAGIAAMLSAEPELITLAELRQRLIHFSAKDVINEAWFPEDQRVLTPNL
human     PCSK9  (391)    HVAGIAAMLSAEPELITLAELRQRLIHFSAKDVINEAWFPEDQRVLTPNL
guinea pig PCSK9 (387)    HVAGIVTMMLTAQPKLITLAELWQRLIHFSAKDVINEAWFPEDQRVLTPNL
hamster   PCSK9  (397)    HVAGIVAMMLTLEPELITLAELRQRLIHFSTKDAINMAWFPEDQRVLTPNL
mouse     PCSK9  (394)    HVAGIVARMLSREPTLTLAELRQRLIHFSTKDVINMAWFPEDQQVLTPNL
Consensus  (401)          HVAGIVAMMLSAEPELITLAELRQRLIHFSTKDVINMAWFPEDQRVLTPNL
                          451                                                              500
rat       PCSK9  (440)    VATLPPSTQETGGQLLCRTVWSAHSGPTRTATATARCAPEEELLSCSSFS
cyno      PCSK9  (441)    VAALPPSTHRAGWQLFCRTVWSAHSGPTRMATAVARCAQDEELLSCSSFS
human     PCSK9  (441)    VAALPPSTHGAGWQLFCRTVWSAHSGPTRMATAIARCAPDEELLSCSSFS
guinea pig PCSK9 (437)    VAALPPSTRGAGGRLLCRTVWSARSGPRHTATALAHCTPGEELLSCSSFS
hamster   PCSK9  (447)    VATLPPSTHGTGGQLLCRTVWSAHSGPTRAATATARCAPGEELLSCSSFS
mouse     PCSK9  (444)    VATLPPSTHETGGQLLCRTVWSAHSGPTRTATATARCAPEEELLSCSSFS
Consensus  (451)          VATLPPSTHGTGGQLLCRTVWSAHSGPTRTATATARCAPDEELLSCSSFS
```

FIG. 1D

```
rat     PCSK9 (490) RSGRRRGDRIEAIGGQQVCKALNAFGGEGVYAVARCCLLPRVNCSIHNTP
cyno    PCSK9 (491) RSGKRRGERIEAAQGGKRVCRAHNAFGGEGVYAIARCCLLPQVNCSVHTAP
human   PCSK9 (491) RSGKRRGERMEAQGGKLVCRAHNAFGGEGVYAIARCCLLPQANCSVHTAP
guinea pig PCSK9 (487) RSGKRKGERIEVLRGRRVCVAYNAFGGKGVHAVARCCLLPRANCSLHTAP
hamster PCSK9 (497) RSGRRRGDRIEAAGTQQVCKALNAFGGEGVYAVARCCLLPRANCSIHTTP
mouse   PCSK9 (494) RSGRRRGDWIEAIGGQQVCKALNAFGGEGVYAVARCCLVPRANCSIHNTP
Concensus     (501) RSGKRRGDRIEAIGGQQVCKALNAFGGEGVYAVARCCLLPRANCSIHTTP
                    551                                              600
rat     PCSK9 (540) AARAGPQTPVHCHQKDHVLTGCSFHWEVENLRAQQQPLLRSRHQPGQCVG
cyno    PCSK9 (541) PAGASMGTRVHCHQQGHVLTGCSSHWEVEDLGTHKPPVLRPRGQPNQCVG
human   PCSK9 (541) PAEASMGTRVHCHQQGHVLTGCSSHWEVEDLGTHKPPVLRPRGQPNQCVG
guinea pig PCSK9 (537) -ARAGMEPRVHCHRKDQVLTGCSAHWEAEDFRARGWPMLRP-GGPSQCVG
hamster PCSK9 (547) AARTSLETHAHCHQKDHVLTGCSLHWEVEGIGVQPLAVLRSRHQPGQCTG
mouse   PCSK9 (544) AARAGLETHVHCHQKDHVLTGCSFHWEVEDLSVRRQPALRSRRQPGQCVG
Consensus     (551) AARASMETRVHCHQKDHVLTGCSSHWEVEDLG  K PVLRSRGQPGQCVG
                    601                                              650
rat     PCSK9 (590) HQEASVHASCCHAPGLECKIKEHGIAGPAEQVTVACEAGWTLTGCNVLPG
cyno    PCSK9 (591) HREASIHASCCHAPGLECKVREHGIPAPQEQVIVACEDGWTLTGCSALPG
human   PCSK9 (591) HREASIHASCCHAPGLECKVKEHGIPAPQEQVTVACEEGWTLTGCSALPG
guinea pig PCSK9 (585) HSKASVHASCCSAPGLECRIREHGVPWPAEQVTVACEDGWTLTGCSTLPG
hamster PCSK9 (597) HREASVHASCCHAPGLECKIKEHGISGPAEQVTVACEAGWTLTGCNVLPG
mouse   PCSK9 (594) HQAASVYASCCHAPGLECKIKEHGISGPSEQVTVACEAGWTLTGCNVLPG
Consensus     (601) HREASVHASCCHAPGLECKIKEHGIPGPAEQVTVACEAGWTLTGCSVLPG
                    651                                              700
rat     PCSK9 (640) ASLPLGAYSVDNVCVARIRDAGRADRTSEEATVAAAICCRSPSAKASWV
cyno    PCSK9 (641) TSHVLGAYAVDNTCVVRSRDVSTTGSTSEEAVAAAVAICCRSRHLVQASQE
human   PCSK9 (641) TSHVLGAYAVDNTCVVRSRDVSTTGSTSEEAVTAVAICCRSRHLAQASQE
guinea pig PCSK9 (635) ASSVLGTYAVDDMCVVRSRDVKALDRTRGEALAAIAICCRSQASEQASPE
hamster PCSK9 (647) AFITLGAYADNTCVARSRVTDTAGRTGEEATVAAAICCRNRPSAKASWV
mouse   PCSK9 (644) ASLTLGAYSVDNLCVARVHDTARADRTSGEATVAAAICCRSRPSAKASWV
Consensus     (651) ASLVLGAYAVDNTCVVRSRDVSTAGRTSEEATVAAAICCRSRPSAQASWV
                    701       723
rat     PCSK9 (690) HQH------HHHHHHH-
cyno    PCSK9 (691) LQGKPIPNPLLGLDSTHHHHHH-
human   PCSK9 (691) LQG------PHHHHHHHH-
guinea pig PCSK9 (685) RQH------HHHHH---
hamster PCSK9 (697) HQH------HHHHH---
mouse   PCSK9 (694) QGP------HHHHHHH-
Consensus     (701) QH       HHHHHHH
```

SEQ ID NOs:
8
7
24
4
5
6
9

FIG. 1E

```
Query    1    SIPWNLERITPPRYRADEYQPPDGGSLVEVYLLDTSIQSDHREIEGRVMVTDFENVPEED    60
              SIPWNL+RI    R++EY PP+ G  VEVYLLDTS+QS HREIEG+V V DFE+VP+ED
Sbjct  368    SIPWNLDRIVLAPSRSEEYSPPNKGDQVEVYLLDTSLQSGHREIEGKVTVADFEDVPDED   427

Query   61    GTRFHRQASKCDSHGTHLAGVVSGRDAGVAKGASMRSLRVLNCQGKGTVSGTLIGLEFIR   120
              G +FH QASKC+SHGTH+AGV+SGRDAGVA+ A++RS+RVLNCQGKGTVSGT GLEFIR
Sbjct  428    GAQFHSQASKCESHGTHVAGVLSGRDAGVARAAAVRSVRVLNCQGKGTVSGTARGLEFIR   487

Query  121    KSQLVQPVGPLVVLLPLAGGYSRVLNAACQRLARAGVVLVTAAGNFRDDACLYSPASAPE   180
              ++QLVQP  PL+VLLP AGG+SR LNAAC+ L R+G  ++ AAGN+RDDAC YSPAS PE
Sbjct  488    RTQLVQPYSPLIVLLPFAGGHSRTLNAACRLLVRSGAAVIAAAGNYRDDACSYSPASEPE   547

Query  181    VITVGATNAQDQPVTLGTLGTNFGRCVDLFAPGEDIIGASSDCSTCFVSQSGTSQAAAHV   240
              VITVGATNAQDQP   LG  LGTNFGRCVDLFAPGEDIIGASSDC TCF SQSGTSQAAAHV
Sbjct  548    VITVGATNAQDQPAALGALGTNFGRCVDLFAPGEDIIGASSDCGTCFTSQSGTSQAAAHV   607

Query  241    AGIAAMMLSAEPELTLAELRQRLIHFSAKDVINEAWFPEDQRVLTPNLVAALP          293    SEQ ID NO: 10
              AGIA+M+L+AEP LT+ ELRQRLIHFS K+ INEAWFPEDQR+LTPNLVA LP                       11
Sbjct  608    AGIASMLLNAEPSLTVPELRQRLIHFSVKNAINEAWFPEDQRLLTPNLVARLP          660                12
```

FIG. 1F

```
Query    1    SIPWNLERITPPRYRADEYQPPDGGSLVEVYLLDTSIQSDHREIEGRVMTDFENVPEED      60
              S+PWNL+RI P + A ++ PP+ G   VEVYLLDTSIQS+HREIEG+V VTDF+NVPEED
Sbjct    144  SVPWNLDRIVPAQQMASQFSPPNTGDSVEVYLLDTSIQSNHREIEGKVFVTDFQNVPEED    203

Query    61   GTRFHRQASKCDSHGTHLAGVVSGRDAGVAKGASMRSLRVLNCQGKGTVSGTLIGLEFIR     120
              GTRFHRQASKC+SHGTH+AGVV+GRDAGVAKG  ++RSLRVLNCQGKGTVSG+L GLEFIR
Sbjct    204  GTRFHRQASKCESHGTHMAGVVNGRDAGVAKGVNVRSLRVLNCQGKGTVSGSLTGLEFIR    263

Query    121  KSQLVQPVGPLVVLLPLAGGYSRVLNAACQRLARAGVVLVTAAGNFRDDACLYSPASAPE     180
              K+ + QP  PL+V++P  GGYSR+LNAA + L    GV+++  AAGN++DDACLYSPAS PE
Sbjct    264  KTLIEQPYNPLIVIIPFVGGYSRILNAASRALVNTGVIIAAAGNYKDDACLYSPASEPE    323

Query    181  VITVGATNAQDQPVTLGTLGTNFGRCVDLFAPGEDIIGASSDCSTCFVSQSGTSQAAAHV    240
              VIT+GATN QDQP T+G LGTN+G C+DLFAPG+DIIGASSDCSTCF S+SGTSQAAAHV
Sbjct    324  VITIGATNYQDQPATMGVLGTNYGNCIDLFAPGDDIIGASSDCSTCFTSKSGTSQAAAHV    383

Query    241  AGIAAMMLSAEPELTLAELRQRLIHFSAKDVINEAWFPEDQRVLTPNLVAALP           293    10
              AGIAAM+L+ +P+L+++ELRQRLI FS K VINE WFPEDQR++TPN VA LP                 13
Sbjct    384  AGIAAMILNDKPDLSVSELRQRLIQFSTKKVINEVWFPEDQRLITPNRVAGLP           436    14
                                                                               SEQ ID
                                                                               NO:
```

FIG. 1G

```
Query    3    PWNLERITPPRYRADEYQPPDGGSLVEVYLLDTSIQSDHREIEGRVMVTDFENVPEEDGT    62
              PW+L R+  PR R   P  G+ VEVYL+D S+ S HRE+ GRV+VTDF +VP  +
Sbjct   84    PWSLRRLPRPRGR-----PGDGAAVEVYLMDGSVLSSHRELGGRVLVTDFHSVPVGEAG    137

Query   63    RFHRQASKCDSHGTHLAGVVSGRDAGVAKGASMRSLRVLNCQKGTVSGTLIGLEFIRKS    122
              HR+AS+C  HGTH+A VV G D GVA GA +  +RVL+C+GKGTVSG L G+E+IR +
Sbjct  138    G-HREASRCKGHGTHVAAVVMGSDTGVAPGARVNLVRVLDCRGKGTVSGALAGVEYIRAA    196

Query  123    QLVQPVGPLVVLLPLAGGYSRVLNAACQRLARAGVVLVTAAGNFRDDACLYSPASAPE--    180
              P G  VVLLP  G +SR LNAAC+   L   G V+V AAGN+RDDACLYSPAS PE
Sbjct  197    LRAHPPGAAVVLLPFTGAFSRSLNAACRDLVNTGAVVVAAAGNYRDDACLYSPASEPEVC    256

Query  181    ------------------------------VITVGATNAQDQPVTLGTLGTNFGRCVDLFA    211
                                            VITVGA N+ DQ V+  G  GTN GRCVD+FA
Sbjct  257    TGGSARSHTHTHTHTHLLQAVLCVCVQVITVGAVNSADQLVSQGPGGTNVGRCVDVFA    316

Query  212    PGEDIIGASSDCSTCFVSQSGTSQAAAHVAGIAAMMLSAEPELTLAELRQRLIHFSAKDV    271
              PG DI+ ASSDC TCF S SGTSQAAAH AG+AA++LS+ P LT  ++ Q L+ +S
Sbjct  317    PGGDIVSASSDCDTCFASGSGTSQAAAHAAGMAAVLLSSSPSLTPVQVLQTLLRYS---    372

Query  272    INEAWFPEDQRVLTPNLVAALPP    294    17
              ++         + ++TP+LVAALPP                   15
Sbjct  373    VSLPSVSGRRGLVTPSLVAALPP    395    16
                                            SEQ ID NO:
```

FIG. 1H

FIG. 1I  Sequence of Human and Mouse LDLR

FIG. 1J  Sequence of Human and Mouse LDLR

```
                              β-Propeller 2                                                                                    Section 7
                     450    c     460         470         480         490         500        511
hLDLR P01130   (439) 439 SNRIYWSDLSQRMICSTQLDRAHGVSSYDTVISRDIQAPDGLAVDWIHSNIYWTDSVLGTVSVADTKGVKRKT
mLDLR NP_034830(438)     NNRIYWSDLSQKKIYSALMDIAPNIS-YDTIISEDLHAPDGLAVDWIHRNIYWTDSVPGSVSVADTKGVKRRT
Consensus      (439)     NRIYWSDLSQK I S   LD A  LS YDTIIS DI APDGLAVDWIH NIYWTDSV GSVSVADTKGVKRKT Section 8
                              β-Propeller 3                                  β-Propeller 4
                     512    520         530         540         550         560         570        584
hLDLR P01130   (511) LFRENGSKPRAIVVDPVHGFMYWTDWGTPAKIKKGGLNGVDIYSLVTENIQWPNGITLDLLSGRLYWDSKLH
mLDLR NP_034830(511) LFQEAGSRPRAIVVDPVHGFMYWTDWGTPAKIKKGGLNGVDIHSLVTENIQWPNGITLDLSSGRLYWDSKLH
Consensus      (512) LF E GSKPRAIVVDPVHGFMYWTDWGTPAKIKKGGLNGVDIHSLVTENIQWPNGITLDL SGRLYWDSKLH β-Propeller 5                                  β-Propeller 6                                     Section 9
                     585    590         600         610         620         630         640        657
hLDLR P01130   (584) SISSIDVNGGNRKTILEDEKRLAHPFSLAVFEDKVFWTDIINEAIFSANRLTGSDVNLIAENLLSPEDMVLFH
mLDLR NP_034830(584) SISSIDVNGGNRKTILEDENRLAHPFSLAIYEDKVYWTDVINEAIFSANRLTGSDVNLVAENLLSPEDIVLFH
Consensus      (585) SISSIDVNGGNRKTILEDE RLAHPFSLAIFEDKVFWTDI INEAIFSANRLTGSDVNLLAENLLSPEDIVLFH C         C     EGF-like C     C  C C                                                            Section 10
                     658    670         680         690         700    710         720        730
hLDLR P01130   (657) NLTQPRGVNWCERTTLS-NGGCQYLCLPAPQINPHSPKFTCACPDGMLLARDMRSCLTEAEAAVATQETSTVR
mLDLR NP_034830(657) KVTQPRGVNWCETTALLPNGGCQYLCLPAPQIGPHSPKFTCACPDGMLLAKDMRSCLTEVDTVLHTQGTSAVR
Consensus      (658) LTQPRGVNWCE T L NGGCQYLCLPAPQI PHSPKFTCACPDGMLLA KDMRSCLTE D  L TQ TS VR O-glycosylation                                                                              Section 11
                     731    740         750         760         770         780         790        803
hLDLR P01130   (729) LKVSSTAVR-TQHTTTRPVPDTSRLPGATPGLTTVEIVTMSHQALGDVAGRGNEKKPSSVRALSIVLPIVLLV
mLDLR NP_034830(730) PVVTASATRPPKHSEDLSAPSTPRQPVDTPGLSTVASVTVSHQVQGDMAGRGNEEQPHGMRFLSIFFPIALVA
Consensus      (731) VSASA R   HS   P T R P  TPGLSTV  VTMSHQ  GDMAGRGNE  P   MR LSI  PI LL TM                  Endocytosis signal                                                                    Section 12
                     804    810         820         830         840         850        865        SEQ ID NO:
hLDLR P01130   (801) FLCLGVFLLMWRLKN--INSINFDNPVYQKTTEDEVHICHNQDGYSYPSRQMVSLEDDVA                    18
mLDLR NP_034830(803) LLVLGAVLLWRNWRLKNITINSINFDNPVYQKTTEDELHICRSQDGYTYPSRQMVSLEDDVA                   20
Consensus      (804) L LG  LLWKNWRLKN  INSINFDNPVYQKTTEDELHIC  QDGYSYPSRQMVSLEDDVA                  21
```

FIG. 1K  Sequence of Human and Cyno LDLR

```
                                                                                                                           Section 1
                        1          10         20         30         40         50         60         72
hLDLR 20080009918   (1) MGPWGWKLRWTVALLLAAAGTAVGDRCERNEFQCQDGKCISYKWVCDGSAECQDGSDESQETCLSVTCKSGD
cynLDLR 20080068365 (1) MEPWGWKLRWTVAFLLAAAEAAVGDRCERNEFQCEDGKCISYKWVCDGTAECQDGSDESQETCLSVTCKSGD
Consensus           (1) M PWGWKLRWTVA LLAAA  AVGDRCERNEFQC DGKCISYKWVCDGSAECQDGSDESQETCLSVTCKSGD Section 2
                        73         80         90        100        110        120        130        144
hLDLR 20080009918   (73) FSCGGRVNRCIPQFWRCDGQVDCDNGSDEQGCPPKTCSQDEFRCHDGKCISRQFVCDSDRDCLDGSDEASCP
cynLDLR 20080068365 (73) FSCGGRVNRCIPQFWRCDGEVDCENGSDEQDCPPKTCSQDEFRCHDGKCIYRQFVCDSDRDCLDGSDEASCP
Consensus           (73) FSCGGRVNRCIPQFWRCDG VDCDNGSDEQ CPPKTCSQDEFRCHDGKCI RQFVCDSDRDCLDGSDEASCP Section 3
                        145        150        160        170        180        190        200        216
hLDLR 20080009918   (145) VLTCGPASFQCNSSTCIPQLWACDNDPDCEDGSDEWPQRCRGLYVFQGDSSPCSAFEFHCLSGECIHSSWRC
cynLDLR 20080068365 (145) VLTCGPASFQCNSSTCIPQLWACDNDPDCEDGSDEWPQHCQGLEVPKRDSSPCSAFEFHCQSGECIHSGWRC
Consensus           (145) VLTCGPASFQCNSSTCIPQLWACDNDPDCEDGSDEWPQ C GL V  DSSPCSAFEFHC SGECIHS WRC Section 4
                        217        230        240        250        260        270        288
hLDLR 20080009918   (217) DGGPDCKDKSDEENCAVATCRPDEFQCSDGNCIHGSRQCDREYDCKDMSDEVGCVNVTLCEGPNKFKCHSGE
cynLDLR 20080068365 (217) DGGPDCKDKSDEENCPVATCRPDEFQCSDGTCIHGSRQCDREYDCKDMSDEVGCINVTLCEGPNKFKCHSGE
Consensus           (217) DGGPDCKDKSDEENC VATCRPDEFQCSDG CIHGSRQCDREYDCKDMSDEVGCINVTLCEGPNKFKCHSGE Section 5
                        289        300        310        320        330        340        350        360
hLDLR 20080009918   (289) CITLDKVCNMARDCRDWSDEPIKECGTNECLDNNGGCSHVCNDLKIGYECLCPDGFQLVAQRRCEDIDECQD
cynLDLR 20080068365 (289) CISLDKVCNMARDCRDWSDEPIKECGTNECLDNNGGCSHICNDLKIGYECLCPDGFQLVAQRRCEDIDECQD
Consensus           (289) CISLDKVCNMARDCRDWSDEPIKECGTNECLDNNGGCSHICNDLKIGYECLCPDGFQLVAQRRCEDIDECQD Section 6
                        361        370        380        390        400        410        420        432
hLDLR 20080009918   (361) PDTCSQLCVNLEGGYKCQCEEGFQLDPHTKACKAVGSIAYLFFTNRHEVRKMTLDRSEYTSLIPNLRNVVAL
cynLDLR 20080068365 (361) PDTCSQLCVNLEGSYKCQCEEGFQLDPHTKACKAVGSIAYLIFTNRHEVRKMTLDRSEYTSLIPNLRNVVAL
Consensus           (361) PDTCSQLCVNLEG YKCQCEEGFQLDPHTKACKAVGSIAYL FTNRHEVRKMTLDRSEYTSLIPNLRNVVAL
```

FIG. 1L                Sequence of Human and Cyno LDLR

```
                                                                                                              Section 7
                 (433)  433                     450         460         470         480         490        504
hLDLR 20080009918 (433) DTEVASNRIYWSDLSQRMICSTQLDRAHGVSSYDTVISRDIQAPDGLAVDWIHSNIYWTDSVLGTVSVADTK
cynLDLR 20080068365 (433) DTEVASNRIYWSDLSQRMIYSTQLDRAHSVSSYDTVISRDIQAPDGLAVDWIHSNIYWTDSVLGTVSVADTK
         Consensus (433) DTEVASNRIYWSDLSQRMI  STQLDRAH VSSYDTVISRDIQAPDGLAVDWIHSNIYWTDSVLGTVSVADTK
                                                                                                              Section 8
                 (505)  505         520         530         540         550         560        576
hLDLR 20080009918 (505) GVKRKTLFRENGSKPRAIVVDPVHGFMYWTDWGTPAKIKKGGLNGVDIYSLVTENIQWPNGITLDLLSGRLY
cynLDLR 20080068365 (505) GVKRKTLFRENGSKPRAIVVDPVHGFMYWTDWGTPAKIKKGGLNGVDIYSLVTENIEWPNGITLDFPSGRLY
         Consensus (505) GVKRKTLFRENGSKPRAIVVDPVHGFMYWTDWGTPAKIKKGGLNGVDIYSLVTENI WPNGITLD  SGRLY
                                                                                                              Section 9
                 (577)  577         590         600         610         620         630        648
hLDLR 20080009918 (577) WVDSKLHSISSIDVNGGNRKTILEDEKRLAHPFSLAVFEDKVFWTDIINEAIFSANRLTGSDVNLLAENLLS
cynLDLR 20080068365 (577) WVDSKLHSISSIDVNGGNRKTVLEDEERLAHPFSLAIFEDKVFWTDIINEAIFSANRLTGSDINLLAENLLS
         Consensus (577) WVDSKLHSISSIDVNGGNRKTILEDE RLAHPFSLA FEDKVFWTDIINEAIFSANRLTGSD NLLAENLLS
                                                                                                             Section 10
                 (649)  649         660         670         680         690         700        710        720
hLDLR 20080009918 (649) PEDMVLFHNLITQPRGVNWCERTTLSNGGCQYLCLPAPQINPHSPKFTCACPDGMLLARDMRSCLTEAEAAVA
cynLDLR 20080068365 (649) PEDMVLFHNLITQPRGVNWCERTTLSNGGCQYLCLPAPQINPQSPKFTCTCPDGMLLAKDMRSCLTEAEAAVA
         Consensus (649) PEDMVLFHNLITQPRGVNWCERTTLSNGGCQYLCLPAPQINP SPKFTC CPDGMLLAKDMRSCLTEAEAAVA
                                                                                                             Section 11
                 (721)  721         730         740         750         760         770        780        792
hLDLR 20080009918 (721) TQETSTVRLKVSSTAVRTQHTTTRPVPDTSRLPGATPGLTTVEIVTMSHQALGDVAGRGNEKKPSSVRALSI
cynLDLR 20080068365 (721) TQETSTVRLMVSSKAVATQHTTTRPVPNTSQLPGATPGLTTAETVTMSHQALGDVAGRGNEKKPKSVGALSI
         Consensus (721) TQETSTVRL VSS AV TQHTTTRPVP TS LPGATPGLTT E VTMSHQALGDVAGRGNEKKP SV ALSI
                                                                                                             Section 12
                 (793)  793         810         820         830         840         850        860   SEQ ID NO:
hLDLR 20080009918 (793) VLPIVLLVFLCLGVFLLWKNWRLKNINSINFDNPVYQKTTEDEVHICHNQDGYSYPSRQMVSLEDDVA     18
cynLDLR 20080068365 (793) VLPTVLLVFLCLGAFLLWKNWRLKSINSINFDNPVYQKTTEDEVHICRNQDGYSYPSRQMVSLEDDVA     19
         Consensus (793) VLP VLLVFLCLG FLLWKNWRLK INSINFDNPVYQKTTEDEVHIC NQDGYSYPSRQMVSLEDDVA     22
```

Cavia porcellus PCSK9

```
Met Arg Thr Arg Gly Pro Ala Pro Ala Trp Trp Pro Met Leu Leu Leu
 1               5                  10                      15
Leu Met Leu Gly Pro Ala Pro Ala Gly Ala Gln Ala Arg Asp Ser Glu
            20              25                  30
Asp Gly Asp His Glu Gly Leu Ala Phe Ala Phe Pro Pro Glu Glu Asp
        35              40              45
Gly Pro Ala Glu Ala Ala Pro His Val Pro Thr Ala Pro Phe His Arg
    50              55              60
Cys Ser Lys Asp Ala Trp Arg Leu Pro Gly Thr Tyr Leu Val Val Leu
65              70                      75                  80
Lys Glu Gly Thr His Arg Gly Gln Thr Lys His Thr Ala His Arg Leu
                85              90                      95
Gln Ala Lys Ala Ala Arg Arg Gly Tyr Val Thr Thr Val Leu His Leu
            100             105                 110
Phe His His Leu Val Pro Gly Phe Leu Val Arg Met Ser Gly Asp Leu
        115             120                 125
Leu Asp Met Ala Leu Arg Leu Pro Leu Val Gln Tyr Ile Glu Glu Asp
    130             135                 140
Ser Ser Val Phe Ala Gln Ser Val Pro Trp Asn Leu Glu Arg Ile Leu
145             150                 155                     160
Pro Val Arg His Gln Ala Lys Glu Tyr Ser Ala Pro Ser His Pro Val
                165             170                 175
Thr Val Tyr Leu Leu Asp Thr Ser Ile Gln Ser Gly His Arg Glu Ile
            180             185                 190
Gln Gly Arg Ile Thr Val Thr Asp Phe Glu Ser Val Pro Gln Glu Asp
        195             200                 205
Gly Thr Arg Phe His Arg Gln Ala Ser Lys Cys Asp Ser His Gly Thr
    210             215                 220
His Leu Ala Gly Val Val Ser Gly Arg Asp Ala Gly Val Ala Lys Gly
225             230                 235                     240
Ala Gly Leu Arg Ser Leu Arg Val Leu Asn Cys Gln Gly Arg Gly Thr
                245             250                 255
Val Ser Ser Thr Leu Arg Gly Leu Glu Phe Ile Arg Lys Ser Gln Leu
            260             265                 270
Ala Gln Pro Val Glu Pro Leu Val Val Leu Leu Pro Leu Ala Gly Gly
        275             280                 285
Tyr Ser Arg Thr Leu Asn Ala Ala Cys His Leu Leu Ala Arg Ala Gly
    290             295                 300
Val Val Leu Val Ala Ala Ala Gly Asn Phe Arg Asp Asp Ala Cys Leu
305             310                 315                     320
Tyr Ser Pro Ala Ser Ala Pro Glu Val Ile Thr Val Gly Ala Thr Asn
                325             330                 335
Ala Gln Asp Gln Pro Val Thr Leu Gly Thr Leu Gly Thr Asn Phe Gly
            340             345                 350
Arg Cys Val Asp Leu Phe Ala Pro Gly Glu Asp Ile Ile Gly Ala Ser
        355             360                 365
Ser Asp Cys Ser Thr Cys Phe Val Ser Arg Ser Gly Thr Ser Gln Ala
    370             375                 380
```

FIG 1M₁

```
Ala Ala His Val Ala Gly Ile Val Thr Met Met Leu Thr Ala Gln Pro
385             390             395                 400
Lys Leu Thr Leu Ala Glu Leu Trp Gln Arg Leu Ile His Phe Ala Ala
                405             410                 415
Lys Asp Val Ile Asn Glu Ala Trp Phe Pro Glu Asp Gln Arg Val Leu
            420             425             430
Thr Pro Asn Leu Val Ala Thr Leu Pro Pro Ser Thr Arg Gly Ala Gly
            435             440             445
Gly Arg Leu Leu Cys Arg Thr Val Trp Ser Ala Arg Ser Gly Pro Arg
        450             455             460
His Thr Ala Thr Ala Leu Ala His Cys Thr Pro Gly Glu Glu Leu Leu
465             470             475                 480
Ser Cys Ser Ser Phe Ser Arg Ser Gly Lys Arg Lys Gly Glu Arg Ile
                485             490                 495
Glu Val Leu Arg Gly Arg Arg Val Cys Val Ala Tyr Asn Ala Phe Gly
            500             505             510
Gly Lys Gly Val His Ala Val Ala Arg Cys Cys Leu Leu Pro Arg Ala
        515             520             525
Asn Cys Ser Leu His Thr Ala Pro Ala Arg Ala Gly Met Glu Pro Arg
    530             535             540
Val His Cys His Arg Lys Asp Gln Val Leu Thr Gly Cys Ser Ala His
545             550             555                 560
Trp Glu Ala Glu Asp Phe Arg Ala Arg Gly Trp Pro Met Leu Arg Pro
                565             570             575
Gly Gly Pro Ser Gln Cys Val Gly His Ser Lys Ala Ser Val His Ala
            580             585             590
Ser Cys Cys Ser Ala Pro Gly Leu Glu Cys Arg Ile Arg Glu His Gly
        595             600             605
Val Pro Trp Pro Ala Glu Gln Val Thr Val Ala Cys Glu Asp Gly Trp
    610             615             620
Thr Leu Thr Gly Cys Ser Thr Leu Pro Gly Ala Ser Ser Val Leu Gly
625             630             635                 640
Thr Tyr Ala Val Asp Asp Met Cys Val Val Arg Ser Arg Asp Val Lys
                645             650             655
Ala Leu Asp Arg Thr Arg Gly Glu Ala Leu Ala Ala Ile Ala Ile Cys
            660             665             670
Cys Arg Ser Gln Ala Ser Glu Gln Ala Ser Pro Glu Arg Gln
        675             680             685

SEQ ID NO: 25
```

FIG 1M$_2$

Mesocricetus auratus PCSK9

```
Met Gly Thr Ser Cys Ser Ala Arg Pro Arg Trp Leu Leu Ser Pro Leu
1               5                   10                  15
Leu Leu Leu Leu Leu Leu Leu Arg Tyr Met Gly Ala Ser Ala Gln Asp
            20                  25                  30
Glu Asp Ala Glu Tyr Glu Glu Leu Met Leu Thr Leu Gln Ser Gln Asp
            35                  40                  45
Asp Gly Leu Ala Asp Glu Thr Asp Glu Ala Pro Gln Gly Ala Thr Ala
        50                  55                  60
Ala Phe His Arg Cys Pro Glu Glu Ala Trp Arg Val Pro Gly Thr Tyr
65                  70                  75                  80
Ile Val Met Leu Ala Glu Glu Ala Gln Trp Val His Ile Glu Gln Thr
                85                  90                  95
Met His Arg Leu Gln Thr Gln Ala Ala Arg Arg Gly Tyr Val Ile Lys
            100                 105                 110
Ile Gln His Ile Phe Tyr Asp Phe Leu Pro Ala Phe Val Val Lys Met
            115                 120                 125
Ser Ser Asp Leu Leu Asp Leu Ala Leu Lys Leu Pro His Val Lys Tyr
130                 135                 140
Ile Glu Glu Asp Ser Leu Val Phe Ala Gln Ser Ile Pro Trp Asn Leu
145                 150                 155                 160
Asp Arg Ile Ile Pro Ala Gly Arg Gln Ala Gln Glu Tyr Ser Ser Ser
                165                 170                 175
Arg Lys Val Pro Ser Gly Ser Gly Gln Val Glu Val Tyr Leu Leu Asp
            180                 185                 190
Thr Ser Ile Gln Ser Asp His Arg Glu Ile Glu Gly Arg Val Thr Val
            195                 200                 205
Thr Asp Phe Asn Ser Val Pro Glu Glu Asp Gly Thr Arg Phe His Arg
    210                 215                 220
Gln Ala Ser Lys Cys Asp Ser His Gly Thr His Leu Ala Gly Val Val
225                 230                 235                 240
Ser Gly Arg Asp Ala Gly Val Ala Lys Gly Thr Ile Leu His Gly Leu
                245                 250                 255
Arg Val Leu Asn Cys Gln Gly Lys Gly Ile Val Ser Gly Ile Leu Thr
            260                 265                 270
Gly Leu Glu Phe Ile Trp Lys Ser Gln Leu Met Gln Pro Ser Gly Pro
            275                 280                 285
Gln Val Val Leu Leu Pro Leu Ala Gly Arg Tyr Ser Arg Val Leu Asn
    290                 295                 300
Thr Ala Cys Gln His Leu Ala Arg Thr Gly Val Val Leu Val Ala Ala
305                 310                 315                 320
Ala Gly Asn Phe Arg Asp Asp Ala Cys Leu Tyr Ser Pro Ala Ser Ala
                325                 330                 335
Pro Glu Val Ile Thr Val Gly Ala Thr Asp Val Gln Asp Gln Pro Val
            340                 345                 350
Thr Leu Gly Thr Leu Gly Thr Asn Phe Gly Arg Cys Val Asp Leu Phe
            355                 360                 365
Ala Pro Gly Lys Asp Ile Ile Gly Ala Ser Ser Asp Cys Ser Ala Cys
    370                 375                 380
Phe Met Ser Gln Ser Gly Thr Ser Gln Ala Ala His Val Ala Gly
385                 390                 395                 400
```

FIG 1N$_1$

```
Ile Val Ala Met Met Leu Thr Leu Glu Pro Glu Leu Thr Leu Thr Glu
            405                 410                 415
Leu Arg Gln Arg Leu Ile His Phe Ser Thr Lys Asp Ala Ile Asn Met
            420                 425                 430
Ala Trp Phe Pro Glu Asp Gln Arg Val Leu Thr Pro Asn Leu Val Ala
            435                 440                 445
Thr Leu Pro Pro Ser Thr His Gly Thr Gly Gly Gln Leu Leu Cys Arg
    450                 455                 460
Thr Val Trp Ser Ala His Ser Gly Pro Thr Arg Ala Ala Thr Ala Thr
465                 470                 475                 480
Ala Arg Cys Ala Pro Gly Glu Glu Leu Leu Ser Cys Ser Ser Phe Ser
                485                 490                 495
Arg Ser Gly Arg Arg Arg Gly Asp Arg Ile Glu Ala Ala Gly Thr Gln
                500                 505                 510
Gln Val Cys Lys Ala Leu Asn Ala Phe Gly Gly Glu Gly Val Tyr Ala
            515                 520                 525
Val Ala Arg Cys Cys Leu Leu Pro Arg Ala Asn Cys Ser Ile His Thr
    530                 535                 540
Thr Pro Ala Ala Arg Thr Ser Leu Glu Thr His Ala His Cys His Gln
545                 550                 555                 560
Lys Asp His Val Leu Thr Gly Cys Ser Leu His Trp Glu Val Glu Gly
                565                 570                 575
Ile Gly Val Gln Pro Leu Ala Val Leu Arg Ser Arg His Gln Pro Gly
                580                 585                 590
Gln Cys Thr Gly His Arg Glu Ala Ser Val His Ala Ser Cys Cys His
            595                 600                 605
Ala Pro Gly Leu Glu Cys Lys Ile Lys Glu His Gly Ile Ser Gly Pro
    610                 615                 620
Ala Glu Gln Val Thr Val Ala Cys Glu Ala Gly Trp Thr Leu Thr Gly
625                 630                 635                 640
Cys Asn Val Leu Pro Gly Ala Phe Ile Thr Leu Gly Ala Tyr Ala Val
                645                 650                 655
Asp Asn Thr Cys Val Ala Arg Ser Arg Val Thr Asp Thr Ala Gly Arg
                660                 665                 670
Thr Gly Glu Glu Ala Thr Val Ala Ala Ile Cys Cys Arg Asn Arg
            675                 680                 685
Pro Ser Ala Lys Ala Ser Trp Val His Gln
690                 695
```

SEQ ID NO: 26

FIG 1N₂

Mus musculus PCSK9

```
  Met Gly Thr His Cys Ser Ala Trp Leu Arg Trp Pro Leu Leu Pro Leu
  1               5                   10                  15
  Leu Pro Pro Leu Leu Leu Leu Leu Leu Leu Leu Cys Pro Thr Gly Ala
              20                  25                  30
  Gly Ala Gln Asp Glu Asp Gly Asp Tyr Glu Glu Leu Met Leu Ala Leu
          35                  40                  45
  Pro Ser Gln Glu Asp Gly Leu Ala Asp Glu Ala Ala His Val Ala Thr
      50                  55                  60
  Ala Thr Phe Arg Arg Cys Ser Lys Glu Ala Trp Arg Leu Pro Gly Thr
  65              70                  75                  80
  Tyr Ile Val Val Leu Met Glu Glu Thr Gln Arg Leu Gln Ile Glu Gln
                  85                  90                  95
  Thr Ala His Arg Leu Gln Thr Arg Ala Ala Arg Arg Gly Tyr Val Ile
              100                 105                 110
  Lys Val Leu His Ile Phe Tyr Asp Leu Phe Pro Gly Phe Leu Val Lys
              115                 120                 125
  Met Ser Ser Asp Leu Leu Gly Leu Ala Leu Lys Leu Pro His Val Glu
          130                 135                 140
  Tyr Ile Glu Glu Asp Ser Phe Val Phe Ala Gln Ser Ile Pro Trp Asn
  145                 150                 155                 160
  Leu Arg Ile Ile Pro Ala Trp His Gln Thr Glu Glu Asp Arg Ser Pro
                  165                 170                 175
  Asp Gly Ser Ser Gln Val Glu Val Tyr Leu Leu Asp Thr Ser Ile Gln
              180                 185                 190
  Gly Ala His Arg Glu Ile Glu Gly Arg Val Thr Ile Thr Asp Phe Asn
              195                 200                 205
  Ser Val Pro Glu Glu Asp Gly Thr Arg Phe His Arg Gln Ala Ser Lys
          210                 215                 220
  Cys Asp Ser His Gly Thr His Leu Ala Gly Val Val Ser Gly Arg Asp
  225                 230                 235                 240
  Ala Gly Val Ala Lys Gly Thr Ser Leu His Ser Leu Arg Val Leu Asn
                  245                 250                 255
  Cys Gln Gly Lys Gly Thr Val Ser Gly Thr Leu Ile Gly Leu Glu Phe
              260                 265                 270
  Ile Arg Lys Ser Gln Leu Ile Gln Pro Ser Pro Leu Val Val Leu Pro
              275                 280                 285
  Leu Ala Gly Gly Tyr Ser Arg Ile Leu Asn Ala Ala Cys Arg His Leu
          290                 295                 300
  Ala Arg Thr Gly Val Val Leu Val Ala Ala Ala Gly Asn Phe Arg Asp
  305                 310                 315                 320
  Asp Ala Cys Leu Tyr Ser Pro Ala Ser Ala Pro Glu Val Ile Thr Val
                  325                 330                 335
  Gly Ala Thr Asn Ala Gln Asp Gln Pro Val Thr Leu Gly Thr Leu Gly
              340                 345                 350
  Thr Asn Phe Gly Arg Cys Val Asp Leu Phe Ala Pro Gly Lys Asp Ile
              355                 360                 365
  Ile Gly Ala Ser Ser Asp Cys Ser Thr Cys Phe Met Ser Gln Ser Gly
          370                 375                 380
  Thr Ser Gln Ala Ala Ala His Val Ala Gly Ile Val Ala Arg Met Leu
  385                 390                 395                 400
```

FIG 10₁

```
Ser Arg Glu Pro Thr Leu Thr Leu Ala Leu Arg Gln Arg Ile His Phe
                405                 410                 415
Ser Thr Lys Asp Val Ile Asn Met Ala Trp Phe Pro Glu Asp Gln Gln
            420                 425                 430
Val Leu Thr Pro Asn Leu Val Ala Thr Leu Pro Pro Ser Thr His Glu
            435                 440                 445
Thr Gly Gly Gln Leu Leu Cys Arg Thr Val Trp Ser Ala His Ser Gly
    450                 455                 460
Pro Thr Arg Thr Ala Thr Ala Thr Ala Arg Cys Ala Pro Glu Glu Glu
465                 470                 475                 480
Leu Leu Ser Cys Ser Ser Phe Ser Arg Ser Gly Arg Arg Arg Gly Asp
                485                 490                 495
Arg Ile Glu Ala Ile Gly Gly Gln Gln Val Cys Lys Ala Leu Asn Ala
                500                 505                 510
Phe Gly Gly Glu Gly Val Tyr Ala Val Ala Arg Cys Cys Leu Val Pro
            515                 520                 525
His Ala Asn Cys Ser Ile His Asn Pro Ala Ala Ala Gly Leu Glu Thr
    530                 535                 540
His Val His Cys His Gln Lys Asp His Val Leu Thr Gly Cys Ser Phe
545                 550                 555                 560
His Trp Glu Val Glu Asp Leu Ser Val Arg Arg Gln Pro Ala Leu Arg
                565                 570                 575
Ser Arg Arg Gln Pro Gly Gln Cys Val Gly His Gln Ala Ala Ser Val
                580                 585                 590
Tyr Ala Ser Cys Cys His Ala Pro Gly Leu Glu Cys Lys Ile Lys Glu
            595                 600                 605
His Gly Ile Ser Gly Ser Ser Glu Gln Val Thr Val Ala Cys Glu Ala
    610                 615                 620
Gly Trp Thr Leu Thr Gly Cys Asn Val Leu Pro Gly Ala Ser Leu Thr
625                 630                 635                 640
Leu Gly Ala Tyr Ser Val Asp Asn Leu Cys Val Ala Arg Val His Asp
                645                 650                 655
Thr Ala Arg Ala Asp Arg Thr Gly Glu Thr Val Ala Ala Ala Ile Cys
                660                 665                 670
Cys Arg Ser Arg Pro Ser Ala Lys Ala Ser Trp Val Gln
                675                 680                 685
```

SEQ ID NO: 27

Macaca fascicularis PCSK9

```
Met Gly Thr Val Ser Ser Arg Arg Ser Trp Trp Pro Leu Pro Leu Pro
 1               5                   10                  15
Leu Leu Leu Leu Leu Leu Leu Gly Pro Ala Gly Ala Arg Ala Gln Glu
            20                  25                  30
Asp Glu Asp Gly Asp Tyr Glu Glu Leu Val Leu Ala Leu Arg Ser Glu
        35                  40                  45
Glu Asp Gly Leu Ala Asp Ala Pro Glu His Gly Ala Thr Ala Thr Phe
    50                  55                  60
His Arg Cys Ala Lys Asp Pro Trp Arg Leu Pro Gly Thr Tyr Val Val
65                  70                  75                      80
Val Leu Lys Glu Glu Thr His Arg Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His His Leu Leu Pro Gly Phe Leu Val Lys Met Ser Gly
        115                 120                 125
Asp Leu Leu Glu Leu Ala Leu Lys Leu Pro His Val Asp Tyr Ile Glu
    130                 135                 140
Glu Asp Ser Ser Val Phe Ala Gln Ser Ile Pro Trp Asn Glu Arg Ile
145                 150                 155                 160
Thr Pro Ala Arg Tyr Arg Ala Asp Glu Tyr Gln Pro Pro Lys Gly Gly
                165                 170                 175
Ser Leu Val Glu Val Tyr Leu Leu Asp Thr Ser Ile Gln Ser Asp His
            180                 185                 190
Arg Glu Ile Glu Gly Arg Val Met Val Thr Asp Phe Glu Ser Val Pro
        195                 200                 205
Glu Glu Asp Gly Thr Arg Phe His Arg Gln Ala Ser Lys Cys Asp Ser
    210                 215                 220
His Gly Thr His Leu Ala Gly Val Val Ser Gly Arg Asp Ala Gly Val
225                 230                 235                 240
Ala Lys Gly Ala Gly Leu Arg Ser Leu Arg Val Leu Asn Cys Gln Gly
                245                 250                 255
Lys Gly Thr Val Ser Gly Thr Leu Ile Gly Leu Glu Phe Ile Arg Lys
            260                 265                 270
Ser Gln Leu Val Gln Pro Val Pro Leu Val Val Leu Pro Leu Ala Gly
        275                 280                 285
Gly Tyr Ser Arg Val Phe Asn Ala Ala Cys Gln Arg Leu Ala Arg Ala
    290                 295                 300
Gly Val Val Leu Val Thr Ala Ala Gly Asn Phe Arg Asp Asp Ala Cys
305                 310                 315                 320
Leu Tyr Ser Pro Ala Ser Ala Pro Glu Val Ile Thr Val Gly Ala Thr
                325                 330                 335
Asn Ala Gln Asp Gln Pro Val Thr Leu Gly Thr Leu Gly Thr Asn Phe
            340                 345                 350
Gly Arg Cys Val Asp Leu Phe Ala Pro Gly Glu Asp Ile Ile Gly Ala
        355                 360                 365
Ser Ser Asp Cys Ser Thr Cys Phe Val Ser Arg Ser Gly Thr Ser Gln
    370                 375                 380
Ala Ala Ala His Val Ala Gly Ile Ala Ala Met Met Leu Ser Ala Glu
385                 390                 395                 400
```

FIG 1P₁

```
Pro Glu Leu Thr Leu Ala Leu Arg Gln Leu Ile His Phe Ser Ala Lys
                405                 410                 415
Asp Val Ile Asn Glu Ala Trp Phe Pro Glu Asp Gln Arg Val Leu Thr
            420                 425                 430
Pro Asn Leu Val Ala Ala Leu Pro Pro Ser Thr His Arg Ala Gly Trp
        435                 440                 445
Gln Leu Phe Cys Arg Thr Val Trp Ser Ala His Ser Gly Pro Thr Arg
    450                 455                 460
Met Ala Thr Ala Val Ala Arg Cys Ala Gln Asp Glu Glu Leu Leu Ser
465                 470                 475                 480
Cys Ser Ser Phe Ser Arg Ser Gly Lys Arg Arg Gly Glu Arg Ile Glu
                485                 490                 495
Ala Gln Gly Gly Lys Arg Val Cys Arg Ala His Asn Ala Phe Gly Gly
            500                 505                 510
Glu Gly Val Tyr Ala Ile Ala Arg Cys Cys Leu Leu Pro Gln Val Asn
        515                 520                 525
Cys Ser Val His Thr Pro Pro Gly Ala Ser Met Gly Thr Arg Val His
    530                 535                 540
Cys His Gln Gln Gly His Val Leu Thr Gly Cys Ser Ser His Trp Glu
545                 550                 555                 560
Val Glu Asp Leu Gly Thr His Lys Pro Pro Val Leu Arg Pro Arg Gly
                565                 570                 575
Gln Pro Asn Gln Cys Val Gly His Arg Glu Ala Ser Ile His Ala Ser
            580                 585                 590
Cys Cys His Ala Pro Gly Leu Glu Cys Lys Val Arg Glu His Gly Ile
        595                 600                 605
Pro Ala Pro Gln Glu Gln Val Ile Val Ala Cys Glu Asp Gly Trp Thr
    610                 615                 620
Leu Thr Gly Cys Ser Ala Leu Pro Gly Thr Ser His Val Leu Gly Ala
625                 630                 635                 640
Tyr Ala Val Asp Asn Thr Cys Val Val Arg Ser Arg Asp Val Ser Thr
                645                 650                 655
Thr Gly Ser Thr Glu Ala Val Ala Ala Val Ala Ile Cys Cys Arg Ser
            660                 665                 670
Arg His Leu Val Gln Ala Ser Gln Glu Leu Gln
        675                 680

SEQ ID NO: 28
```

FIG 1P$_2$

Rattus norvegicus PCSK9

```
Met Gly Ile Arg Cys Ser Thr Trp Leu Arg Trp Pro Leu Ser Pro Gln
 1               5                  10                 15
Leu Leu Leu Leu Leu Leu Leu Cys Pro Thr Gly Ser Arg Ala Gln Asp
            20                  25                 30
Glu Asp Gly Asp Tyr Glu Glu Leu Met Leu Ala Leu Pro Ser Gln Glu
        35                  40                 45
Asp Ser Leu Val Asp Glu Ala Ser His Val Ala Thr Ala Thr Phe Arg
    50                  55                 60
Arg Cys Ser Lys Glu Ala Trp Arg Leu Pro Gly Thr Tyr Val Val Val
65                  70                  75                      80
Leu Met Glu Glu Thr Gln Arg Leu Gln Val Glu Gln Thr Ala His Arg
                85                  90                  95
Leu Gln Thr Trp Ala Ala Arg Arg Gly Tyr Val Ile Lys Val Leu His
            100                 105                110
Val Phe Tyr Asp Leu Phe Pro Gly Phe Leu Val Lys Met Ser Ser Asp
        115                 120                125
Leu Leu Gly Leu Ala Leu Lys Leu Pro His Val Glu Tyr Ile Glu Glu
    130                 135                140
Asp Ser Leu Val Phe Ala Gln Ser Ile Pro Trp Asn Leu Glu Arg Ile
145                 150                 155                    160
Ile Pro Ala Trp Gln Gln Thr Glu Glu Asp Ser Ser Pro Asp Gly Ser
                165                 170                175
Ser Gln Val Glu Val Tyr Leu Leu Asp Thr Ser Ile Gln Ser Gly His
            180                 185                190
Arg Glu Ile Glu Gly Arg Val Thr Ile Thr Asp Phe Asn Ser Val Pro
        195                 200                205
Glu Glu Asp Gly Thr Arg Phe His Arg Gln Ala Ser Lys Cys Asp Ser
    210                 215                220
His Gly Thr His Leu Ala Gly Val Val Ser Gly Arg Asp Ala Gly Val
225                 230                 235                    240
Ala Lys Gly Thr Ser Leu His Ser Leu Arg Val Leu Asn Cys Gln Gly
                245                 250                255
Lys Gly Thr Val Ser Gly Thr Leu Ile Gly Leu Glu Phe Ile Arg Lys
            260                 265                270
Ser Gln Leu Ile Gln Pro Ser Gly Pro Leu Val Val Leu Leu Pro Leu
        275                 280                285
Ala Gly Gly Tyr Ser Arg Ile Leu Asn Thr Ala Cys Gln Arg Leu Ala
    290                 295                300
Arg Thr Gly Val Val Leu Val Ala Ala Ala Gly Asn Phe Arg Asp Asp
305                 310                 315                    320
Ala Cys Leu Tyr Ser Pro Ala Ser Ala Pro Glu Val Ile Thr Val Gly
                325                 330                335
Ala Thr Asn Ala Gln Asp Gln Pro Val Thr Leu Gly Thr Leu Gly Thr
            340                 345                350
Asn Phe Gly Arg Cys Val Asp Leu Phe Ala Pro Gly Lys Asp Ile Ile
        355                 360                365
Gly Ala Ser Ser Asp Cys Ser Thr Cys Tyr Met Ser Gln Ser Gly Thr
    370                 375                380
Ser Gln Ala Ala Ala His Val Ala Gly Ile Val Ala Met Met Leu Asn
385                 390                 395                    400
```

FIG 1Q₁

```
Arg Asp Pro Ala Leu Thr Leu Ala Glu Leu Arg Gln Arg Leu Ile Leu
                405                 410                 415
Phe Ser Thr Lys Asp Val Ile Asn Met Ala Trp Phe Pro Glu Asp Gln
            420                 425                 430
Arg Val Leu Thr Pro Asn Arg Val Ala Thr Leu Pro Pro Ser Thr Gln
            435                 440                 445
Glu Thr Gly Gly Gln Leu Leu Cys Arg Thr Val Trp Ser Ala His Ser
        450                 455                 460
Gly Pro Thr Arg Thr Ala Thr Ala Thr Ala Arg Cys Ala Pro Glu Glu
465                 470                 475                 480
Glu Leu Leu Ser Cys Ser Ser Phe Ser Arg Ser Gly Arg Arg Arg Gly
                485                 490                 495
Asp Arg Ile Glu Ala Ile Gly Gly Gln Gln Val Cys Lys Ala Leu Asn
                500                 505                 510
Ala Phe Gly Gly Glu Gly Val Tyr Ala Val Ala Arg Cys Cys Leu Leu
            515                 520                 525
Pro Arg Val Asn Cys Ser Ile His Asn Thr Pro Ala Ala Arg Ala Gly
        530                 535                 540
Pro Gln Thr Pro Val His Cys His Gln Lys Asp His Val Leu Thr Gly
545                 550                 555                 560
Cys Ser Phe His Trp Glu Val Glu Asn Leu Arg Ala Gln Gln Gln Pro
                565                 570                 575
Leu Leu Arg Ser Arg His Gln Pro Gly Gln Cys Val Gly His Gln Glu
                580                 585                 590
Ala Ser Val His Ala Ser Cys Cys His Ala Pro Gly Leu Glu Cys Lys
            595                 600                 605
Ile Lys Glu His Gly Ile Ala Gly Pro Ala Glu Gln Val Thr Val Ala
        610                 615                 620
Cys Glu Ala Gly Trp Thr Leu Thr Gly Cys Asn Val Leu Pro Gly Ala
625                 630                 635                 640
Ser Leu Pro Leu Gly Ala Tyr Ser Val Asp Asn Val Cys Val Ala Arg
                645                 650                 655
Ile Arg Asp Ala Gly Arg Ala Asp Arg Thr Ser Glu Glu Ala Thr Val
                660                 665                 670
Ala Ala Ala Ile Cys Cys Arg Ser Arg Pro Ser Ala Lys Ala Ser Trp
            675                 680                 685
Val His Gln
        690

SEQ ID NO: 29
```

FIG 1Q₂

Consensus sequence of PCSK9

```
Met Gly Thr Xaa Cys Ser Ala Arg Ser Trp Trp Pro Leu Xaa Xaa Xaa
1               5                   10                  15
Xaa Xaa Pro Leu Leu Leu Leu Leu Leu Leu Leu Pro Ala Gly Ala Ala
            20                  25                  30
Ala Ala Gln Asp Glu Asp Gly Asp Tyr Glu Glu Leu Met Leu Ala Leu
            35                  40                  45
Pro Ser Gln Glu Asp Gly Leu Ala Asp Glu Ala Glu His Val Xaa Xaa
    50                  55                  60
Xaa Ala Thr Ala Thr Phe His Arg Cys Ser Lys Asp Ala Trp Arg Leu
65              70                  75                      80
Pro Gly Thr Tyr Val Val Val Leu Lys Glu Glu Thr Gln Arg Leu Gln
                85                  90                  95
Ser Glu Gln Thr Ala His Arg Leu Gln Thr Gln Ala Ala Arg Arg Gly
            100                 105                 110
Tyr Val Thr Lys Ile Leu His Val Phe His Asp Leu Leu Pro Gly Phe
            115                 120                 125
Leu Val Lys Met Ser Ser Asp Leu Leu Asp Leu Ala Leu Lys Leu Pro
    130                 135                 140
His Val Asp Tyr Ile Glu Glu Asp Ser Ser Val Phe Ala Gln Ser Ile
145                 150                 155                 160
Pro Trp Asn Leu Glu Arg Ile Ile Pro Ala Arg His Gln Ala Asp Glu
                165                 170                 175
Tyr Ser Ser Xaa Xaa Xaa Xaa Pro Asp Gly Ser Ser Gln Val Glu Val
            180                 185                 190
Tyr Leu Leu Asp Thr Ser Ile Gln Ser Asp His Arg Glu Ile Glu Gly
        195                 200                 205
Arg Val Thr Val Thr Asp Phe Asn Ser Val Pro Glu Glu Asp Gly Thr
    210                 215                 220
Arg Phe His Arg Gln Ala Ser Lys Cys Asp Ser His Gly Thr His Leu
225                 230                 235                 240
Ala Gly Val Val Ser Gly Arg Asp Ala Gly Val Ala Lys Gly Thr Ser
            245                 250                 255
Leu Arg Ser Leu Arg Val Leu Asn Cys Gln Gly Lys Gly Thr Val Ser
            260                 265                 270
Gly Thr Leu Ile Gly Leu Glu Phe Ile Arg Lys Ser Gln Leu Ile Gln
        275                 280                 285
Pro Val Gly Pro Leu Val Val Leu Leu Pro Leu Ala Gly Gly Tyr Ser
    290                 295                 300
Arg Val Leu Asn Ala Ala Cys Gln Arg Leu Ala Arg Thr Gly Val Val
305                 310                 315                 320
Leu Val Ala Ala Ala Gly Asn Phe Arg Asp Asp Ala Cys Leu Tyr Ser
            325                 330                 335
Pro Ala Ser Ala Pro Glu Val Ile Thr Val Gly Ala Thr Asn Ala Gln
            340                 345                 350
Asp Gln Pro Val Thr Leu Gly Thr Leu Gly Thr Asn Phe Gly Arg Cys
        355                 360                 365
Val Asp Leu Phe Ala Pro Gly Lys Asp Ile Ile Gly Ala Ser Ser Asp
    370                 375                 380
Cys Ser Thr Cys Phe Met Ser Gln Ser Gly Thr Ser Gln Ala Ala Ala
385                 390                 395                 400
```

FIG 1R$_1$

```
His Val Ala Gly Ile Val Ala Met Met Leu Ser Ala Glu Pro Glu Leu
                405                     410                 415
Thr Leu Ala Glu Leu Arg Gln Arg Leu Ile His Phe Ser Thr Lys Asp
            420                 425                 430
Val Ile Asn Met Ala Trp Phe Pro Glu Asp Gln Arg Val Leu Thr Pro
                435                 440                 445
Asn Leu Val Ala Thr Leu Pro Pro Ser Thr His Gly Thr Gly Gly Gln
    450                 455                 460
Leu Leu Cys Arg Thr Val Trp Ser Ala His Ser Gly Pro Thr Arg Thr
465                 470                 475                     480
Ala Thr Ala Thr Ala Arg Cys Ala Pro Asp Glu Glu Leu Leu Ser Cys
                485                 490                 495
Ser Ser Phe Ser Arg Ser Gly Lys Arg Arg Gly Asp Arg Ile Glu Ala
                500                 505                 510
Ile Gly Gly Gln Gln Val Cys Lys Ala Leu Asn Ala Phe Gly Gly Glu
            515                 520                 525
Gly Val Tyr Ala Val Ala Arg Cys Cys Leu Leu Pro Arg Ala Asn Cys
    530                 535                 540
Ser Ile His Thr Thr Pro Ala Ala Arg Ala Ser Met Glu Thr Arg Val
545                 550                 555                     560
His Cys His Gln Lys Asp His Val Leu Thr Gly Cys Ser Ser His Trp
                565                 570                 575
Glu Val Glu Asp Leu Gly Xaa Xaa Lys Xaa Pro Val Leu Arg Ser Arg
                580                 585                 590
Gly Gln Pro Gly Gln Cys Val Gly His Arg Glu Ala Ser Val His Ala
            595                 600                 605
Ser Cys Cys His Ala Pro Gly Leu Glu Cys Lys Ile Lys Glu His Gly
    610                 615                 620
Ile Pro Gly Pro Ala Glu Gln Val Thr Val Ala Cys Glu Ala Gly Trp
625                 630                 635                     640
Thr Leu Thr Gly Cys Ser Val Leu Pro Gly Ala Ser Leu Val Leu Gly
                645                 650                 655
Ala Tyr Ala Val Asp Asn Thr Cys Val Val Arg Ser Arg Asp Val Ser
                660                 665                 670
Thr Ala Gly Arg Thr Ser Glu Glu Ala Thr Val Ala Ala Ala Ile Cys
            675                 680                 685
Cys Arg Ser Arg Pro Ser Ala Gln Ala Ser Trp Val Xaa Gln
    690                 695                 700
```

SEQ ID NO: 30

Xaa = Any Amino Acid or No Amino Acid

FIG 1R₂

Homo sapiens PCSK9

```
Met Gly Thr Val Ser Ser Arg Arg Ser Trp Trp Pro Leu Pro Leu Leu
 1               5                   10                  15
Leu Leu Leu Leu Leu Leu Leu Gly Pro Ala Gly Ala Arg Ala Gln Glu
            20                  25                  30
Asp Glu Asp Gly Asp Tyr Glu Glu Leu Val Leu Ala Leu Arg Ser Glu
        35                  40                  45
Glu Asp Gly Leu Ala Glu Ala Pro Glu His Gly Thr Thr Ala Thr Phe
    50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His Leu Leu Pro Gly Phe Leu Val Lys Met Ser Gly Asp
        115                 120                 125
Leu Leu Glu Leu Ala Leu Lys Leu Pro His Val Asp Tyr Ile Glu Glu
    130                 135                 140
Asp Ser Ser Val Phe Ala Gln Ser Ile Pro Trp Asn Leu Glu Arg Ile
145                 150                 155                 160
Thr Pro Pro Arg Tyr Arg Ala Asp Glu Tyr Gln Pro Pro Asp Gly Gly
                165                 170                 175
Ser Leu Val Glu Val Tyr Leu Leu Asp Thr Ser Ile Gln Ser Asp His
            180                 185                 190
Arg Glu Ile Glu Gly Arg Val Met Val Thr Asp Phe Glu Asn Val Pro
        195                 200                 205
Glu Glu Asp Gly Thr Arg Phe His Arg Gln Ala Ser Lys Cys Asp Ser
    210                 215                 220
His Gly Thr His Leu Ala Gly Val Val Ser Gly Arg Asp Ala Gly Val
225                 230                 235                 240
Ala Lys Gly Ala Ser Met Arg Ser Leu Arg Val Leu Asn Cys Gln Gly
                245                 250                 255
Lys Gly Thr Val Ser Gly Thr Leu Ile Gly Leu Glu Phe Ile Arg Lys
            260                 265                 270
Ser Gln Leu Val Gln Pro Val Pro Leu Val Val Leu Leu Pro Leu Ala
        275                 280                 285
Gly Gly Tyr Ser Arg Val Leu Asn Ala Ala Cys Gln Arg Leu Ala Arg
    290                 295                 300
Ala Gly Val Val Leu Val Thr Ala Ala Gly Asn Phe Arg Asp Asp Ala
305                 310                 315                 320
Cys Leu Tyr Ser Pro Ala Ser Ala Pro Glu Val Ile Thr Val Gly Ala
                325                 330                 335
Thr Asn Ala Gln Asp Gln Pro Val Thr Leu Gly Thr Leu Gly Thr Asn
            340                 345                 350
Phe Gly Arg Cys Val Asp Leu Phe Ala Pro Gly Glu Asp Ile Ile Gly
        355                 360                 365
Ala Ser Ser Asp Cys Ser Thr Cys Phe Val Ser Gln Ser Gly Thr Ser
    370                 375                 380
Gln Ala Ala Ala His Val Ala Gly Ile Ala Ala Met Met Leu Ser Ala
385                 390                 395                 400
```

FIG 1S$_1$

```
Glu Pro Glu Leu Thr Leu Ala Glu Leu Arg Gln Leu Ile His Phe Ser
            405                 410                 415
Ala Lys Asp Val Ile Asn Glu Ala Trp Phe Pro Glu Asp Gln Arg Val
            420                 425                 430
Leu Thr Pro Asn Leu Val Ala Ala Leu Pro Pro Ser Thr His Gly Ala
            435                 440                 445
Gly Trp Gln Leu Phe Cys Arg Thr Val Trp Ser Ala His Ser Gly Pro
        450                 455                 460
Thr Arg Met Ala Thr Ala Ile Ala Arg Cys Ala Pro Asp Glu Glu Leu
465                 470                 475                 480
Leu Ser Cys Ser Ser Phe Ser Arg Ser Gly Lys Arg Arg Gly Glu Arg
                485                 490                 495
Met Glu Ala Gln Gly Gly Lys Leu Val Cys Arg Ala His Asn Ala Phe
            500                 505                 510
Gly Gly Glu Gly Val Tyr Ala Ile Ala Arg Cys Cys Leu Leu Pro Gln
            515                 520                 525
Ala Asn Cys Ser Val His Thr Ala Pro Pro Ala Glu Ala Ser Met Gly
            530                 535                 540
Thr Arg Val His Cys His Gln Gln Gly His Val Leu Thr Gly Cys Ser
545                 550                 555                 560
Ser His Trp Glu Val Glu Asp Leu Gly Thr His Lys Pro Pro Val Leu
                565                 570                 575
Arg Pro Arg Gly Gln Pro Asn Gln Cys Val Gly His Arg Glu Ala Ser
            580                 585                 590
Ile His Ala Ser Cys Cys His Ala Pro Gly Leu Glu Cys Lys Val Lys
            595                 600                 605
Glu His Gly Ile Pro Ala Pro Gln Glu Gln Val Thr Val Ala Cys Glu
        610                 615                 620
Glu Gly Trp Thr Leu Thr Gly Cys Ser Ala Leu Pro Gly Thr Ser His
625                 630                 635                 640
Val Leu Gly Ala Tyr Ala Val Asp Asn Thr Cys Val Val Arg Ser Arg
                645                 650                 655
Asp Val Ser Thr Thr Gly Ser Thr Ser Glu Glu Ala Val Thr Ala Val
            660                 665                 670
Ala Ile Cys Cys Arg Ser Arg His Leu Ala Gln Ala Ser Gln Glu Leu
            675                 680                 685
Gln
```

SEQ ID NO: 31

FIG 1S$_2$

```
                         SEQUENCE LISTING

<160> NUMBER OF SEQ ID NOS: 31

<210> SEQ ID NO 1
<211> LENGTH: 662
<212> TYPE: PRT
<213> ORGANISM: Homo sapiens

<400> SEQUENCE: 1

Gln Glu Asp Glu Asp Gly Asp Tyr Glu Glu Leu Val Leu Ala Leu Arg
  1               5                  10                  15

Ser Glu Glu Asp Gly Leu Ala Glu Ala Pro Glu His Gly Thr Thr Ala
             20                  25                  30

Thr Phe His Arg Cys Ala Lys Asp Pro Trp Arg Leu Pro Gly Thr Tyr
         35                  40                  45

Val Val Val Leu Lys Glu Glu Thr His Leu Ser Gln Ser Glu Arg Thr
     50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                 85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270
```

-continued

```
Arg Leu Ala Arg Ala Gly Val Val Leu Val Thr Ala Ala Gly Asn Phe
    275                 280                 285
Arg Asp Asp Ala Cys Leu Tyr Ser Pro Ala Ser Ala Pro Glu Val Ile
    290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
                340                 345                 350
Ser Gly Thr Ser Gln Ala Ala His Val Ala Gly Ile Ala Ala Met
                355                 360                 365
Met Leu Ser Ala Glu Pro Glu Leu Thr Leu Ala Glu Leu Arg Gln Arg
    370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
                420                 425                 430
Ala His Ser Gly Pro Thr Arg Met Ala Thr Ala Ile Ala Arg Cys Ala
    435                 440                 445
Pro Asp Glu Glu Leu Leu Ser Cys Ser Ser Phe Ser Arg Ser Gly Lys
    450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
                500                 505                 510
Glu Ala Ser Met Gly Thr Arg Val His Cys His Gln Gln Gly His Val
    515                 520                 525
Leu Thr Gly Cys Ser Ser His Trp Glu Val Glu Asp Leu Gly Thr His
    530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Gln Gly Gln Val
                580                 585                 590
Thr Val Ala Cys Glu Glu Gly Trp Thr Leu Thr Gly Cys Ser Ala Leu
    595                 600                 605
Pro Gly Thr Ser His Val Leu Gly Ala Tyr Ala Val Asp Asn Thr Cys
    610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln
            660
```

```
<210> SEQ ID NO 2
<211> LENGTH: 2076
<212> TYPE: DNA
<213> ORGANISM: Homo sapiens

<400> SEQUENCE: 2
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgctc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480
attacccctc gcggtaccg gcggatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg cagggggtgg tcagcggccg ggatgccggc     720
gtggccaagg tgccagcat gcgcagcctg cgcgtgctca actgccaagg gaagggcacg     780
gttagcggca ccctcatagg cctggagttt attcggaaaa gccagctggt ccagcctgtg     840
gggccactgg tggtgctgct gccccctggcg ggtgggtaca gccgcgtcct caacgccgcc     900
tgccagcgcc tggcgagggc tggggtcgtg ctggtcaccg ctgccggcaa cttccgggac     960
gatgcctgcc tctactcccc agcctcagct cccgaggtca tcacagttgg ggccaccaat    1020
gcccaggacc agccggtgac cctggggact ttggggacca ctttggccg ctgtgtggac    1080 ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgcccccccag cacccatggg gcaggttggc agctgttttg caggactgtg    1380
tggtcagcac actcgggggcc tacacggatg gccacagcca tcgcccgctg cgccccagat    1440
gaggagctgc tgagctgctc cagtttctcc aggagtggga gcggcgggg cgagcgcatg    1500 gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gaccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggggagg ccagcatcca cgcttcctgc    1800
tgccatgccc caggtctgga atgcaaagtc aaggagcatg gaatcccggc ccctcagggg    1860
caggtgaccg tggcctgcga ggagggctgg accctgactg gctgcagcgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccag                              2076
```

<210> SEQ ID NO 3
<211> LENGTH: 692
<212> TYPE: PRT
<213> ORGANISM: Homo sapiens

<400> SEQUENCE: 3

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
        405                 410                 415

His Phe Ser Ala Lys Asp Val Ile Asn Glu Ala Trp Phe Pro Glu Asp
        420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Gly Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 4
<211> LENGTH: 692
<212> TYPE: PRT
<213> ORGANISM: Cavia porcellus

<400> SEQUENCE: 4

Met Arg Thr Arg Gly Pro Ala Pro Ala Trp Trp Pro Met Leu Leu Leu
1               5                   10                  15

Leu Met Leu Gly Pro Ala Pro Ala Gly Ala Gln Ala Arg Asp Ser Glu
            20                  25                  30

Asp Gly Asp His Glu Gly Leu Ala Phe Ala Phe Pro Glu Glu Asp
        35                  40                  45

Gly Pro Ala Glu Ala Ala Pro His Val Pro Thr Ala Pro Phe His Arg
50                  55                  60

```
Cys Ser Lys Asp Ala Trp Arg Leu Pro Gly Thr Tyr Leu Val Val Leu
 65                  70                  75                  80

Lys Glu Gly Thr His Arg Gly Gln Thr Lys His Thr Ala His Arg Leu
                 85                  90                  95

Gln Ala Lys Ala Ala Arg Arg Gly Tyr Val Thr Thr Val Leu His Leu
            100                 105                 110

Phe His His Leu Val Pro Gly Phe Leu Val Arg Met Ser Gly Asp Leu
        115                 120                 125

Leu Asp Met Ala Leu Arg Leu Pro Leu Val Gln Tyr Ile Glu Glu Asp
    130                 135                 140

Ser Ser Val Phe Ala Gln Ser Val Pro Trp Asn Leu Glu Arg Ile Leu
145                 150                 155                 160

Pro Val Arg His Gln Ala Lys Glu Tyr Ser Ala Pro Ser His Pro Val
                165                 170                 175

Thr Val Tyr Leu Leu Asp Thr Ser Ile Gln Ser Gly His Arg Glu Ile
            180                 185                 190

Gln Gly Arg Ile Thr Val Thr Asp Phe Glu Ser Val Pro Gln Glu Asp
        195                 200                 205

Gly Thr Arg Phe His Arg Gln Ala Ser Lys Cys Asp Ser His Gly Thr
    210                 215                 220

His Leu Ala Gly Val Val Ser Gly Arg Asp Ala Gly Val Ala Lys Gly
225                 230                 235                 240

Ala Gly Leu Arg Ser Leu Arg Val Leu Asn Cys Gln Gly Arg Gly Thr
                245                 250                 255

Val Ser Ser Thr Leu Arg Gly Leu Glu Phe Ile Arg Lys Ser Gln Leu
            260                 265                 270

Ala Gln Pro Val Glu Pro Leu Val Val Leu Pro Leu Ala Gly Gly Gly
        275                 280                 285

Tyr Ser Arg Thr Leu Asn Ala Ala Cys His Leu Leu Ala Arg Ala Gly
    290                 295                 300

Val Val Leu Val Ala Ala Gly Asn Phe Arg Asp Asp Ala Cys Leu
305                 310                 315                 320

Tyr Ser Pro Ala Ser Ala Pro Glu Val Ile Thr Val Gly Ala Thr Asn
                325                 330                 335

Ala Gln Asp Gln Pro Val Thr Leu Gly Thr Leu Gly Thr Asn Phe Gly
            340                 345                 350

Arg Cys Val Asp Leu Phe Ala Pro Gly Glu Asp Ile Ile Gly Ala Ser
        355                 360                 365

Ser Asp Cys Ser Thr Cys Phe Val Ser Arg Ser Gly Thr Ser Gln Ala
    370                 375                 380

Ala Ala His Val Ala Gly Ile Val Thr Met Met Leu Thr Ala Gln Pro
385                 390                 395                 400

Lys Leu Thr Leu Ala Glu Leu Trp Gln Arg Leu Ile His Phe Ala Ala
                405                 410                 415

Lys Asp Val Ile Asn Glu Ala Trp Phe Pro Glu Asp Gln Arg Val Leu
            420                 425                 430

Thr Pro Asn Leu Val Ala Thr Leu Pro Pro Ser Thr Arg Gly Ala Gly
        435                 440                 445

Gly Arg Leu Leu Cys Arg Thr Val Trp Ser Ala Arg Ser Gly Pro Arg
    450                 455                 460

His Thr Ala Thr Ala Leu Ala His Cys Thr Pro Gly Glu Glu Leu Leu
465                 470                 475                 480
```

Ser Cys Ser Ser Phe Ser Arg Ser Gly Lys Arg Lys Gly Glu Arg Ile
            485                 490                 495

Glu Val Leu Arg Gly Arg Val Cys Val Ala Tyr Asn Ala Phe Gly
        500                 505                 510

Gly Lys Gly Val His Ala Val Ala Arg Cys Cys Leu Leu Pro Arg Ala
        515                 520                 525

Asn Cys Ser Leu His Thr Ala Pro Ala Arg Ala Gly Met Glu Pro Arg
    530                 535                 540

Val His Cys His Arg Lys Asp Gln Val Leu Thr Gly Cys Ser Ala His
545                 550                 555                 560

Trp Glu Ala Glu Asp Phe Arg Ala Arg Gly Trp Pro Met Leu Arg Pro
                565                 570                 575

Gly Gly Pro Ser Gln Cys Val Gly His Ser Lys Ala Ser Val His Ala
            580                 585                 590

Ser Cys Cys Ser Ala Pro Gly Leu Glu Cys Arg Ile Arg Glu His Gly
        595                 600                 605

Val Pro Trp Pro Ala Glu Gln Val Thr Val Ala Cys Glu Asp Gly Trp
    610                 615                 620

Thr Leu Thr Gly Cys Ser Thr Leu Pro Gly Ala Ser Ser Val Leu Gly
625                 630                 635                 640

Thr Tyr Ala Val Asp Asp Met Cys Val Val Arg Ser Arg Asp Val Lys
                645                 650                 655

Ala Leu Asp Arg Thr Arg Gly Glu Ala Leu Ala Ala Ile Ala Ile Cys
            660                 665                 670

Cys Arg Ser Gln Ala Ser Glu Gln Ala Ser Pro Glu Arg Gln His His
        675                 680                 685

His His His His
    690

<210> SEQ ID NO 5
<211> LENGTH: 704
<212> TYPE: PRT
<213> ORGANISM: Mesocricetus auratus

<400> SEQUENCE: 5

Met Gly Thr Ser Cys Ser Ala Arg Pro Arg Trp Leu Leu Ser Pro Leu
1               5                   10                  15

Leu Leu Leu Leu Leu Leu Leu Arg Tyr Met Gly Ala Ser Ala Gln Asp
            20                  25                  30

Glu Asp Ala Glu Tyr Glu Glu Leu Met Leu Thr Leu Gln Ser Gln Asp
        35                  40                  45

Asp Gly Leu Ala Asp Glu Thr Asp Glu Ala Pro Gln Gly Ala Thr Ala
    50                  55                  60

Ala Phe His Arg Cys Pro Glu Glu Ala Trp Arg Val Pro Gly Thr Tyr
65                  70                  75                  80

Ile Val Met Leu Ala Glu Glu Ala Gln Trp Val His Ile Glu Gln Thr
                85                  90                  95

Met His Arg Leu Gln Thr Gln Ala Ala Arg Arg Gly Tyr Val Ile Lys
            100                 105                 110

Ile Gln His Ile Phe Tyr Asp Phe Leu Pro Ala Phe Val Val Lys Met
        115                 120                 125

Ser Ser Asp Leu Leu Asp Leu Ala Leu Lys Leu Pro His Val Lys Tyr
    130                 135                 140

Ile Glu Glu Asp Ser Leu Val Phe Ala Gln Ser Ile Pro Trp Asn Leu
145                 150                 155                 160

```
Asp Arg Ile Ile Pro Ala Gly Arg Gln Ala Gln Glu Tyr Ser Ser Ser
            165                 170                 175

Arg Lys Val Pro Ser Gly Ser Gly Gln Val Glu Val Tyr Leu Leu Asp
            180                 185                 190

Thr Ser Ile Gln Ser Asp His Arg Glu Ile Glu Gly Arg Val Thr Val
            195                 200                 205

Thr Asp Phe Asn Ser Val Pro Glu Glu Asp Gly Thr Arg Phe His Arg
            210                 215                 220

Gln Ala Ser Lys Cys Asp Ser His Gly Thr His Leu Ala Gly Val Val
225                 230                 235                 240

Ser Gly Arg Asp Ala Gly Val Ala Lys Gly Thr Ile Leu His Gly Leu
            245                 250                 255

Arg Val Leu Asn Cys Gln Gly Lys Gly Ile Val Ser Gly Ile Leu Thr
            260                 265                 270

Gly Leu Glu Phe Ile Trp Lys Ser Gln Leu Met Gln Pro Ser Gly Pro
            275                 280                 285

Gln Val Val Leu Leu Pro Leu Ala Gly Arg Tyr Ser Arg Val Leu Asn
            290                 295                 300

Thr Ala Cys Gln His Leu Ala Arg Thr Gly Val Val Leu Val Ala Ala
305                 310                 315                 320

Ala Gly Asn Phe Arg Asp Asp Ala Cys Leu Tyr Ser Pro Ala Ser Ala
            325                 330                 335

Pro Glu Val Ile Thr Val Gly Ala Thr Asp Val Gln Asp Gln Pro Val
            340                 345                 350

Thr Leu Gly Thr Leu Gly Thr Asn Phe Gly Arg Cys Val Asp Leu Phe
            355                 360                 365

Ala Pro Gly Lys Asp Ile Ile Gly Ala Ser Ser Asp Cys Ser Ala Cys
            370                 375                 380

Phe Met Ser Gln Ser Gly Thr Ser Gln Ala Ala Ala His Val Ala Gly
385                 390                 395                 400

Ile Val Ala Met Met Leu Thr Leu Glu Pro Glu Leu Thr Leu Thr Glu
            405                 410                 415

Leu Arg Gln Arg Leu Ile His Phe Ser Thr Lys Asp Ala Ile Asn Met
            420                 425                 430

Ala Trp Phe Pro Glu Asp Gln Arg Val Leu Thr Pro Asn Leu Val Ala
            435                 440                 445

Thr Leu Pro Pro Ser Thr His Gly Thr Gly Gly Gln Leu Leu Cys Arg
            450                 455                 460

Thr Val Trp Ser Ala His Ser Gly Pro Thr Arg Ala Ala Thr Ala Thr
465                 470                 475                 480

Ala Arg Cys Ala Pro Gly Glu Glu Leu Leu Ser Cys Ser Ser Phe Ser
            485                 490                 495

Arg Ser Gly Arg Arg Gly Asp Arg Ile Glu Ala Ala Gly Thr Gln
            500                 505                 510

Gln Val Cys Lys Ala Leu Asn Ala Phe Gly Gly Glu Gly Val Tyr Ala
            515                 520                 525

Val Ala Arg Cys Cys Leu Leu Pro Arg Ala Asn Cys Ser Ile His Thr
530                 535                 540

Thr Pro Ala Ala Arg Thr Ser Leu Glu Thr His Ala His Cys His Gln
545                 550                 555                 560

Lys Asp His Val Leu Thr Gly Cys Ser Leu His Trp Glu Val Glu Gly
            565                 570                 575
```

```
Ile Gly Val Gln Pro Leu Ala Val Leu Arg Ser Arg His Gln Pro Gly
                580                 585                 590

Gln Cys Thr Gly His Arg Glu Ala Ser Val His Ala Ser Cys Cys His
            595                 600                 605

Ala Pro Gly Leu Glu Cys Lys Ile Lys Glu His Gly Ile Ser Gly Pro
        610                 615                 620

Ala Glu Gln Val Thr Val Ala Cys Glu Ala Gly Trp Thr Leu Thr Gly
625                 630                 635                 640

Cys Asn Val Leu Pro Gly Ala Phe Ile Thr Leu Gly Ala Tyr Ala Val
                645                 650                 655

Asp Asn Thr Cys Val Ala Arg Ser Arg Val Thr Asp Thr Ala Gly Arg
            660                 665                 670

Thr Gly Glu Glu Ala Thr Val Ala Ala Ile Cys Cys Arg Asn Arg
        675                 680                 685

Pro Ser Ala Lys Ala Ser Trp Val His Gln His His His His His
        690                 695                 700
```

<210> SEQ ID NO 6
<211> LENGTH: 695
<212> TYPE: PRT
<213> ORGANISM: Mus musculus

<400> SEQUENCE: 6

```
Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
                20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
        50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
130                 135                 140

Tyr Ile Glu Glu Asp Ser Phe Val Phe Ala Gln Ser Ile Pro Trp Asn
145                 150                 155                 160

Leu Arg Ile Ile Pro Ala Trp His Gln Thr Glu Glu Asp Arg Ser Pro
                165                 170                 175

Asp Gly Ser Ser Gln Val Glu Val Tyr Leu Leu Asp Thr Ser Ile Gln
            180                 185                 190

Gly Ala His Arg Glu Ile Glu Gly Arg Val Thr Ile Thr Asp Phe Asn
        195                 200                 205

Ser Val Pro Glu Glu Asp Gly Thr Arg Phe His Arg Gln Ala Ser Lys
210                 215                 220

Cys Asp Ser His Gly Thr His Leu Ala Gly Val Val Ser Gly Arg Asp
225                 230                 235                 240

Ala Gly Val Ala Lys Gly Thr Ser Leu His Ser Leu Arg Val Leu Asn
                245                 250                 255
```

```
Cys Gln Gly Lys Gly Thr Val Ser Gly Thr Leu Ile Gly Leu Glu Phe
            260                 265                 270
Ile Arg Lys Ser Gln Leu Ile Gln Pro Ser Pro Leu Val Leu Pro
        275                 280                 285
Leu Ala Gly Gly Tyr Ser Arg Ile Leu Asn Ala Ala Cys Arg His Leu
290                 295                 300
Ala Arg Thr Gly Val Val Leu Val Ala Ala Gly Asn Phe Arg Asp
305                 310                 315                 320
Asp Ala Cys Leu Tyr Ser Pro Ala Ser Ala Pro Glu Val Ile Thr Val
                    325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Lys Asp Ile
        355                 360                 365
Ile Gly Ala Ser Ser Asp Cys Ser Thr Cys Phe Met Ser Gln Ser Gly
370                 375                 380
Thr Ser Gln Ala Ala Ala His Val Ala Gly Ile Val Ala Arg Met Leu
385                 390                 395                 400
Ser Arg Glu Pro Thr Leu Thr Leu Ala Leu Arg Gln Arg Ile His Phe
                    405                 410                 415
Ser Thr Lys Asp Val Ile Asn Met Ala Trp Phe Pro Glu Asp Gln Gln
            420                 425                 430
Val Leu Thr Pro Asn Leu Val Ala Thr Leu Pro Pro Ser Thr His Glu
        435                 440                 445
Thr Gly Gly Gln Leu Leu Cys Arg Thr Val Trp Ser Ala His Ser Gly
450                 455                 460
Pro Thr Arg Thr Ala Thr Ala Thr Ala Arg Cys Ala Pro Glu Glu Glu
465                 470                 475                 480
Leu Leu Ser Cys Ser Ser Phe Ser Arg Ser Gly Arg Arg Gly Asp
                    485                 490                 495
Arg Ile Glu Ala Ile Gly Gly Gln Gln Val Cys Lys Ala Leu Asn Ala
            500                 505                 510
Phe Gly Gly Glu Gly Val Tyr Ala Val Ala Arg Cys Cys Leu Val Pro
        515                 520                 525
His Ala Asn Cys Ser Ile His Asn Pro Ala Ala Gly Leu Glu Thr
530                 535                 540
His Val His Cys His Gln Lys Asp His Val Leu Thr Gly Cys Ser Phe
545                 550                 555                 560
His Trp Glu Val Glu Asp Leu Ser Val Arg Arg Gln Pro Ala Leu Arg
                    565                 570                 575
Ser Arg Arg Gln Pro Gly Gln Cys Val Gly His Gln Ala Ala Ser Val
            580                 585                 590
Tyr Ala Ser Cys Cys His Ala Pro Gly Leu Glu Cys Lys Ile Lys Glu
        595                 600                 605
His Gly Ile Ser Gly Ser Ser Glu Gln Val Thr Val Ala Cys Glu Ala
610                 615                 620
Gly Trp Thr Leu Thr Gly Cys Asn Val Leu Pro Gly Ala Ser Leu Thr
625                 630                 635                 640
Leu Gly Ala Tyr Ser Val Asp Asn Leu Cys Val Ala Arg Val His Asp
                    645                 650                 655
Thr Ala Arg Ala Asp Arg Thr Gly Glu Thr Val Ala Ala Ile Cys
            660                 665                 670
```

Cys Arg Ser Arg Pro Ser Ala Lys Ala Ser Trp Val Gln Gly Pro His
                675                 680                 685

His His His His His His His
                690                 695

<210> SEQ ID NO 7
<211> LENGTH: 703
<212> TYPE: PRT
<213> ORGANISM: Macaca fascicularis

<400> SEQUENCE: 7

Met Gly Thr Val Ser Ser Arg Arg Ser Trp Trp Pro Leu Pro Leu Pro
 1               5                  10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Asp Ala Pro Glu His Gly Ala Thr Ala Thr Phe
        50                  55                  60

His Arg Cys Ala Lys Asp Pro Trp Arg Leu Pro Gly Thr Tyr Val Val
 65                 70                  75                  80

Val Leu Lys Glu Glu Thr His Arg Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Glu Arg Ile
145                 150                 155                 160

Thr Pro Ala Arg Tyr Arg Ala Asp Glu Tyr Gln Pro Pro Lys Gly Gly
                165                 170                 175

Ser Leu Val Glu Val Tyr Leu Leu Asp Thr Ser Ile Gln Ser Asp His
            180                 185                 190

Arg Glu Ile Glu Gly Arg Val Met Val Thr Asp Phe Glu Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Ala Gly Leu Arg Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Val Gln Pro Val Pro Leu Val Val Leu Pro Leu Ala Gly
        275                 280                 285

Gly Tyr Ser Arg Val Phe Asn Ala Ala Cys Gln Arg Leu Ala Arg Ala
    290                 295                 300

Gly Val Val Leu Val Thr Ala Ala Gly Asn Phe Arg Asp Asp Ala Cys
305                 310                 315                 320

Leu Tyr Ser Pro Ala Ser Ala Pro Glu Val Ile Thr Val Gly Ala Thr
                325                 330                 335

Asn Ala Gln Asp Gln Pro Val Thr Leu Gly Thr Leu Gly Thr Asn Phe
            340                 345                 350

Gly Arg Cys Val Asp Leu Phe Ala Pro Gly Glu Asp Ile Ile Gly Ala
            355                 360                 365

Ser Ser Asp Cys Ser Thr Cys Phe Val Ser Arg Ser Gly Thr Ser Gln
370                 375                 380

Ala Ala Ala His Val Ala Gly Ile Ala Ala Met Met Leu Ser Ala Glu
385                 390                 395                 400

Pro Glu Leu Thr Leu Ala Leu Arg Gln Leu Ile His Phe Ser Ala Lys
            405                 410                 415

Asp Val Ile Asn Glu Ala Trp Phe Pro Glu Asp Gln Arg Val Leu Thr
            420                 425                 430

Pro Asn Leu Val Ala Ala Leu Pro Pro Ser Thr His Arg Ala Gly Trp
            435                 440                 445

Gln Leu Phe Cys Arg Thr Val Trp Ser Ala His Ser Gly Pro Thr Arg
    450                 455                 460

Met Ala Thr Ala Val Ala Arg Cys Ala Gln Asp Glu Glu Leu Leu Ser
465                 470                 475                 480

Cys Ser Ser Phe Ser Arg Ser Gly Lys Arg Arg Gly Glu Arg Ile Glu
                485                 490                 495

Ala Gln Gly Gly Lys Arg Val Cys Arg Ala His Asn Ala Phe Gly Gly
            500                 505                 510

Glu Gly Val Tyr Ala Ile Ala Arg Cys Cys Leu Leu Pro Gln Val Asn
        515                 520                 525

Cys Ser Val His Thr Pro Pro Gly Ala Ser Met Gly Thr Arg Val His
    530                 535                 540

Cys His Gln Gln Gly His Val Leu Thr Gly Cys Ser Ser His Trp Glu
545                 550                 555                 560

Val Glu Asp Leu Gly Thr His Lys Pro Pro Val Leu Arg Pro Arg Gly
                565                 570                 575

Gln Pro Asn Gln Cys Val Gly His Arg Glu Ala Ser Ile His Ala Ser
            580                 585                 590

Cys Cys His Ala Pro Gly Leu Glu Cys Lys Val Arg Glu His Gly Ile
        595                 600                 605

Pro Ala Pro Gln Glu Gln Val Ile Val Ala Cys Glu Asp Gly Trp Thr
    610                 615                 620

Leu Thr Gly Cys Ser Ala Leu Pro Gly Thr Ser His Val Leu Gly Ala
625                 630                 635                 640

Tyr Ala Val Asp Asn Thr Cys Val Val Arg Ser Arg Asp Val Ser Thr
                645                 650                 655

Thr Gly Ser Thr Glu Ala Val Ala Val Ala Ile Cys Cys Arg Ser
            660                 665                 670

Arg His Leu Val Gln Ala Ser Gln Glu Leu Gln Gly Lys Pro Ile Pro
        675                 680                 685

Asn Pro Leu Leu Gly Leu Asp Ser Thr His His His His His
    690                 695                 700

<210> SEQ ID NO 8
<211> LENGTH: 699
<212> TYPE: PRT
<213> ORGANISM: Rattus norvegicus

<400> SEQUENCE: 8

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp

-continued

```
                20                  25                  30
Glu Asp Gly Asp Tyr Glu Leu Met Leu Ala Leu Pro Ser Gln Glu
            35                  40                  45
Asp Ser Leu Val Asp Glu Ala Ser His Val Ala Thr Ala Thr Phe Arg
 50                  55                  60
Arg Cys Ser Lys Glu Ala Trp Arg Leu Pro Gly Thr Tyr Val Val Val
 65                  70                  75                  80
Leu Met Glu Glu Thr Gln Arg Leu Gln Val Glu Gln Thr Ala His Arg
                85                  90                  95
Leu Gln Thr Trp Ala Ala Arg Arg Gly Tyr Val Ile Lys Val Leu His
                100                 105                 110
Val Phe Tyr Asp Leu Phe Pro Gly Phe Leu Val Lys Met Ser Ser Asp
                115                 120                 125
Leu Leu Gly Leu Ala Leu Lys Leu Pro His Val Glu Tyr Ile Glu Glu
                130                 135                 140
Asp Ser Leu Val Phe Ala Gln Ser Ile Pro Trp Asn Leu Glu Arg Ile
145                 150                 155                 160
Ile Pro Ala Trp Gln Gln Thr Glu Glu Asp Ser Ser Pro Asp Gly Ser
                165                 170                 175
Ser Gln Val Glu Val Tyr Leu Leu Asp Thr Ser Ile Gln Ser Gly His
                180                 185                 190
Arg Glu Ile Glu Gly Arg Val Thr Ile Thr Asp Phe Asn Ser Val Pro
                195                 200                 205
Glu Glu Asp Gly Thr Arg Phe His Arg Gln Ala Ser Lys Cys Asp Ser
                210                 215                 220
His Gly Thr His Leu Ala Gly Val Val Ser Gly Arg Asp Ala Gly Val
225                 230                 235                 240
Ala Lys Gly Thr Ser Leu His Ser Leu Arg Val Leu Asn Cys Gln Gly
                245                 250                 255
Lys Gly Thr Val Ser Gly Thr Leu Ile Gly Leu Glu Phe Ile Arg Lys
                260                 265                 270
Ser Gln Leu Ile Gln Pro Ser Gly Pro Leu Val Val Leu Leu Pro Leu
                275                 280                 285
Ala Gly Gly Tyr Ser Arg Ile Leu Asn Thr Ala Cys Gln Arg Leu Ala
                290                 295                 300
Arg Thr Gly Val Val Leu Val Ala Ala Gly Asn Phe Arg Asp Asp
305                 310                 315                 320
Ala Cys Leu Tyr Ser Pro Ala Ser Ala Pro Glu Val Ile Thr Val Gly
                325                 330                 335
Ala Thr Asn Ala Gln Asp Gln Pro Val Thr Leu Gly Thr Leu Gly Thr
                340                 345                 350
Asn Phe Gly Arg Cys Val Asp Leu Phe Ala Pro Gly Lys Asp Ile Ile
                355                 360                 365
Gly Ala Ser Ser Asp Cys Ser Thr Cys Tyr Met Ser Gln Ser Gly Thr
                370                 375                 380
Ser Gln Ala Ala Ala His Val Ala Gly Ile Val Ala Met Met Leu Asn
385                 390                 395                 400
Arg Asp Pro Ala Leu Thr Leu Ala Glu Leu Arg Gln Arg Leu Ile Leu
                405                 410                 415
Phe Ser Thr Lys Asp Val Ile Asn Met Ala Trp Phe Pro Glu Asp Gln
                420                 425                 430
Arg Val Leu Thr Pro Asn Arg Val Ala Thr Leu Pro Pro Ser Thr Gln
                435                 440                 445
```

-continued

```
Glu Thr Gly Gly Gln Leu Leu Cys Arg Thr Val Trp Ser Ala His Ser
    450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Arg Gly
                485                 490                 495

Asp Arg Ile Glu Ala Ile Gly Gly Gln Gln Val Cys Lys Ala Leu Asn
            500                 505                 510

Ala Phe Gly Gly Glu Gly Val Tyr Ala Val Ala Arg Cys Cys Leu Leu
        515                 520                 525

Pro Arg Val Asn Cys Ser Ile His Asn Thr Pro Ala Ala Arg Ala Gly
    530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
        595                 600                 605

Ile Lys Glu His Gly Ile Ala Gly Pro Ala Glu Gln Val Thr Val Ala
    610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln His His His His His His His
    690                 695

<210> SEQ ID NO 9
<211> LENGTH: 722
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4, 14, 15, 16, 17, 18, 63, 64, 65, 180, 181, 182, 183,
      583, 584, 586, 701, 703, 704, 705, 706, 707, 708, 709, 710, 711,
      712, 713, 714
<223> OTHER INFORMATION: Xaa = Any Amino Acid or No Amino Acid

<400> SEQUENCE: 9

Met Gly Thr Xaa Cys Ser Ala Arg Ser Trp Trp Pro Leu Xaa Xaa Xaa
1               5                   10                  15

Xaa Xaa Pro Leu Leu Leu Leu Leu Leu Leu Pro Ala Gly Ala Ala
            20                  25                  30

Ala Ala Gln Asp Glu Asp Gly Asp Tyr Glu Glu Leu Met Leu Ala Leu
        35                  40                  45

Pro Ser Gln Glu Asp Gly Leu Ala Asp Glu Ala Glu His Val Xaa Xaa
    50                  55                  60

Xaa Ala Thr Ala Thr Phe His Arg Cys Ser Lys Asp Ala Trp Arg Leu
65                  70                  75                  80
```

```
Pro Gly Thr Tyr Val Val Leu Lys Glu Glu Thr Gln Arg Leu Gln
                85                  90                  95

Ser Glu Gln Thr Ala His Arg Leu Gln Thr Gln Ala Ala Arg Arg Gly
            100                 105                 110

Tyr Val Thr Lys Ile Leu His Val Phe His Asp Leu Leu Pro Gly Phe
        115                 120                 125

Leu Val Lys Met Ser Ser Asp Leu Leu Asp Leu Ala Leu Lys Leu Pro
    130                 135                 140

His Val Asp Tyr Ile Glu Glu Asp Ser Ser Val Phe Ala Gln Ser Ile
145                 150                 155                 160

Pro Trp Asn Leu Glu Arg Ile Ile Pro Ala Arg His Gln Ala Asp Glu
                165                 170                 175

Tyr Ser Ser Xaa Xaa Xaa Xaa Pro Asp Gly Ser Ser Gln Val Glu Val
            180                 185                 190

Tyr Leu Leu Asp Thr Ser Ile Gln Ser Asp His Arg Glu Ile Glu Gly
        195                 200                 205

Arg Val Thr Val Thr Asp Phe Asn Ser Val Pro Glu Glu Asp Gly Thr
    210                 215                 220

Arg Phe His Arg Gln Ala Ser Lys Cys Asp Ser His Gly Thr His Leu
225                 230                 235                 240

Ala Gly Val Val Ser Gly Arg Asp Ala Gly Val Ala Lys Gly Thr Ser
                245                 250                 255

Leu Arg Ser Leu Arg Val Leu Asn Cys Gln Gly Lys Gly Thr Val Ser
            260                 265                 270

Gly Thr Leu Ile Gly Leu Glu Phe Ile Arg Lys Ser Gln Leu Ile Gln
        275                 280                 285

Pro Val Gly Pro Leu Val Val Leu Leu Pro Leu Ala Gly Gly Tyr Ser
    290                 295                 300

Arg Val Leu Asn Ala Ala Cys Gln Arg Leu Ala Arg Thr Gly Val Val
305                 310                 315                 320

Leu Val Ala Ala Ala Gly Asn Phe Arg Asp Asp Ala Cys Leu Tyr Ser
                325                 330                 335

Pro Ala Ser Ala Pro Glu Val Ile Thr Val Gly Ala Thr Asn Ala Gln
            340                 345                 350

Asp Gln Pro Val Thr Leu Gly Thr Leu Gly Thr Asn Phe Gly Arg Cys
        355                 360                 365

Val Asp Leu Phe Ala Pro Gly Lys Asp Ile Ile Gly Ala Ser Ser Asp
    370                 375                 380

Cys Ser Thr Cys Phe Met Ser Gln Ser Gly Thr Ser Gln Ala Ala Ala
385                 390                 395                 400

His Val Ala Gly Ile Val Ala Met Met Leu Ser Ala Glu Pro Glu Leu
                405                 410                 415

Thr Leu Ala Glu Leu Arg Gln Arg Leu Ile His Phe Ser Thr Lys Asp
            420                 425                 430

Val Ile Asn Met Ala Trp Phe Pro Glu Asp Gln Arg Val Leu Thr Pro
        435                 440                 445

Asn Leu Val Ala Thr Leu Pro Pro Ser Thr His Gly Thr Gly Gly Gln
    450                 455                 460

Leu Leu Cys Arg Thr Val Trp Ser Ala His Ser Gly Pro Thr Arg Thr
465                 470                 475                 480

Ala Thr Ala Thr Ala Arg Cys Ala Pro Asp Glu Glu Leu Leu Ser Cys
                485                 490                 495
```

Ser Ser Phe Ser Arg Ser Gly Lys Arg Arg Gly Asp Arg Ile Glu Ala
            500                 505                 510

Ile Gly Gly Gln Gln Val Cys Lys Ala Leu Asn Ala Phe Gly Gly Glu
        515                 520                 525

Gly Val Tyr Ala Val Ala Arg Cys Cys Leu Leu Pro Arg Ala Asn Cys
    530                 535                 540

Ser Ile His Thr Thr Pro Ala Arg Ala Ser Met Glu Thr Arg Val
545                 550                 555                 560

His Cys His Gln Lys Asp His Val Leu Thr Gly Cys Ser Ser His Trp
                565                 570                 575

Glu Val Glu Asp Leu Gly Xaa Xaa Lys Xaa Pro Val Leu Arg Ser Arg
            580                 585                 590

Gly Gln Pro Gly Gln Cys Val Gly His Arg Glu Ala Ser Val His Ala
        595                 600                 605

Ser Cys Cys His Ala Pro Gly Leu Glu Cys Lys Ile Lys Glu His Gly
    610                 615                 620

Ile Pro Gly Pro Ala Glu Gln Val Thr Val Ala Cys Glu Ala Gly Trp
625                 630                 635                 640

Thr Leu Thr Gly Cys Ser Val Leu Pro Gly Ala Ser Leu Val Leu Gly
                645                 650                 655

Ala Tyr Ala Val Asp Asn Thr Cys Val Val Arg Ser Arg Asp Val Ser
            660                 665                 670

Thr Ala Gly Arg Thr Ser Glu Ala Thr Val Ala Ala Ile Cys
        675                 680                 685

Cys Arg Ser Arg Pro Ser Ala Gln Ala Ser Trp Val Xaa Gln Xaa Xaa
    690                 695                 700

Xaa Xaa Xaa Xaa Xaa Xaa Xaa Xaa Xaa His His His His His
705                 710                 715                 720

His His

<210> SEQ ID NO 10
<211> LENGTH: 293
<212> TYPE: PRT
<213> ORGANISM: Homo sapiens

<400> SEQUENCE: 10

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

```
Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro
    290

<210> SEQ ID NO 11
<211> LENGTH: 293
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 7, 10, 11, 12, 13, 14, 16, 17, 20, 23, 24, 26, 27, 37,
      40, 47, 49, 51, 55, 58, 62, 63, 66, 72, 78, 82, 91, 92, 94,
      95, 98, 113, 114, 121, 122, 128, 129, 132, 137, 141, 144,
      150, 151, 153, 155, 157, 158, 159, 160, 161, 166, 172, 178
<223> OTHER INFORMATION: Xaa = Any Amino Acid or No Amino Acid
<220> FEATURE:
<221> NAME/KEY: VARIANT
<222> LOCATION: 194, 195, 198, 224, 228, 245, 247, 249, 253, 256, 257,
      268, 270, 271, 283, 291
<223> OTHER INFORMATION: Xaa = Any Amino Acid or No Amino Acid

<400> SEQUENCE: 11

Ser Ile Pro Trp Asn Leu Xaa Arg Ile Xaa Xaa Xaa Xaa Xaa Arg Xaa
 1               5                  10                  15

Xaa Glu Tyr Xaa Pro Pro Xaa Xaa Gly Xaa Xaa Val Glu Val Tyr Leu
            20                  25                  30

Leu Asp Thr Ser Xaa Gln Ser Xaa His Arg Glu Ile Glu Gly Xaa Val
        35                  40                  45

Xaa Val Xaa Asp Phe Glu Xaa Val Pro Xaa Glu Asp Gly Xaa Xaa Phe
    50                  55                  60

His Xaa Gln Ala Ser Lys Cys Xaa Ser His Gly Thr His Xaa Ala Gly
65                  70                  75                  80

Val Xaa Ser Gly Arg Asp Ala Gly Val Ala Xaa Xaa Ala Xaa Xaa Arg
                85                  90                  95

Ser Xaa Arg Val Leu Asn Cys Gln Gly Lys Gly Thr Val Ser Gly Thr
            100                 105                 110

Xaa Xaa Gly Leu Glu Phe Ile Arg Xaa Xaa Gln Leu Val Gln Pro Xaa
        115                 120                 125

Xaa Pro Leu Xaa Val Leu Leu Pro Xaa Ala Gly Gly Xaa Ser Arg Xaa
    130                 135                 140
```

Leu Asn Ala Ala Cys Xaa Xaa Leu Xaa Arg Xaa Gly Xaa Xaa Xaa Xaa
145                 150                 155                 160

Xaa Ala Ala Gly Asn Xaa Arg Asp Asp Ala Cys Xaa Tyr Ser Pro Ala
            165                 170                 175

Ser Xaa Pro Glu Val Ile Thr Val Gly Ala Thr Asn Ala Gln Asp Gln
        180                 185                 190

Pro Xaa Xaa Leu Gly Xaa Leu Gly Thr Asn Phe Gly Arg Cys Val Asp
        195                 200                 205

Leu Phe Ala Pro Gly Glu Asp Ile Ile Gly Ala Ser Ser Asp Cys Xaa
210                 215                 220

Thr Cys Phe Xaa Ser Gln Ser Gly Thr Ser Gln Ala Ala Ala His Val
225                 230                 235                 240

Ala Gly Ile Ala Xaa Met Xaa Leu Xaa Ala Glu Pro Xaa Leu Thr Xaa
            245                 250                 255

Xaa Glu Leu Arg Gln Arg Leu Ile His Phe Ser Xaa Lys Xaa Xaa Ile
        260                 265                 270

Asn Glu Ala Trp Phe Pro Glu Asp Gln Arg Xaa Leu Thr Pro Asn Leu
            275                 280                 285

Val Ala Xaa Leu Pro
        290

<210> SEQ ID NO 12
<211> LENGTH: 293
<212> TYPE: PRT
<213> ORGANISM: Monodelphis domestica

<400> SEQUENCE: 12

Ser Ile Pro Trp Asn Leu Asp Arg Ile Val Leu Ala Pro Ser Arg Ser
1               5                   10                  15

Glu Glu Tyr Ser Pro Pro Asn Lys Gly Asp Gln Val Glu Val Tyr Leu
            20                  25                  30

Leu Asp Thr Ser Leu Gln Ser Gly His Arg Glu Ile Glu Gly Lys Val
        35                  40                  45

Thr Val Ala Asp Phe Glu Asp Val Pro Asp Glu Asp Gly Ala Gln Phe
50                  55                  60

His Ser Gln Ala Ser Lys Cys Glu Ser His Gly Thr His Val Ala Gly
65                  70                  75                  80

Val Leu Ser Gly Arg Asp Ala Gly Val Ala Arg Ala Ala Val Arg
            85                  90                  95

Ser Val Arg Val Leu Asn Cys Gln Gly Lys Gly Thr Val Ser Gly Thr
        100                 105                 110

Ala Arg Gly Leu Glu Phe Ile Arg Arg Thr Gln Leu Val Gln Pro Tyr
        115                 120                 125

Ser Pro Leu Ile Val Leu Leu Pro Phe Ala Gly Gly His Ser Arg Thr
130                 135                 140

Leu Asn Ala Ala Cys Arg Leu Leu Val Arg Ser Gly Ala Ala Val Ile
145                 150                 155                 160

Ala Ala Ala Gly Asn Tyr Arg Asp Asp Ala Cys Ser Tyr Ser Pro Ala
            165                 170                 175

Ser Glu Pro Glu Val Ile Thr Val Gly Ala Thr Asn Ala Gln Asp Gln
        180                 185                 190

Pro Ala Ala Leu Gly Ala Leu Gly Thr Asn Phe Gly Arg Cys Val Asp
        195                 200                 205

Leu Phe Ala Pro Gly Glu Asp Ile Ile Gly Ala Ser Ser Asp Cys Gly
210                 215                 220

-continued

```
Thr Cys Phe Thr Ser Gln Ser Gly Thr Ser Gln Ala Ala His Val
225                 230                 235                 240

Ala Gly Ile Ala Ser Met Leu Leu Asn Ala Glu Pro Ser Leu Thr Val
                245                 250                 255

Pro Glu Leu Arg Gln Arg Leu Ile His Phe Ser Val Lys Asn Ala Ile
            260                 265                 270

Asn Glu Ala Trp Phe Pro Glu Asp Gln Arg Leu Leu Thr Pro Asn Leu
        275                 280                 285

Val Ala Arg Leu Pro
    290

<210> SEQ ID NO 13
<211> LENGTH: 293
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 7, 10, 12, 13, 14, 15, 17, 18, 19, 20, 23, 24, 26,
      27, 40, 47, 49, 54, 72, 78, 83, 93, 94, 95, 112, 114, 122, 123,
      124, 125, 128, 129, 132, 134, 135, 137, 138, 144, 149, 150,
      151, 153, 154, 155, 158, 159, 160, 161, 166, 167, 178
<223> OTHER INFORMATION: Xaa = Any Amino Acid or No Amino Acid
<220> FEATURE:
<221> NAME/KEY: VARIANT
<222> LOCATION: 184, 189, 194, 196, 198, 203, 205, 207, 214, 228, 230,
      247, 249, 250, 251, 253, 255, 256, 257, 265, 268, 270, 275, 283,
      284, 288, 291
<223> OTHER INFORMATION: Xaa = Any Amino Acid or No Amino Acid

<400> SEQUENCE: 13

Ser Xaa Pro Trp Asn Leu Xaa Arg Ile Xaa Pro Xaa Xaa Xaa Xaa Ala
1               5                   10                  15

Xaa Xaa Xaa Xaa Pro Pro Xaa Xaa Gly Xaa Xaa Val Glu Val Tyr Leu
            20                  25                  30

Leu Asp Thr Ser Ile Gln Ser Xaa His Arg Glu Ile Glu Gly Xaa Val
            35                  40                  45

Xaa Val Thr Asp Phe Xaa Asn Val Pro Glu Glu Asp Gly Thr Arg Phe
    50                  55                  60

His Arg Gln Ala Ser Lys Cys Xaa Ser His Gly Thr His Xaa Ala Gly
65                  70                  75                  80

Val Val Xaa Gly Arg Asp Ala Gly Val Ala Lys Gly Xaa Xaa Xaa Arg
                85                  90                  95

Ser Leu Arg Val Leu Asn Cys Gln Gly Lys Gly Thr Val Ser Gly Xaa
            100                 105                 110

Leu Xaa Gly Leu Glu Phe Ile Arg Lys Xaa Xaa Xaa Xaa Gln Pro Xaa
        115                 120                 125

Xaa Pro Leu Xaa Val Xaa Xaa Pro Xaa Xaa Gly Gly Tyr Ser Arg Xaa
    130                 135                 140

Leu Asn Ala Ala Xaa Xaa Xaa Leu Xaa Xaa Xaa Gly Val Xaa Xaa Xaa
145                 150                 155                 160

Xaa Ala Ala Gly Asn Xaa Xaa Asp Asp Ala Cys Leu Tyr Ser Pro Ala
                165                 170                 175

Ser Xaa Pro Glu Val Ile Thr Xaa Gly Ala Thr Asn Xaa Gln Asp Gln
            180                 185                 190

Pro Xaa Thr Xaa Gly Xaa Leu Gly Thr Asn Xaa Gly Xaa Cys Xaa Asp
            195                 200                 205

Leu Phe Ala Pro Gly Xaa Asp Ile Ile Gly Ala Ser Ser Asp Cys Ser
```

```
            210                 215                 220
Thr Cys Phe Xaa Ser Xaa Ser Gly Thr Ser Gln Ala Ala His Val
225                 230                 235                 240

Ala Gly Ile Ala Ala Met Xaa Leu Xaa Xaa Xaa Pro Xaa Leu Xaa Xaa
                245                 250                 255

Xaa Glu Leu Arg Gln Arg Leu Ile Xaa Phe Ser Xaa Lys Xaa Val Ile
            260                 265                 270

Asn Glu Xaa Trp Phe Pro Glu Asp Gln Arg Xaa Xaa Thr Pro Asn Xaa
            275                 280                 285

Val Ala Xaa Leu Pro
            290

<210> SEQ ID NO 14
<211> LENGTH: 293
<212> TYPE: PRT
<213> ORGANISM: Xenopus laevis

<400> SEQUENCE: 14

Ser Val Pro Trp Asn Leu Asp Arg Ile Val Pro Ala Gln Gln Met Ala
1               5                   10                  15

Ser Gln Phe Ser Pro Pro Asn Thr Gly Asp Ser Val Glu Val Tyr Leu
            20                  25                  30

Leu Asp Thr Ser Ile Gln Ser Asn His Arg Glu Ile Glu Gly Lys Val
            35                  40                  45

Phe Val Thr Asp Phe Gln Asn Val Pro Glu Glu Asp Gly Thr Arg Phe
        50                  55                  60

His Arg Gln Ala Ser Lys Cys Glu Ser His Gly Thr His Met Ala Gly
65                  70                  75                  80

Val Val Asn Gly Arg Asp Ala Gly Val Ala Lys Gly Val Asn Val Arg
                85                  90                  95

Ser Leu Arg Val Leu Asn Cys Gln Gly Lys Gly Thr Val Ser Gly Ser
            100                 105                 110

Leu Thr Gly Leu Glu Phe Ile Arg Lys Thr Leu Ile Glu Gln Pro Tyr
        115                 120                 125

Asn Pro Leu Ile Val Ile Pro Phe Val Gly Gly Tyr Ser Arg Ile
    130                 135                 140

Leu Asn Ala Ala Ser Arg Ala Leu Val Asn Thr Gly Val Ile Ile Ile
145                 150                 155                 160

Ala Ala Ala Gly Asn Tyr Lys Asp Asp Ala Cys Leu Tyr Ser Pro Ala
                165                 170                 175

Ser Glu Pro Glu Val Ile Thr Ile Gly Ala Thr Asn Tyr Gln Asp Gln
            180                 185                 190

Pro Ala Thr Met Gly Val Leu Gly Thr Asn Tyr Gly Asn Cys Ile Asp
        195                 200                 205

Leu Phe Ala Pro Gly Asp Asp Ile Ile Gly Ala Ser Ser Asp Cys Ser
    210                 215                 220

Thr Cys Phe Thr Ser Lys Ser Gly Thr Ser Gln Ala Ala His Val
225                 230                 235                 240

Ala Gly Ile Ala Ala Met Ile Leu Asn Asp Lys Pro Asp Leu Ser Val
                245                 250                 255

Ser Glu Leu Arg Gln Arg Leu Ile Gln Phe Ser Thr Lys Lys Val Ile
            260                 265                 270

Asn Glu Val Trp Phe Pro Glu Asp Gln Arg Leu Ile Thr Pro Asn Arg
            275                 280                 285
```

```
Val Ala Gly Leu Pro
    290

<210> SEQ ID NO 15
<211> LENGTH: 323
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3, 5, 7-9, 12, 14-19, 21, 22, 24, 25, 31, 33, 35, 36,
      38, 42, 43, 47, 52, 53, 56-62, 65, 68, 70, 71, 76, 78, 81, 83, 85,
      89, 92, 93-96, 100, 102, 110, 112, 114, 116, 119-124, 126, 128,
      129, 135, 136, 138, 139, 142, 148, 149, 151-153, 155, 157,
      159, 164, 176, 179-209, 216, 218, 219, 222, 224, 225, 227, 228,
      232, 238, 243, 246, 247, 253, 257, 259, 269, 272, 275, 276,
      279, 280, 282, 285-289, 291, 293-295, 297-313, 316
<223> OTHER INFORMATION: Xaa = Any Amino Acid or No Amino Acid

<400> SEQUENCE: 15

Pro Trp Xaa Leu Xaa Arg Xaa Xaa Pro Arg Xaa Arg Xaa Xaa Xaa
  1               5                  10                  15

Xaa Xaa Xaa Pro Xaa Xaa Gly Xaa Xaa Val Glu Val Tyr Leu Xaa Asp
                 20                  25                  30

Xaa Ser Xaa Xaa Ser Xaa His Arg Glu Xaa Xaa Gly Arg Val Xaa Val
         35                  40                  45

Thr Asp Phe Xaa Xaa Val Pro Xaa Xaa Xaa Xaa Xaa Xaa His Arg
 50                  55                  60

Xaa Ala Ser Xaa Cys Xaa Xaa His Gly Thr His Xaa Ala Xaa Val Val
 65                  70                  75                  80

Xaa Gly Xaa Asp Xaa Gly Val Ala Xaa Gly Ala Xaa Xaa Xaa Xaa
                 85                  90                  95

Arg Val Leu Xaa Cys Xaa Gly Lys Gly Thr Val Ser Gly Xaa Leu Xaa
                100                 105                 110

Gly Xaa Glu Xaa Ile Arg Xaa Xaa Xaa Xaa Xaa Pro Xaa Gly Xaa
            115                 120                 125

Xaa Val Val Leu Leu Pro Xaa Xaa Gly Xaa Xaa Ser Arg Xaa Leu Asn
    130                 135                 140

Ala Ala Cys Xaa Xaa Leu Xaa Xaa Xaa Gly Xaa Val Xaa Val Xaa Ala
145                 150                 155                 160

Ala Gly Asn Xaa Arg Asp Asp Ala Cys Leu Tyr Ser Pro Ala Ser Xaa
                165                 170                 175

Pro Glu Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
            195                 200                 205

Xaa Val Ile Thr Val Gly Ala Xaa Asn Xaa Xaa Asp Gln Xaa Val Xaa
    210                 215                 220

Xaa Gly Xaa Xaa Gly Thr Asn Xaa Gly Arg Cys Val Asp Xaa Phe Ala
225                 230                 235                 240

Pro Gly Xaa Asp Ile Xaa Xaa Ala Ser Ser Asp Cys Xaa Thr Cys Phe
            245                 250                 255

Xaa Ser Xaa Ser Gly Thr Ser Gln Ala Ala His Xaa Ala Gly Xaa
            260                 265                 270

Ala Ala Xaa Xaa Leu Ser Xaa Xaa Pro Xaa Leu Thr Xaa Xaa Xaa Xaa
        275                 280                 285

Xaa Gln Xaa Leu Xaa Xaa Xaa Ser Xaa Xaa Xaa Xaa Xaa Xaa Xaa
    290                 295                 300
```

```
Xaa Xaa Xaa Xaa Xaa Xaa Xaa Xaa Thr Pro Xaa Leu Val Ala Ala
305                 310                 315                 320

Leu Pro Pro

<210> SEQ ID NO 16
<211> LENGTH: 312
<212> TYPE: PRT
<213> ORGANISM: Tetraodon nigroviridis

<400> SEQUENCE: 16

Pro Trp Ser Leu Arg Arg Leu Pro Arg Pro Arg Gly Arg Pro Gly Asp
  1               5                  10                  15

Gly Ala Ala Val Glu Val Tyr Leu Met Asp Gly Ser Val Leu Ser Ser
             20                  25                  30

His Arg Glu Leu Gly Gly Arg Val Leu Val Thr Asp Phe His Ser Val
         35                  40                  45

Pro Val Gly Glu Ala Gly Gly His Arg Glu Ala Ser Arg Cys Lys Gly
     50                  55                  60

His Gly Thr His Val Ala Ala Val Met Gly Ser Asp Thr Gly Val
 65                  70                  75                  80

Ala Pro Gly Ala Arg Val Asn Leu Val Arg Val Leu Asp Cys Arg Gly
                 85                  90                  95

Lys Gly Thr Val Ser Gly Ala Leu Ala Gly Val Glu Tyr Ile Arg Ala
             100                 105                 110

Ala Leu Arg Ala His Pro Pro Gly Ala Ala Val Leu Leu Pro Phe
         115                 120                 125

Thr Gly Ala Phe Ser Arg Ser Leu Asn Ala Ala Cys Arg Asp Leu Val
130                 135                 140

Asn Thr Gly Ala Val Val Val Ala Ala Gly Asn Tyr Arg Asp Asp
145                 150                 155                 160

Ala Cys Leu Tyr Ser Pro Ala Ser Glu Pro Glu Val Cys Thr Gly Gly
                165                 170                 175

Ser Ala Arg Ser His Thr His Thr His Thr His Thr His Leu
             180                 185                 190

Leu Gln Ala Val Leu Cys Val Cys Val Gln Val Ile Thr Val Gly Ala
         195                 200                 205

Val Asn Ser Ala Asp Gln Leu Val Ser Gln Gly Pro Gly Thr Asn
210                 215                 220

Val Gly Arg Cys Val Asp Val Phe Ala Pro Gly Gly Asp Ile Val Ser
225                 230                 235                 240

Ala Ser Ser Asp Cys Asp Thr Cys Phe Ala Ser Gly Ser Gly Thr Ser
                245                 250                 255

Gln Ala Ala Ala His Ala Ala Gly Met Ala Ala Val Leu Leu Ser Ser
             260                 265                 270

Ser Pro Ser Leu Thr Pro Val Gln Val Leu Gln Thr Leu Leu Arg Tyr
         275                 280                 285

Ser Val Ser Leu Pro Ser Val Ser Gly Arg Arg Gly Leu Val Thr Pro
     290                 295                 300

Ser Leu Val Ala Ala Leu Pro Pro
305                 310

<210> SEQ ID NO 17
<211> LENGTH: 292
<212> TYPE: PRT
<213> ORGANISM: Homo sapiens
```

<400> SEQUENCE: 17

Pro Trp Asn Leu Glu Arg Ile Thr Pro Pro Tyr Arg Ala Asp Glu
1               5                   10                  15

Tyr Gln Pro Pro Asp Gly Gly Ser Leu Val Glu Val Tyr Leu Leu Asp
            20                  25                  30

Thr Ser Ile Gln Ser Asp His Arg Glu Ile Glu Gly Arg Val Met Val
        35                  40                  45

Thr Asp Phe Glu Asn Val Pro Glu Glu Asp Gly Thr Arg Phe His Arg
50                  55                  60

Gln Ala Ser Lys Cys Asp Ser His Gly Thr His Leu Ala Gly Val Val
65                  70                  75                  80

Ser Gly Arg Asp Ala Gly Val Ala Lys Gly Ala Ser Met Arg Ser Leu
                85                  90                  95

Arg Val Leu Asn Cys Gln Gly Lys Gly Thr Val Ser Gly Thr Leu Ile
            100                 105                 110

Gly Leu Glu Phe Ile Arg Lys Ser Gln Leu Val Gln Pro Val Gly Pro
        115                 120                 125

Leu Val Val Leu Leu Pro Leu Ala Gly Gly Tyr Ser Arg Val Leu Asn
130                 135                 140

Ala Ala Cys Gln Arg Leu Ala Arg Ala Gly Val Val Leu Val Thr Ala
145                 150                 155                 160

Ala Gly Asn Phe Arg Asp Asp Ala Cys Leu Tyr Ser Pro Ala Ser Ala
                165                 170                 175

Pro Glu Val Ile Thr Val Gly Ala Thr Asn Ala Gln Asp Gln Pro Val
            180                 185                 190

Thr Leu Gly Thr Leu Gly Thr Asn Phe Gly Arg Cys Val Asp Leu Phe
        195                 200                 205

Ala Pro Gly Glu Asp Ile Ile Gly Ala Ser Ser Asp Cys Ser Thr Cys
210                 215                 220

Phe Val Ser Gln Ser Gly Thr Ser Gln Ala Ala Ala His Val Ala Gly
225                 230                 235                 240

Ile Ala Ala Met Met Leu Ser Ala Glu Pro Glu Leu Thr Leu Ala Glu
                245                 250                 255

Leu Arg Gln Arg Leu Ile His Phe Ser Ala Lys Asp Val Ile Asn Glu
            260                 265                 270

Ala Trp Phe Pro Glu Asp Gln Arg Val Leu Thr Pro Asn Leu Val Ala
        275                 280                 285

Ala Leu Pro Pro
    290

<210> SEQ ID NO 18
<211> LENGTH: 860
<212> TYPE: PRT
<213> ORGANISM: Homo sapiens

<400> SEQUENCE: 18

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
50                  55                  60

-continued

```
Ser Val Thr Cys Lys Ser Gly Asp Phe Ser Cys Gly Gly Arg Val Asn
 65                  70                  75                  80

Arg Cys Ile Pro Gln Phe Trp Arg Cys Asp Gly Gln Val Asp Cys Asp
                 85                  90                  95

Asn Gly Ser Asp Glu Gln Gly Cys Pro Pro Lys Thr Cys Ser Gln Asp
                100                 105                 110

Glu Phe Arg Cys His Asp Gly Lys Cys Ile Ser Arg Gln Phe Val Cys
            115                 120                 125

Asp Ser Asp Arg Asp Cys Leu Asp Gly Ser Asp Glu Ala Ser Cys Pro
130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
            195                 200                 205

Cys Ile His Ser Ser Trp Arg Cys Asp Gly Gly Pro Asp Cys Lys Asp
210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
            275                 280                 285

Cys Ile Thr Leu Asp Lys Val Cys Asn Met Ala Arg Asp Cys Arg Asp
290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
            370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
            450                 455                 460

Tyr Asp Thr Val Ile Ser Arg Asp Ile Gln Ala Pro Asp Gly Leu Ala
465                 470                 475                 480
```

-continued

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Val Ala
    850                 855                 860

<210> SEQ ID NO 19
<211> LENGTH: 860
<212> TYPE: PRT
<213> ORGANISM: Macaca fascicularis

<400> SEQUENCE: 19

```
Met Glu Pro Trp Gly Trp Lys Leu Arg Trp Thr Val Ala Phe Leu Leu
 1               5                  10                  15

Ala Ala Ala Glu Ala Ala Val Gly Asp Arg Cys Glu Arg Asn Glu Phe
            20                  25                  30

Gln Cys Glu Asp Gly Lys Cys Ile Ser Tyr Lys Trp Val Cys Asp Gly
        35                  40                  45

Thr Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
 65              70                  75                  80

Arg Cys Ile Pro Gln Phe Trp Arg Cys Asp Gly Glu Val Asp Cys Glu
                85                  90                  95

Asn Gly Ser Asp Glu Gln Asp Cys Pro Pro Lys Thr Cys Ser Gln Asp
            100                 105                 110

Glu Phe Arg Cys His Asp Gly Lys Cys Ile Tyr Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln His Cys Gln Gly Leu Glu Val Pro Lys Arg
            180                 185                 190

Asp Ser Ser Pro Cys Ser Ala Phe Glu Phe His Cys Gln Ser Gly Glu
    195                 200                 205

Cys Ile His Ser Gly Trp Arg Cys Asp Gly Gly Pro Asp Cys Lys Asp
    210                 215                 220

Lys Ser Asp Glu Glu Asn Cys Pro Val Ala Thr Cys Arg Pro Asp Glu
225                 230                 235                 240

Phe Gln Cys Ser Asp Gly Thr Cys Ile His Gly Ser Arg Gln Cys Asp
            245                 250                 255

Arg Glu Tyr Asp Cys Lys Asp Met Ser Asp Glu Val Gly Cys Ile Asn
            260                 265                 270

Val Thr Leu Cys Glu Gly Pro Asn Lys Phe Lys Cys His Ser Gly Glu
    275                 280                 285

Cys Ile Ser Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Ile Cys Asn Asp Leu Lys Ile Gly Tyr
            325                 330                 335

Glu Cys Leu Cys Pro Asp Gly Phe Gln Leu Val Ala Gln Arg Arg Cys
        340                 345                 350

Glu Asp Ile Asp Glu Cys Gln Asp Pro Asp Thr Cys Ser Gln Leu Cys
        355                 360                 365

Val Asn Leu Glu Gly Ser Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Ile Phe Thr Asn Arg His Glu Val Arg Lys Met Thr Leu Asp Arg
                405                 410                 415
```

```
Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
            435                 440                 445

Arg Met Ile Tyr Ser Thr Gln Leu Asp Arg Ala His Ser Val Ser Ser
            450                 455                 460

Tyr Asp Thr Val Ile Ser Arg Asp Leu Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
            530                 535                 540

Gly Gly Leu Asn Gly Val Asp Ile Tyr Ser Leu Val Thr Glu Asn Ile
545                 550                 555                 560

Glu Trp Pro Asn Gly Ile Thr Leu Asp Phe Pro Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Val Leu Glu Asp Glu Arg Leu Ala His Pro
            595                 600                 605

Phe Ser Leu Ala Ile Phe Glu Asp Lys Val Phe Trp Thr Asp Ile Ile
            610                 615                 620

Asn Glu Ala Ile Phe Ser Ala Asn Arg Leu Thr Gly Ser Asp Ile Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
            675                 680                 685

Pro Gln Ser Pro Lys Phe Thr Cys Thr Cys Pro Asp Gly Met Leu Leu
            690                 695                 700

Ala Lys Asp Met Arg Ser Cys Leu Thr Glu Ala Glu Ala Val Ala
705                 710                 715                 720

Thr Gln Glu Thr Ser Thr Val Arg Leu Met Val Ser Lys Ala Val
                725                 730                 735

Ala Thr Gln His Thr Thr Thr Arg Pro Val Pro Asn Thr Ser Gln Leu
            740                 745                 750

Pro Gly Ala Thr Pro Gly Leu Thr Thr Ala Glu Thr Val Thr Met Ser
            755                 760                 765

His Gln Ala Leu Gly Asp Val Ala Gly Arg Gly Asn Glu Lys Lys Pro
            770                 775                 780

Lys Ser Val Gly Ala Leu Ser Ile Val Leu Pro Thr Val Leu Leu Val
785                 790                 795                 800

Phe Leu Cys Leu Gly Ala Phe Leu Leu Trp Lys Asn Trp Arg Leu Lys
                805                 810                 815

Ser Ile Asn Ser Ile Asn Phe Asp Asn Pro Val Tyr Gln Lys Thr Thr
            820                 825                 830

Glu Asp Glu Val His Ile Cys Arg Asn Gln Asp Gly Tyr Ser Tyr Pro
```

```
                    835                 840                 845
Ser Arg Gln Met Val Ser Leu Glu Asp Asp Val Ala
    850                 855                 860

<210> SEQ ID NO 20
<211> LENGTH: 862
<212> TYPE: PRT
<213> ORGANISM: Mus musculus

<400> SEQUENCE: 20

Met Ser Thr Ala Asp Leu Met Arg Arg Trp Val Ile Ala Leu Leu Leu
  1               5                  10                  15

Ala Ala Ala Gly Val Ala Ala Glu Asp Ser Cys Ser Arg Asn Glu Phe
                 20                  25                  30

Gln Cys Arg Asp Gly Lys Cys Ile Ala Ser Lys Trp Val Cys Asp Gly
             35                  40                  45

Ser Pro Glu Cys Pro Asp Gly Ser Asp Glu Ser Pro Glu Thr Cys Met
 50                  55                  60

Ser Val Thr Cys Gln Ser Asn Gln Phe Ser Cys Gly Gly Arg Val Ser
 65                  70                  75                  80

Arg Cys Ile Pro Asp Ser Trp Arg Cys Asp Gly Gln Val Asp Cys Glu
                 85                  90                  95

Asn Asp Ser Asp Glu Gln Gly Cys Pro Pro Lys Thr Cys Ser Gln Asp
                100                 105                 110

Asp Phe Arg Cys Gln Asp Gly Lys Cys Ile Ser Pro Gln Phe Val Cys
            115                 120                 125

Asp Gly Asp Arg Asp Cys Leu Asp Gly Ser Asp Glu Ala His Cys Gln
130                 135                 140

Ala Thr Thr Cys Gly Pro Ala His Phe Arg Cys Asn Ser Ser Ile Cys
145                 150                 155                 160

Ile Pro Ser Leu Trp Ala Cys Asp Gly Asp Val Asp Cys Val Asp Gly
                165                 170                 175

Ser Asp Glu Trp Pro Gln Asn Cys Gln Gly Arg Asp Thr Ala Ser Lys
                180                 185                 190

Gly Val Ser Ser Pro Cys Ser Ser Leu Glu Phe His Cys Gly Ser Ser
            195                 200                 205

Glu Cys Ile His Arg Ser Trp Val Cys Asp Gly Glu Ala Asp Cys Lys
210                 215                 220

Asp Lys Ser Asp Glu Glu His Cys Ala Val Ala Thr Cys Arg Pro Asp
225                 230                 235                 240

Glu Phe Gln Cys Ala Asp Gly Ser Cys Ile His Gly Ser Arg Gln Cys
                245                 250                 255

Asp Arg Glu His Asp Cys Lys Asp Met Ser Asp Glu Leu Gly Cys Val
            260                 265                 270

Asn Val Thr Gln Cys Asp Gly Pro Asn Lys Phe Lys Cys His Ser Gly
        275                 280                 285

Glu Cys Ile Ser Leu Asp Lys Val Cys Asp Ser Ala Arg Asp Cys Gln
    290                 295                 300

Asp Trp Ser Asp Glu Pro Ile Lys Glu Cys Lys Thr Asn Glu Cys Leu
305                 310                 315                 320

Asp Asn Asn Gly Gly Cys Ser His Ile Cys Lys Asp Leu Lys Ile Gly
                325                 330                 335

Ser Glu Cys Leu Cys Pro Ser Gly Phe Arg Leu Val Asp Leu His Arg
            340                 345                 350
```

```
Cys Glu Asp Ile Asp Glu Cys Gln Glu Pro Asp Thr Cys Ser Gln Leu
            355                 360                 365

Cys Val Asn Leu Glu Gly Ser Tyr Lys Cys Glu Cys Gln Ala Gly Phe
    370                 375                 380

His Met Asp Pro His Thr Arg Val Cys Lys Ala Val Gly Ser Ile Gly
385                 390                 395                 400

Tyr Leu Leu Phe Thr Asn Arg His Glu Val Arg Lys Met Thr Leu Asp
                405                 410                 415

Arg Ser Glu Tyr Thr Ser Leu Leu Pro Asn Leu Lys Asn Val Val Ala
            420                 425                 430

Leu Asp Thr Glu Val Thr Asn Asn Arg Ile Tyr Trp Ser Asp Leu Ser
            435                 440                 445

Gln Lys Lys Ile Tyr Ser Ala Leu Met Asp Gln Ala Pro Asn Leu Ser
            450                 455                 460

Tyr Asp Thr Ile Ile Ser Glu Asp Leu His Ala Pro Asp Gly Leu Ala
465                 470                 475                 480

Val Asp Trp Ile His Arg Asn Ile Tyr Trp Thr Asp Ser Val Pro Gly
            485                 490                 495

Ser Val Ser Val Ala Asp Thr Lys Gly Val Lys Arg Arg Thr Leu Phe
            500                 505                 510

Gln Glu Ala Gly Ser Arg Pro Arg Ala Ile Val Val Asp Pro Val His
            515                 520                 525

Gly Phe Met Tyr Trp Thr Asp Trp Gly Thr Pro Ala Lys Ile Lys Lys
            530                 535                 540

Gly Gly Leu Asn Gly Val Asp Ile His Ser Leu Val Thr Glu Asn Ile
545                 550                 555                 560

Gln Trp Pro Asn Gly Ile Thr Leu Asp Leu Ser Ser Gly Arg Leu Tyr
            565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Asn Arg Leu Ala His Pro
            595                 600                 605

Phe Ser Leu Ala Ile Tyr Glu Asp Lys Val Tyr Trp Thr Asp Val Ile
610                 615                 620

Asn Glu Ala Ile Phe Ser Ala Asn Arg Leu Thr Gly Ser Asp Val Asn
625                 630                 635                 640

Leu Val Ala Glu Asn Leu Leu Ser Pro Glu Asp Ile Val Leu Phe His
                645                 650                 655

Lys Val Thr Gln Pro Arg Gly Val Asn Trp Cys Glu Thr Thr Ala Leu
            660                 665                 670

Leu Pro Asn Gly Gly Cys Gln Tyr Leu Cys Leu Pro Ala Pro Gln Ile
            675                 680                 685

Gly Pro His Ser Pro Lys Phe Thr Cys Ala Cys Pro Asp Gly Met Leu
            690                 695                 700

Leu Ala Lys Asp Met Arg Ser Cys Leu Thr Glu Val Asp Thr Val Leu
705                 710                 715                 720

Thr Thr Gln Gly Thr Ser Ala Val Arg Pro Val Val Thr Ala Ser Ala
                725                 730                 735

Thr Arg Pro Pro Lys His Ser Glu Asp Leu Ser Ala Pro Ser Thr Pro
            740                 745                 750

Arg Gln Pro Val Asp Thr Pro Gly Leu Ser Thr Val Ala Ser Val Thr
            755                 760                 765

Val Ser His Gln Val Gln Gly Asp Met Ala Gly Arg Gly Asn Glu Glu
```

-continued

```
                770                 775                 780
Gln Pro His Gly Met Arg Phe Leu Ser Ile Phe Pro Ile Ala Leu
785                 790                 795                 800

Val Ala Leu Leu Val Leu Gly Ala Val Leu Leu Trp Arg Asn Trp Arg
                805                 810                 815

Leu Lys Asn Ile Asn Ser Ile Asn Phe Asp Asn Pro Val Tyr Gln Lys
                820                 825                 830

Thr Thr Glu Asp Glu Leu His Ile Cys Arg Ser Gln Asp Gly Tyr Thr
                835                 840                 845

Tyr Pro Ser Arg Gln Met Val Ser Leu Glu Asp Asp Val Ala
850                 855                 860

<210> SEQ ID NO 21
<211> LENGTH: 865
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 2, 3, 4, 5, 6, 7, 8, 11, 21, 24, 26, 27, 28, 35, 42, 50,
      53, 60, 61, 69, 71, 72, 80, 85, 86, 98, 117, 124, 130, 142,
      145, 146, 152, 154, 156, 159, 163, 169, 171, 174, 178, 183,
      185, 187, 188, 189, 190, 191, 192, 194, 201, 206, 208
<223> OTHER INFORMATION: Xaa = Any Amino Acid or No Amino Acid
<220> FEATURE:
<221> NAME/KEY: VARIANT
<222> LOCATION: 213, 216, 220, 221, 231, 248, 276, 298, 299, 304, 315,
      331, 337, 343, 346, 349, 350, 351, 375, 379, 381, 382, 385, 392,
      403, 438, 439, 451, 453, 455, 456, 459, 461, 462, 465, 472,
      475, 487, 496, 514, 516, 572, 604, 658, 670, 672, 674
<223> OTHER INFORMATION: Xaa = Any Amino Acid or No Amino Acid
<220> FEATURE:
<221> NAME/KEY: VARIANT
<222> LOCATION: 675, 690, 717, 719, 720, 722, 725, 728, 731, 732, 738,
      740, 741, 742, 745, 746, 747, 748, 749, 751, 753, 755, 757, 758,
      766, 767, 774, 775, 785, 786, 788, 789, 792, 796, 797, 800,
      803, 804, 806, 809, 810, 821, 822, 845, 846
<223> OTHER INFORMATION: Xaa = Any Amino Acid or No Amino Acid

<400> SEQUENCE: 21

Met Xaa Xaa Xaa Xaa Xaa Xaa Arg Trp Xaa Ile Ala Leu Leu Leu
1               5                   10                  15

Ala Ala Ala Gly Xaa Ala Val Xaa Asp Xaa Xaa Xaa Arg Asn Glu Phe
                20                  25                  30

Gln Cys Xaa Asp Gly Lys Cys Ile Ala Xaa Lys Trp Val Cys Asp Gly
                35                  40                  45

Ser Xaa Glu Cys Xaa Asp Gly Ser Asp Glu Ser Xaa Xaa Thr Cys Leu
50                  55                  60

Ser Val Thr Cys Xaa Ser Xaa Xaa Phe Ser Cys Gly Gly Arg Val Xaa
65                  70                  75                  80

Arg Cys Ile Pro Xaa Xaa Trp Arg Cys Asp Gly Gln Val Asp Cys Asp
                85                  90                  95

Asn Xaa Xaa Asp Glu Gln Gly Cys Pro Pro Lys Thr Cys Ser Gln Asp
                100                 105                 110

Asp Phe Arg Cys Xaa Asp Gly Lys Cys Ile Ser Xaa Gln Phe Val Cys
                115                 120                 125

Asp Xaa Asp Arg Asp Cys Leu Asp Gly Ser Asp Glu Ala Xaa Cys Pro
                130                 135                 140

Xaa Xaa Thr Cys Gly Pro Ala Xaa Phe Xaa Cys Xaa Ser Ser Xaa Cys
145                 150                 155                 160

Ile Pro Xaa Leu Trp Ala Cys Asp Xaa Asp Xaa Asp Cys Xaa Asp Gly
```

```
            165                 170                 175
Ser Xaa Glu Trp Pro Gln Xaa Cys Xaa Ala Xaa Xaa Xaa Xaa Xaa Xaa
            180                 185                 190

Gly Xaa Ser Ser Pro Cys Ser Ala Xaa Glu Phe His Cys Xaa Ser Xaa
            195                 200                 205

Glu Cys Ile His Xaa Ser Trp Xaa Cys Asp Gly Xaa Xaa Asp Cys Lys
            210                 215                 220

Asp Lys Ser Asp Glu Glu Xaa Cys Ala Val Ala Thr Cys Arg Pro Asp
225                 230                 235                 240

Glu Phe Gln Cys Ala Asp Gly Xaa Cys Ile His Gly Ser Arg Gln Cys
                245                 250                 255

Asp Arg Glu His Asp Cys Lys Asp Met Ser Asp Glu Leu Gly Cys Val
            260                 265                 270

Asn Val Thr Xaa Cys Asp Gly Pro Asn Lys Phe Lys Cys His Ser Gly
            275                 280                 285

Glu Cys Ile Ser Leu Asp Lys Val Cys Xaa Xaa Ala Arg Asp Cys Xaa
            290                 295                 300

Asp Trp Ser Asp Glu Pro Ile Lys Glu Cys Xaa Thr Asn Glu Cys Leu
305                 310                 315                 320

Asp Asn Asn Gly Gly Cys Ser His Ile Cys Xaa Asp Leu Lys Ile Gly
                325                 330                 335

Xaa Glu Cys Leu Cys Pro Xaa Gly Phe Xaa Leu Val Xaa Xaa Xaa Arg
            340                 345                 350

Cys Glu Asp Ile Asp Glu Cys Gln Asp Pro Asp Thr Cys Ser Gln Leu
            355                 360                 365

Cys Val Asn Leu Glu Gly Xaa Tyr Lys Cys Xaa Cys Xaa Xaa Gly Phe
            370                 375                 380

Xaa Leu Asp Pro His Thr Lys Xaa Cys Lys Ala Val Gly Ser Ile Ala
385                 390                 395                 400

Tyr Leu Xaa Phe Thr Asn Arg His Glu Val Arg Lys Met Thr Leu Asp
                405                 410                 415

Arg Ser Glu Tyr Thr Ser Leu Ile Pro Asn Leu Lys Asn Val Val Ala
            420                 425                 430

Leu Asp Thr Glu Val Xaa Xaa Asn Arg Ile Tyr Trp Ser Asp Leu Ser
            435                 440                 445

Gln Lys Xaa Ile Xaa Ser Xaa Xaa Leu Asp Xaa Ala Xaa Xaa Leu Ser
            450                 455                 460

Xaa Tyr Asp Thr Ile Ile Ser Xaa Asp Ile Xaa Ala Pro Asp Gly Leu
465                 470                 475                 480

Ala Val Asp Trp Ile His Xaa Asn Ile Tyr Trp Thr Asp Ser Val Xaa
                485                 490                 495

Gly Ser Val Ser Val Ala Asp Thr Lys Gly Val Lys Arg Lys Thr Leu
            500                 505                 510

Phe Xaa Glu Xaa Gly Ser Lys Pro Arg Ala Ile Val Val Asp Pro Val
            515                 520                 525

His Gly Phe Met Tyr Trp Thr Asp Trp Gly Thr Pro Ala Lys Ile Lys
            530                 535                 540

Lys Gly Gly Leu Asn Gly Val Asp Ile His Ser Leu Val Thr Glu Asn
545                 550                 555                 560

Ile Gln Trp Pro Asn Gly Ile Thr Leu Asp Leu Xaa Ser Gly Arg Leu
                565                 570                 575

Tyr Trp Val Asp Ser Lys Leu His Ser Ile Ser Ser Ile Asp Val Asn
            580                 585                 590
```

Gly Gly Asn Arg Lys Thr Ile Leu Glu Asp Glu Xaa Arg Leu Ala His
            595                 600                 605

Pro Phe Ser Leu Ala Ile Phe Glu Asp Lys Val Phe Trp Thr Asp Ile
        610                 615                 620

Ile Asn Glu Ala Ile Phe Ser Ala Asn Arg Leu Thr Gly Ser Asp Val
625                 630                 635                 640

Asn Leu Leu Ala Glu Asn Leu Leu Ser Pro Glu Asp Ile Val Leu Phe
                645                 650                 655

His Xaa Leu Thr Gln Pro Arg Gly Val Asn Trp Cys Glu Xaa Thr Xaa
            660                 665                 670

Leu Xaa Xaa Asn Gly Gly Cys Gln Tyr Leu Cys Leu Pro Ala Pro Gln
        675                 680                 685

Ile Xaa Pro His Ser Pro Lys Phe Thr Cys Ala Cys Pro Asp Gly Met
    690                 695                 700

Leu Leu Ala Lys Asp Met Arg Ser Cys Leu Thr Glu Xaa Asp Xaa Xaa
705                 710                 715                 720

Leu Xaa Thr Gln Xaa Thr Ser Xaa Val Arg Xaa Xaa Val Ser Ala Ser
                725                 730                 735

Ala Xaa Arg Xaa Xaa Xaa His Ser Xaa Xaa Xaa Xaa Pro Xaa Thr
            740                 745                 750

Xaa Arg Xaa Pro Xaa Xaa Thr Pro Gly Leu Ser Thr Val Xaa Xaa Val
        755                 760                 765

Thr Met Ser His Gln Xaa Xaa Gly Asp Met Ala Gly Arg Gly Asn Glu
    770                 775                 780

Xaa Xaa Pro Xaa Xaa Met Arg Xaa Leu Ser Ile Xaa Xaa Pro Ile Xaa
785                 790                 795                 800

Leu Leu Xaa Xaa Leu Xaa Leu Gly Xaa Xaa Leu Leu Trp Lys Asn Trp
                805                 810                 815

Arg Leu Lys Asn Xaa Xaa Ile Asn Ser Ile Asn Phe Asp Asn Pro Val
            820                 825                 830

Tyr Gln Lys Thr Thr Glu Asp Glu Leu His Ile Cys Xaa Xaa Gln Asp
        835                 840                 845

Gly Tyr Ser Tyr Pro Ser Arg Gln Met Val Ser Leu Glu Asp Asp Val
    850                 855                 860

Ala
865

<210> SEQ ID NO 22
<211> LENGTH: 860
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 2, 14, 20, 21, 35, 92, 103, 123, 183, 185, 188, 190,
      191, 192, 205, 213, 232, 247, 374, 402, 452, 461, 561, 570, 571,
      603, 690, 697, 730, 734, 737, 748, 751, 762, 764, 785, 788,
      796, 806, 817, 840
<223> OTHER INFORMATION: Xaa = Any Amino Acid or No Amino Acid

<400> SEQUENCE: 22

Met Xaa Pro Trp Gly Trp Lys Leu Arg Trp Thr Val Ala Xaa Leu Leu
1               5                   10                  15

Ala Ala Ala Xaa Xaa Ala Val Gly Asp Arg Cys Glu Arg Asn Glu Phe
                20                  25                  30

Gln Cys Xaa Asp Gly Lys Cys Ile Ser Tyr Lys Trp Val Cys Asp Gly

```
            35                  40                  45
Ser Ala Glu Cys Gln Asp Gly Ser Asp Glu Ser Gln Glu Thr Cys Leu
 50                  55                  60
Ser Val Thr Cys Lys Ser Gly Asp Phe Ser Cys Gly Gly Arg Val Asn
 65                  70                  75                  80
Arg Cys Ile Pro Gln Phe Trp Arg Cys Asp Gly Xaa Val Asp Cys Asp
                     85                  90                  95
Asn Gly Ser Asp Glu Gln Xaa Cys Pro Pro Lys Thr Cys Ser Gln Asp
                100                 105                 110
Glu Phe Arg Cys His Asp Gly Lys Cys Ile Xaa Arg Gln Phe Val Cys
                115                 120                 125
Asp Ser Asp Arg Asp Cys Leu Asp Gly Ser Asp Glu Ala Ser Cys Pro
                130                 135                 140
Val Leu Thr Cys Gly Pro Ala Ser Phe Gln Cys Asn Ser Ser Thr Cys
145                 150                 155                 160
Ile Pro Gln Leu Trp Ala Cys Asp Asn Asp Pro Asp Cys Glu Asp Gly
                165                 170                 175
Ser Asp Glu Trp Pro Gln Xaa Cys Xaa Gly Leu Xaa Val Xaa Xaa Xaa
                180                 185                 190
Asp Ser Ser Pro Cys Ser Ala Phe Glu Phe His Cys Xaa Ser Gly Glu
                195                 200                 205
Cys Ile His Ser Xaa Trp Arg Cys Asp Gly Pro Asp Cys Lys Asp
                210                 215                 220
Lys Ser Asp Glu Glu Asn Cys Xaa Val Ala Thr Cys Arg Pro Asp Glu
225                 230                 235                 240
Phe Gln Cys Ser Asp Gly Xaa Cys Ile His Gly Ser Arg Gln Cys Asp
                245                 250                 255
Arg Glu Tyr Asp Cys Lys Asp Met Ser Asp Glu Val Gly Cys Ile Asn
                260                 265                 270
Val Thr Leu Cys Glu Gly Pro Asn Lys Phe Lys Cys His Ser Gly Glu
                275                 280                 285
Cys Ile Ser Leu Asp Lys Val Cys Asn Met Ala Arg Asp Cys Arg Asp
                290                 295                 300
Trp Ser Asp Glu Pro Ile Lys Glu Cys Gly Thr Asn Glu Cys Leu Asp
305                 310                 315                 320
Asn Asn Gly Gly Cys Ser His Ile Cys Asn Asp Leu Lys Ile Gly Tyr
                325                 330                 335
Glu Cys Leu Cys Pro Asp Gly Phe Gln Leu Val Ala Gln Arg Arg Cys
                340                 345                 350
Glu Asp Ile Asp Glu Cys Gln Asp Pro Asp Thr Cys Ser Gln Leu Cys
                355                 360                 365
Val Asn Leu Glu Gly Xaa Tyr Lys Cys Gln Cys Glu Glu Gly Phe Gln
                370                 375                 380
Leu Asp Pro His Thr Lys Ala Cys Lys Ala Val Gly Ser Ile Ala Tyr
385                 390                 395                 400
Leu Xaa Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
                420                 425                 430
Asp Thr Glu Val Ala Ser Asn Arg Ile Tyr Trp Ser Asp Leu Ser Gln
                435                 440                 445
Arg Met Ile Xaa Ser Thr Gln Leu Asp Arg Ala His Xaa Val Ser Ser
                450                 455                 460
```

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Xaa Trp Pro Asn Gly Ile Thr Leu Asp Xaa Xaa Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Xaa Arg Leu Ala His Pro
        595                 600                 605

Phe Ser Leu Ala Ile Phe Glu Asp Lys Val Phe Trp Thr Asp Ile Ile
    610                 615                 620

Asn Glu Ala Ile Phe Ser Ala Asn Arg Leu Thr Gly Ser Asp Ile Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro Xaa Ser Pro Lys Phe Thr Cys Xaa Cys Pro Asp Gly Met Leu Leu
    690                 695                 700

Ala Lys Asp Met Arg Ser Cys Leu Thr Glu Ala Glu Ala Val Ala
705                 710                 715                 720

Thr Gln Glu Thr Ser Thr Val Arg Leu Xaa Val Ser Ser Xaa Ala Val
                725                 730                 735

Xaa Thr Gln His Thr Thr Thr Arg Pro Val Pro Xaa Thr Ser Xaa Leu
                740                 745                 750

Pro Gly Ala Thr Pro Gly Leu Thr Thr Xaa Glu Xaa Val Thr Met Ser
    755                 760                 765

His Gln Ala Leu Gly Asp Val Ala Gly Arg Gly Asn Glu Lys Lys Pro
    770                 775                 780

Xaa Ser Val Xaa Ala Leu Ser Ile Val Leu Pro Xaa Val Leu Leu Val
785                 790                 795                 800

Phe Leu Cys Leu Gly Xaa Phe Leu Leu Trp Lys Asn Trp Arg Leu Lys
                805                 810                 815

Xaa Ile Asn Ser Ile Asn Phe Asp Asn Pro Val Tyr Gln Lys Thr Thr
            820                 825                 830

Glu Asp Glu Val His Ile Cys Xaa Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 23
<211> LENGTH: 672

<212> TYPE: PRT
<213> ORGANISM: Homo sapiens

<400> SEQUENCE: 23

```
Gln Glu Asp Glu Asp Gly Asp Tyr Glu Glu Leu Val Leu Ala Leu Arg
 1               5                  10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400
```

-continued

```
Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
        450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
        530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Gly Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln Gly Pro His His His His His His
            660                 665                 670

<210> SEQ ID NO 24
<211> LENGTH: 699
<212> TYPE: PRT
<213> ORGANISM: Homo sapiens

<400> SEQUENCE: 24

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
```

```
              100                 105                 110
His Val Phe His Leu Leu Pro Gly Phe Leu Val Lys Met Ser Gly Asp
            115                 120                 125

Leu Leu Glu Leu Ala Leu Lys Leu Pro His Val Asp Tyr Ile Glu Glu
130                 135                 140

Asp Ser Ser Val Phe Ala Gln Ser Ile Pro Trp Asn Leu Glu Arg Ile
145                 150                 155                 160

Thr Pro Pro Arg Tyr Arg Ala Asp Glu Tyr Gln Pro Pro Asp Gly Gly
                165                 170                 175

Ser Leu Val Glu Val Tyr Leu Leu Asp Thr Ser Ile Gln Ser Asp His
            180                 185                 190

Arg Glu Ile Glu Gly Arg Val Met Val Thr Asp Phe Glu Asn Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Ala Ser Met Arg Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Val Gln Pro Val Pro Leu Val Val Leu Pro Leu Ala
        275                 280                 285

Gly Gly Tyr Ser Arg Val Leu Asn Ala Ala Cys Gln Arg Leu Ala Arg
    290                 295                 300

Ala Gly Val Val Leu Val Thr Ala Ala Gly Asn Phe Arg Asp Asp Ala
305                 310                 315                 320

Cys Leu Tyr Ser Pro Ala Ser Ala Pro Glu Val Ile Thr Val Gly Ala
                325                 330                 335

Thr Asn Ala Gln Asp Gln Pro Val Thr Leu Gly Thr Leu Gly Thr Asn
            340                 345                 350

Phe Gly Arg Cys Val Asp Leu Phe Ala Pro Gly Glu Asp Ile Ile Gly
        355                 360                 365

Ala Ser Ser Asp Cys Ser Thr Cys Phe Val Ser Gln Ser Gly Thr Ser
    370                 375                 380

Gln Ala Ala Ala His Val Ala Gly Ile Ala Ala Met Met Leu Ser Ala
385                 390                 395                 400

Glu Pro Glu Leu Thr Leu Ala Glu Leu Arg Gln Leu Ile His Phe Ser
                405                 410                 415

Ala Lys Asp Val Ile Asn Glu Ala Trp Phe Pro Glu Asp Gln Arg Val
            420                 425                 430

Leu Thr Pro Asn Leu Val Ala Ala Leu Pro Pro Ser Thr His Gly Ala
        435                 440                 445

Gly Trp Gln Leu Phe Cys Arg Thr Val Trp Ser Ala His Ser Gly Pro
    450                 455                 460

Thr Arg Met Ala Thr Ala Ile Ala Arg Cys Ala Pro Asp Glu Glu Leu
465                 470                 475                 480

Leu Ser Cys Ser Ser Phe Ser Arg Ser Gly Lys Arg Arg Gly Glu Arg
                485                 490                 495

Met Glu Ala Gln Gly Gly Lys Leu Val Cys Arg Ala His Asn Ala Phe
            500                 505                 510

Gly Gly Glu Gly Val Tyr Ala Ile Ala Arg Cys Cys Leu Leu Pro Gln
        515                 520                 525
```

Ala Asn Cys Ser Val His Thr Ala Pro Pro Ala Glu Ala Ser Met Gly
            530                 535                 540

Thr Arg Val His Cys His Gln Gln Gly His Val Leu Thr Gly Cys Ser
545                 550                 555                 560

Ser His Trp Glu Val Glu Asp Leu Gly Thr His Lys Pro Pro Val Leu
                565                 570                 575

Arg Pro Arg Gly Gln Pro Asn Gln Cys Val Gly His Arg Glu Ala Ser
                580                 585                 590

Ile His Ala Ser Cys Cys His Ala Pro Gly Leu Glu Cys Lys Val Lys
            595                 600                 605

Glu His Gly Ile Pro Ala Pro Gln Glu Gln Val Thr Val Ala Cys Glu
        610                 615                 620

Glu Gly Trp Thr Leu Thr Gly Cys Ser Ala Leu Pro Gly Thr Ser His
625                 630                 635                 640

Val Leu Gly Ala Tyr Ala Val Asp Asn Thr Cys Val Val Arg Ser Arg
                645                 650                 655

Asp Val Ser Thr Thr Gly Ser Thr Ser Glu Glu Ala Val Thr Ala Val
            660                 665                 670

Ala Ile Cys Cys Arg Ser Arg His Leu Ala Gln Ala Ser Gln Glu Leu
        675                 680                 685

Gln Gly Pro His His His His His His His
    690                 695

<210> SEQ ID NO 25
<211> LENGTH: 686
<212> TYPE: PRT
<213> ORGANISM: Cavia porcellus

<400> SEQUENCE: 25

Met Arg Thr Arg Gly Pro Ala Pro Ala Trp Trp Pro Met Leu Leu Leu
1               5                   10                  15

Leu Met Leu Gly Pro Ala Pro Ala Gly Ala Gln Ala Arg Asp Ser Glu
                20                  25                  30

Asp Gly Asp His Glu Gly Leu Ala Phe Ala Phe Pro Pro Glu Glu Asp
            35                  40                  45

Gly Pro Ala Glu Ala Ala Pro His Val Pro Thr Ala Pro Phe His Arg
    50                  55                  60

Cys Ser Lys Asp Ala Trp Arg Leu Pro Gly Thr Tyr Leu Val Val Leu
65                  70                  75                  80

Lys Glu Gly Thr His Arg Gly Gln Thr Lys His Thr Ala His Arg Leu
                85                  90                  95

Gln Ala Lys Ala Ala Arg Arg Gly Tyr Val Thr Thr Val Leu His Leu
                100                 105                 110

Phe His His Leu Val Pro Gly Phe Leu Val Arg Met Ser Gly Asp Leu
            115                 120                 125

Leu Asp Met Ala Leu Arg Leu Pro Leu Val Gln Tyr Ile Glu Glu Asp
    130                 135                 140

Ser Ser Val Phe Ala Gln Ser Val Pro Trp Asn Leu Glu Arg Ile Leu
145                 150                 155                 160

Pro Val Arg His Gln Ala Lys Glu Tyr Ser Ala Pro Ser His Pro Val
                165                 170                 175

Thr Val Tyr Leu Leu Asp Thr Ser Ile Gln Ser Gly His Arg Glu Ile
            180                 185                 190

Gln Gly Arg Ile Thr Val Thr Asp Phe Glu Ser Val Pro Gln Glu Asp

```
            195                 200                 205
Gly Thr Arg Phe His Arg Gln Ala Ser Lys Cys Asp Ser His Gly Thr
210                 215                 220
His Leu Ala Gly Val Val Ser Gly Arg Asp Ala Gly Val Ala Lys Gly
225                 230                 235                 240
Ala Gly Leu Arg Ser Leu Arg Val Leu Asn Cys Gln Gly Arg Gly Thr
                245                 250                 255
Val Ser Ser Thr Leu Arg Gly Leu Glu Phe Ile Arg Lys Ser Gln Leu
            260                 265                 270
Ala Gln Pro Val Glu Pro Leu Val Leu Pro Leu Ala Gly Gly
        275                 280                 285
Tyr Ser Arg Thr Leu Asn Ala Ala Cys His Leu Leu Ala Arg Ala Gly
        290                 295                 300
Val Val Leu Val Ala Ala Ala Gly Asn Phe Arg Asp Asp Ala Cys Leu
305                 310                 315                 320
Tyr Ser Pro Ala Ser Ala Pro Glu Val Ile Thr Val Gly Ala Thr Asn
                325                 330                 335
Ala Gln Asp Gln Pro Val Thr Leu Gly Thr Leu Gly Thr Asn Phe Gly
            340                 345                 350
Arg Cys Val Asp Leu Phe Ala Pro Gly Glu Asp Ile Ile Gly Ala Ser
        355                 360                 365
Ser Asp Cys Ser Thr Cys Phe Val Ser Arg Ser Gly Thr Ser Gln Ala
370                 375                 380
Ala Ala His Val Ala Gly Ile Val Thr Met Met Leu Thr Ala Gln Pro
385                 390                 395                 400
Lys Leu Thr Leu Ala Glu Leu Trp Gln Arg Leu Ile His Phe Ala Ala
                405                 410                 415
Lys Asp Val Ile Asn Glu Ala Trp Phe Pro Glu Asp Gln Arg Val Leu
            420                 425                 430
Thr Pro Asn Leu Val Ala Thr Leu Pro Pro Ser Thr Arg Gly Ala Gly
        435                 440                 445
Gly Arg Leu Leu Cys Arg Thr Val Trp Ser Ala Arg Ser Gly Pro Arg
    450                 455                 460
His Thr Ala Thr Ala Leu Ala His Cys Thr Pro Gly Glu Glu Leu Leu
465                 470                 475                 480
Ser Cys Ser Ser Phe Ser Arg Ser Gly Lys Arg Lys Gly Glu Arg Ile
                485                 490                 495
Glu Val Leu Arg Gly Arg Val Cys Val Ala Tyr Asn Ala Phe Gly
            500                 505                 510
Gly Lys Gly Val His Ala Val Ala Arg Cys Cys Leu Leu Pro Arg Ala
        515                 520                 525
Asn Cys Ser Leu His Thr Ala Pro Ala Arg Ala Gly Met Glu Pro Arg
    530                 535                 540
Val His Cys His Arg Lys Asp Gln Val Leu Thr Gly Cys Ser Ala His
545                 550                 555                 560
Trp Glu Ala Glu Asp Phe Arg Ala Arg Gly Trp Pro Met Leu Arg Pro
                565                 570                 575
Gly Gly Pro Ser Gln Cys Val Gly His Ser Lys Ala Ser Val His Ala
            580                 585                 590
Ser Cys Cys Ser Ala Pro Gly Leu Glu Cys Arg Ile Arg Glu His Gly
        595                 600                 605
Val Pro Trp Pro Ala Glu Gln Val Thr Val Ala Cys Glu Asp Gly Trp
    610                 615                 620
```

```
Thr Leu Thr Gly Cys Ser Thr Leu Pro Gly Ala Ser Ser Val Leu Gly
625                 630                 635                 640

Thr Tyr Ala Val Asp Asp Met Cys Val Val Arg Ser Arg Asp Val Lys
            645                 650                 655

Ala Leu Asp Arg Thr Arg Gly Glu Ala Leu Ala Ala Ile Ala Ile Cys
        660                 665                 670

Cys Arg Ser Gln Ala Ser Glu Gln Ala Ser Pro Glu Arg Gln
    675                 680                 685

<210> SEQ ID NO 26
<211> LENGTH: 698
<212> TYPE: PRT
<213> ORGANISM: Mesocricetus auratus

<400> SEQUENCE: 26

Met Gly Thr Ser Cys Ser Ala Arg Pro Arg Trp Leu Leu Ser Pro Leu
1               5                   10                  15

Leu Leu Leu Leu Leu Leu Leu Arg Tyr Met Gly Ala Ser Ala Gln Asp
                20                  25                  30

Glu Asp Ala Glu Tyr Glu Glu Leu Met Leu Thr Leu Gln Ser Gln Asp
            35                  40                  45

Asp Gly Leu Ala Asp Glu Thr Asp Glu Ala Pro Gln Gly Ala Thr Ala
    50                  55                  60

Ala Phe His Arg Cys Pro Glu Glu Ala Trp Arg Val Pro Gly Thr Tyr
65                  70                  75                  80

Ile Val Met Leu Ala Glu Glu Ala Gln Trp Val His Ile Glu Gln Thr
                85                  90                  95

Met His Arg Leu Gln Thr Gln Ala Ala Arg Arg Gly Tyr Val Ile Lys
            100                 105                 110

Ile Gln His Ile Phe Tyr Asp Phe Leu Pro Ala Phe Val Lys Met
        115                 120                 125

Ser Ser Asp Leu Leu Asp Leu Ala Leu Lys Leu Pro His Val Lys Tyr
    130                 135                 140

Ile Glu Glu Asp Ser Leu Val Phe Ala Gln Ser Ile Pro Trp Asn Leu
145                 150                 155                 160

Asp Arg Ile Ile Pro Ala Gly Arg Gln Ala Gln Glu Tyr Ser Ser Ser
                165                 170                 175

Arg Lys Val Pro Ser Gly Ser Gly Gln Val Glu Val Tyr Leu Leu Asp
            180                 185                 190

Thr Ser Ile Gln Ser Asp His Arg Glu Ile Glu Gly Arg Val Thr Val
        195                 200                 205

Thr Asp Phe Asn Ser Val Pro Glu Glu Asp Gly Thr Arg Phe His Arg
    210                 215                 220

Gln Ala Ser Lys Cys Asp Ser His Gly Thr His Leu Ala Gly Val Val
225                 230                 235                 240

Ser Gly Arg Asp Ala Gly Val Ala Lys Gly Thr Ile Leu His Gly Leu
                245                 250                 255

Arg Val Leu Asn Cys Gln Gly Lys Gly Ile Val Ser Gly Ile Leu Thr
            260                 265                 270

Gly Leu Glu Phe Ile Trp Lys Ser Gln Leu Met Gln Pro Ser Gly Pro
        275                 280                 285

Gln Val Val Leu Leu Pro Leu Ala Gly Arg Tyr Ser Arg Val Leu Asn
    290                 295                 300

Thr Ala Cys Gln His Leu Ala Arg Thr Gly Val Val Leu Val Ala Ala
```

```
            305                 310                 315                 320
Ala Gly Asn Phe Arg Asp Asp Ala Cys Leu Tyr Ser Pro Ala Ser Ala
                325                 330                 335

Pro Glu Val Ile Thr Val Gly Ala Thr Asp Val Gln Asp Gln Pro Val
                340                 345                 350

Thr Leu Gly Thr Leu Gly Thr Asn Phe Gly Arg Cys Val Asp Leu Phe
                355                 360                 365

Ala Pro Gly Lys Asp Ile Ile Gly Ala Ser Ser Asp Cys Ser Ala Cys
370                 375                 380

Phe Met Ser Gln Ser Gly Thr Ser Gln Ala Ala His Val Ala Gly
385                 390                 395                 400

Ile Val Ala Met Met Leu Thr Leu Glu Pro Glu Leu Thr Leu Thr Glu
                405                 410                 415

Leu Arg Gln Arg Leu Ile His Phe Ser Thr Lys Asp Ala Ile Asn Met
                420                 425                 430

Ala Trp Phe Pro Glu Asp Gln Arg Val Leu Thr Pro Asn Leu Val Ala
                435                 440                 445

Thr Leu Pro Pro Ser Thr His Gly Thr Gly Gly Gln Leu Leu Cys Arg
                450                 455                 460

Thr Val Trp Ser Ala His Ser Gly Pro Thr Arg Ala Ala Thr Ala Thr
465                 470                 475                 480

Ala Arg Cys Ala Pro Gly Glu Glu Leu Leu Ser Cys Ser Ser Phe Ser
                485                 490                 495

Arg Ser Gly Arg Arg Gly Asp Arg Ile Glu Ala Ala Gly Thr Gln
                500                 505                 510

Gln Val Cys Lys Ala Leu Asn Ala Phe Gly Glu Gly Val Tyr Ala
                515                 520                 525

Val Ala Arg Cys Cys Leu Leu Pro Arg Ala Asn Cys Ser Ile His Thr
                530                 535                 540

Thr Pro Ala Ala Arg Thr Ser Leu Glu Thr His Ala Cys His Gln
545                 550                 555                 560

Lys Asp His Val Leu Thr Gly Cys Ser Leu His Trp Glu Val Glu Gly
                565                 570                 575

Ile Gly Val Gln Pro Leu Ala Val Leu Arg Ser Arg His Gln Pro Gly
                580                 585                 590

Gln Cys Thr Gly His Arg Glu Ala Ser Val His Ala Ser Cys Cys His
                595                 600                 605

Ala Pro Gly Leu Glu Cys Lys Ile Lys Glu His Gly Ile Ser Gly Pro
610                 615                 620

Ala Glu Gln Val Thr Val Ala Cys Glu Ala Gly Trp Thr Leu Thr Gly
625                 630                 635                 640

Cys Asn Val Leu Pro Gly Ala Phe Ile Thr Leu Gly Ala Tyr Ala Val
                645                 650                 655

Asp Asn Thr Cys Val Ala Arg Ser Arg Val Thr Asp Thr Ala Gly Arg
                660                 665                 670

Thr Gly Glu Glu Ala Thr Val Ala Ala Ile Cys Cys Arg Asn Arg
                675                 680                 685

Pro Ser Ala Lys Ala Ser Trp Val His Gln
                690                 695

<210> SEQ ID NO 27
<211> LENGTH: 685
<212> TYPE: PRT
<213> ORGANISM: Mus musculus
```

<400> SEQUENCE: 27

```
Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
            50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
            115                 120                 125

Met Ser Ser Asp Leu Leu Gly Leu Ala Leu Lys Leu Pro His Val Glu
130                 135                 140

Tyr Ile Glu Glu Asp Ser Phe Val Phe Ala Gln Ser Ile Pro Trp Asn
145                 150                 155                 160

Leu Arg Ile Ile Pro Ala Trp His Gln Thr Glu Glu Asp Arg Ser Pro
                165                 170                 175

Asp Gly Ser Ser Gln Val Glu Val Tyr Leu Leu Asp Thr Ser Ile Gln
            180                 185                 190

Gly Ala His Arg Glu Ile Glu Gly Arg Val Thr Ile Thr Asp Phe Asn
            195                 200                 205

Ser Val Pro Glu Glu Asp Gly Thr Arg Phe His Arg Gln Ala Ser Lys
210                 215                 220

Cys Asp Ser His Gly Thr His Leu Ala Gly Val Val Ser Gly Arg Asp
225                 230                 235                 240

Ala Gly Val Ala Lys Gly Thr Ser Leu His Ser Leu Arg Val Leu Asn
                245                 250                 255

Cys Gln Gly Lys Gly Thr Val Ser Gly Thr Leu Ile Gly Leu Glu Phe
            260                 265                 270

Ile Arg Lys Ser Gln Leu Ile Gln Pro Ser Pro Leu Val Val Leu Pro
            275                 280                 285

Leu Ala Gly Gly Tyr Ser Arg Ile Leu Asn Ala Ala Cys Arg His Leu
290                 295                 300

Ala Arg Thr Gly Val Val Leu Val Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Lys Asp Ile
            355                 360                 365

Ile Gly Ala Ser Ser Asp Cys Ser Thr Cys Phe Met Ser Gln Ser Gly
            370                 375                 380

Thr Ser Gln Ala Ala Ala His Val Ala Gly Ile Val Ala Arg Met Leu
385                 390                 395                 400

Ser Arg Glu Pro Thr Leu Thr Leu Ala Leu Arg Gln Arg Ile His Phe
```

```
            405                 410                 415
Ser Thr Lys Asp Val Ile Asn Met Ala Trp Phe Pro Glu Asp Gln Gln
        420                 425                 430

Val Leu Thr Pro Asn Leu Val Ala Thr Leu Pro Pro Ser Thr His Glu
        435                 440                 445

Thr Gly Gly Gln Leu Leu Cys Arg Thr Val Trp Ser Ala His Ser Gly
        450                 455                 460

Pro Thr Arg Thr Ala Thr Ala Thr Ala Arg Cys Ala Pro Glu Glu Glu
465                 470                 475                 480

Leu Leu Ser Cys Ser Ser Phe Ser Arg Ser Gly Arg Arg Gly Asp
                485                 490                 495

Arg Ile Glu Ala Ile Gly Gly Gln Gln Val Cys Lys Ala Leu Asn Ala
                500                 505                 510

Phe Gly Gly Glu Gly Val Tyr Ala Val Ala Arg Cys Cys Leu Val Pro
                515                 520                 525

His Ala Asn Cys Ser Ile His Asn Pro Ala Ala Gly Leu Glu Thr
                530                 535                 540

His Val His Cys His Gln Lys Asp His Val Leu Thr Gly Cys Ser Phe
545                 550                 555                 560

His Trp Glu Val Glu Asp Leu Ser Val Arg Arg Gln Pro Ala Leu Arg
                565                 570                 575

Ser Arg Arg Gln Pro Gly Gln Cys Val Gly His Gln Ala Ala Ser Val
                580                 585                 590

Tyr Ala Ser Cys Cys His Ala Pro Gly Leu Glu Cys Lys Ile Lys Glu
                595                 600                 605

His Gly Ile Ser Gly Ser Glu Gln Val Thr Val Ala Cys Glu Ala
        610                 615                 620

Gly Trp Thr Leu Thr Gly Cys Asn Val Leu Pro Gly Ala Ser Leu Thr
625                 630                 635                 640

Leu Gly Ala Tyr Ser Val Asp Asn Leu Cys Val Ala Arg Val His Asp
                645                 650                 655

Thr Ala Arg Ala Asp Arg Thr Gly Glu Thr Val Ala Ala Ala Ile Cys
                660                 665                 670

Cys Arg Ser Arg Pro Ser Ala Lys Ala Ser Trp Val Gln
                675                 680                 685

<210> SEQ ID NO 28
<211> LENGTH: 683
<212> TYPE: PRT
<213> ORGANISM: Macaca fascicularis

<400> SEQUENCE: 28

Met Gly Thr Val Ser Ser Arg Arg Ser Trp Trp Pro Leu Pro Leu Pro
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
                35                  40                  45

Glu Asp Gly Leu Ala Asp Ala Pro Glu His Gly Ala Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Arg Ser Gln Ser Glu Arg Thr Ala Arg
                85                  90                  95
```

```
Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Glu Arg Ile
145                 150                 155                 160

Thr Pro Ala Arg Tyr Arg Ala Asp Glu Tyr Gln Pro Lys Gly Gly
                165                 170                 175

Ser Leu Val Glu Val Tyr Leu Leu Asp Thr Ser Ile Gln Ser Asp His
            180                 185                 190

Arg Glu Ile Glu Gly Arg Val Met Val Thr Asp Phe Glu Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Ala Gly Leu Arg Ser Leu Arg Val Leu Asn Cys Gln Gly
            245                 250                 255

Lys Gly Thr Val Ser Gly Thr Leu Ile Gly Leu Glu Phe Ile Arg Lys
        260                 265                 270

Ser Gln Leu Val Gln Pro Val Pro Leu Val Val Leu Pro Leu Ala Gly
    275                 280                 285

Gly Tyr Ser Arg Val Phe Asn Ala Ala Cys Gln Arg Leu Ala Arg Ala
290                 295                 300

Gly Val Val Leu Val Thr Ala Ala Gly Asn Phe Arg Asp Asp Ala Cys
305                 310                 315                 320

Leu Tyr Ser Pro Ala Ser Ala Pro Glu Val Ile Thr Val Gly Ala Thr
            325                 330                 335

Asn Ala Gln Asp Gln Pro Val Thr Leu Gly Thr Leu Gly Thr Asn Phe
        340                 345                 350

Gly Arg Cys Val Asp Leu Phe Ala Pro Gly Glu Asp Ile Ile Gly Ala
    355                 360                 365

Ser Ser Asp Cys Ser Thr Cys Phe Val Ser Arg Ser Gly Thr Ser Gln
370                 375                 380

Ala Ala His Val Ala Gly Ile Ala Ala Met Met Leu Ser Ala Glu
385                 390                 395                 400

Pro Glu Leu Thr Leu Ala Leu Arg Gln Leu Ile His Phe Ser Ala Lys
            405                 410                 415

Asp Val Ile Asn Glu Ala Trp Phe Pro Glu Asp Gln Arg Val Leu Thr
        420                 425                 430

Pro Asn Leu Val Ala Ala Leu Pro Pro Ser Thr His Arg Ala Gly Trp
    435                 440                 445

Gln Leu Phe Cys Arg Thr Val Trp Ser Ala His Ser Gly Pro Thr Arg
450                 455                 460

Met Ala Thr Ala Val Ala Arg Cys Ala Gln Asp Glu Glu Leu Leu Ser
465                 470                 475                 480

Cys Ser Ser Phe Ser Arg Ser Gly Lys Arg Arg Gly Glu Arg Ile Glu
            485                 490                 495

Ala Gln Gly Gly Lys Arg Val Cys Arg Ala His Asn Ala Phe Gly Gly
        500                 505                 510

Glu Gly Val Tyr Ala Ile Ala Arg Cys Cys Leu Leu Pro Gln Val Asn
```

```
            515                 520                 525
Cys Ser Val His Thr Pro Pro Gly Ala Ser Met Gly Thr Arg Val His
    530                 535                 540

Cys His Gln Gln Gly His Val Leu Thr Gly Cys Ser Ser His Trp Glu
545                 550                 555                 560

Val Glu Asp Leu Gly Thr His Lys Pro Pro Val Leu Arg Pro Arg Gly
                565                 570                 575

Gln Pro Asn Gln Cys Val Gly His Arg Glu Ala Ser Ile His Ala Ser
            580                 585                 590

Cys Cys His Ala Pro Gly Leu Glu Cys Lys Val Arg Glu His Gly Ile
        595                 600                 605

Pro Ala Pro Gln Glu Gln Val Ile Val Ala Cys Glu Asp Gly Trp Thr
    610                 615                 620

Leu Thr Gly Cys Ser Ala Leu Pro Gly Thr Ser His Val Leu Gly Ala
625                 630                 635                 640

Tyr Ala Val Asp Asn Thr Cys Val Val Arg Ser Arg Asp Val Ser Thr
                645                 650                 655

Thr Gly Ser Thr Glu Ala Val Ala Ala Val Ala Ile Cys Cys Arg Ser
            660                 665                 670

Arg His Leu Val Gln Ala Ser Gln Glu Leu Gln
        675                 680

<210> SEQ ID NO 29
<211> LENGTH: 691
<212> TYPE: PRT
<213> ORGANISM: Rattus norvegicus

<400> SEQUENCE: 29

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp
                20                  25                  30

Glu Asp Gly Asp Tyr Glu Glu Leu Met Leu Ala Leu Pro Ser Gln Glu
            35                  40                  45

Asp Ser Leu Val Asp Glu Ala Ser His Val Ala Thr Ala Thr Phe Arg
    50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Arg Gly Tyr Val Ile Lys Val Leu His
            100                 105                 110

Val Phe Tyr Asp Leu Phe Pro Gly Phe Leu Val Lys Met Ser Ser Asp
    115                 120                 125

Leu Leu Gly Leu Ala Leu Lys Leu Pro His Val Glu Tyr Ile Glu Glu
130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205
```

-continued

```
Glu Glu Asp Gly Thr Arg Phe His Arg Gln Ala Ser Lys Cys Asp Ser
210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
                260                 265                 270

Ser Gln Leu Ile Gln Pro Ser Gly Pro Leu Val Val Leu Leu Pro Leu
                275                 280                 285

Ala Gly Gly Tyr Ser Arg Ile Leu Asn Thr Ala Cys Gln Arg Leu Ala
290                 295                 300

Arg Thr Gly Val Val Leu Val Ala Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
                340                 345                 350

Asn Phe Gly Arg Cys Val Asp Leu Phe Ala Pro Gly Lys Asp Ile Ile
                355                 360                 365

Gly Ala Ser Ser Asp Cys Ser Thr Cys Tyr Met Ser Gln Ser Gly Thr
370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415

Phe Ser Thr Lys Asp Val Ile Asn Met Ala Trp Phe Pro Glu Asp Gln
                420                 425                 430

Arg Val Leu Thr Pro Asn Arg Val Ala Thr Leu Pro Pro Ser Thr Gln
                435                 440                 445

Glu Thr Gly Gly Gln Leu Leu Cys Arg Thr Val Trp Ser Ala His Ser
450                 455                 460

Gly Pro Thr Arg Thr Ala Thr Ala Thr Arg Cys Ala Pro Glu Glu
465                 470                 475                 480

Glu Leu Leu Ser Cys Ser Ser Phe Ser Arg Ser Gly Arg Arg Gly
                485                 490                 495

Asp Arg Ile Glu Ala Ile Gly Gly Gln Gln Val Cys Lys Ala Leu Asn
                500                 505                 510

Ala Phe Gly Gly Glu Gly Val Tyr Ala Val Ala Arg Cys Cys Leu Leu
                515                 520                 525

Pro Arg Val Asn Cys Ser Ile His Asn Thr Pro Ala Ala Arg Ala Gly
                530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Pro
                565                 570                 575

Leu Leu Arg Ser Arg His Gln Pro Gly Gln Cys Val Gly His Gln Glu
                580                 585                 590

Ala Ser Val His Ala Ser Cys Cys His Ala Pro Gly Leu Glu Cys Lys
                595                 600                 605

Ile Lys Glu His Gly Ile Ala Gly Pro Ala Glu Gln Val Thr Val Ala
610                 615                 620
```

-continued

```
Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln
    690

<210> SEQ ID NO 30
<211> LENGTH: 702
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4, 14, 15, 16, 17, 18, 63, 64, 65, 180, 181, 182, 183,
      583, 584, 586, 701
<223> OTHER INFORMATION: Xaa = Any Amino Acid or No Amino Acid

<400> SEQUENCE: 30

Met Gly Thr Xaa Cys Ser Ala Arg Ser Trp Trp Pro Leu Xaa Xaa Xaa
1               5                   10                  15

Xaa Xaa Pro Leu Leu Leu Leu Leu Leu Pro Ala Gly Ala Ala
            20                  25                  30

Ala Ala Gln Asp Glu Asp Gly Asp Tyr Glu Glu Leu Met Leu Ala Leu
        35                  40                  45

Pro Ser Gln Glu Asp Gly Leu Ala Asp Glu Ala His Val Xaa Xaa
    50                  55                  60

Xaa Ala Thr Ala Thr Phe His Arg Cys Ser Lys Asp Ala Trp Arg Leu
65                  70                  75                  80

Pro Gly Thr Tyr Val Val Leu Lys Glu Glu Thr Gln Arg Leu Gln
                85                  90                  95

Ser Glu Gln Thr Ala His Arg Leu Gln Thr Gln Ala Ala Arg Arg Gly
            100                 105                 110

Tyr Val Thr Lys Ile Leu His Val Phe His Asp Leu Leu Pro Gly Phe
        115                 120                 125

Leu Val Lys Met Ser Ser Asp Leu Leu Asp Leu Ala Leu Lys Leu Pro
130                 135                 140

His Val Asp Tyr Ile Glu Glu Asp Ser Ser Val Phe Ala Gln Ser Ile
145                 150                 155                 160

Pro Trp Asn Leu Glu Arg Ile Ile Pro Ala Arg His Gln Ala Asp Glu
                165                 170                 175

Tyr Ser Ser Xaa Xaa Xaa Xaa Pro Asp Gly Ser Ser Gln Val Glu Val
            180                 185                 190

Tyr Leu Leu Asp Thr Ser Ile Gln Ser Asp His Arg Glu Ile Glu Gly
        195                 200                 205

Arg Val Thr Val Thr Asp Phe Asn Ser Val Pro Glu Gly Asp Gly Thr
    210                 215                 220

Arg Phe His Arg Gln Ala Ser Lys Cys Asp Ser His Gly Thr His Leu
225                 230                 235                 240

Ala Gly Val Val Ser Gly Arg Asp Ala Gly Val Ala Lys Gly Thr Ser
                245                 250                 255
```

```
Leu Arg Ser Leu Arg Val Leu Asn Cys Gln Gly Lys Gly Thr Val Ser
            260                 265                 270

Gly Thr Leu Ile Gly Leu Glu Phe Ile Arg Lys Ser Gln Leu Ile Gln
        275                 280                 285

Pro Val Gly Pro Leu Val Leu Leu Pro Leu Ala Gly Gly Tyr Ser
    290                 295                 300

Arg Val Leu Asn Ala Ala Cys Gln Arg Leu Ala Arg Thr Gly Val Val
305                 310                 315                 320

Leu Val Ala Ala Ala Gly Asn Phe Arg Asp Asp Ala Cys Leu Tyr Ser
                325                 330                 335

Pro Ala Ser Ala Pro Glu Val Ile Thr Val Gly Ala Thr Asn Ala Gln
            340                 345                 350

Asp Gln Pro Val Thr Leu Gly Thr Leu Gly Thr Asn Phe Gly Arg Cys
        355                 360                 365

Val Asp Leu Phe Ala Pro Gly Lys Asp Ile Ile Gly Ala Ser Ser Asp
    370                 375                 380

Cys Ser Thr Cys Phe Met Ser Gln Ser Gly Thr Ser Gln Ala Ala Ala
385                 390                 395                 400

His Val Ala Gly Ile Val Ala Met Met Leu Ser Ala Glu Pro Glu Leu
                405                 410                 415

Thr Leu Ala Glu Leu Arg Gln Arg Leu Ile His Phe Ser Thr Lys Asp
            420                 425                 430

Val Ile Asn Met Ala Trp Phe Pro Glu Asp Gln Arg Val Leu Thr Pro
        435                 440                 445

Asn Leu Val Ala Thr Leu Pro Pro Ser Thr His Gly Thr Gly Gly Gln
450                 455                 460

Leu Leu Cys Arg Thr Val Trp Ser Ala His Ser Gly Pro Thr Arg Thr
465                 470                 475                 480

Ala Thr Ala Thr Ala Arg Cys Ala Pro Asp Glu Glu Leu Leu Ser Cys
                485                 490                 495

Ser Ser Phe Ser Arg Ser Gly Lys Arg Arg Gly Asp Arg Ile Glu Ala
            500                 505                 510

Ile Gly Gly Gln Gln Val Cys Lys Ala Leu Asn Ala Phe Gly Gly Glu
        515                 520                 525

Gly Val Tyr Ala Val Ala Arg Cys Cys Leu Leu Pro Arg Ala Asn Cys
    530                 535                 540

Ser Ile His Thr Thr Pro Ala Ala Arg Ala Ser Met Glu Thr Arg Val
545                 550                 555                 560

His Cys His Gln Lys Asp His Val Leu Thr Gly Cys Ser Ser His Trp
                565                 570                 575

Glu Val Glu Asp Leu Gly Xaa Xaa Lys Xaa Pro Val Leu Arg Ser Arg
            580                 585                 590

Gly Gln Pro Gly Gln Cys Val Gly His Arg Glu Ala Ser Val His Ala
        595                 600                 605

Ser Cys Cys His Ala Pro Gly Leu Glu Cys Lys Ile Lys Glu His Gly
    610                 615                 620

Ile Pro Gly Pro Ala Glu Gln Val Thr Val Ala Cys Glu Ala Gly Trp
625                 630                 635                 640

Thr Leu Thr Gly Cys Ser Val Leu Pro Gly Ala Ser Leu Val Leu Gly
                645                 650                 655

Ala Tyr Ala Val Asp Asn Thr Cys Val Val Arg Ser Arg Asp Val Ser
            660                 665                 670
```

```
Thr Ala Gly Arg Thr Ser Glu Glu Ala Thr Val Ala Ala Ala Ile Cys
        675                 680                 685

Cys Arg Ser Arg Pro Ser Ala Gln Ala Ser Trp Val Xaa Gln
    690                 695                 700

<210> SEQ ID NO 31
<211> LENGTH: 689
<212> TYPE: PRT
<213> ORGANISM: Homo sapiens

<400> SEQUENCE: 31

Met Gly Thr Val Ser Ser Arg Arg Ser Trp Trp Pro Leu Pro Leu Leu
  1               5                  10                  15

Leu Leu Leu Leu Leu Leu Gly Pro Ala Gly Ala Arg Ala Gln Glu
                 20                  25                  30

Asp Glu Asp Gly Asp Tyr Glu Glu Leu Val Leu Ala Leu Arg Ser Glu
                 35                  40                  45

Glu Asp Gly Leu Ala Glu Ala Pro Glu His Gly Thr Thr Ala Thr Phe
 50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
                100                 105                 110

His Val Phe His Leu Leu Pro Gly Phe Leu Val Lys Met Ser Gly Asp
                115                 120                 125

Leu Leu Glu Leu Ala Leu Lys Leu Pro His Val Asp Tyr Ile Glu Glu
                130                 135                 140

Asp Ser Ser Val Phe Ala Gln Ser Ile Pro Trp Asn Leu Glu Arg Ile
145                 150                 155                 160

Thr Pro Pro Arg Tyr Arg Ala Asp Glu Tyr Gln Pro Pro Asp Gly Gly
                165                 170                 175

Ser Leu Val Glu Val Tyr Leu Leu Asp Thr Ser Ile Gln Ser Asp His
                180                 185                 190

Arg Glu Ile Glu Gly Arg Val Met Val Thr Asp Phe Glu Asn Val Pro
                195                 200                 205

Glu Glu Asp Gly Thr Arg Phe His Arg Gln Ala Ser Lys Cys Asp Ser
                210                 215                 220

His Gly Thr His Leu Ala Gly Val Val Ser Gly Arg Asp Ala Gly Val
225                 230                 235                 240

Ala Lys Gly Ala Ser Met Arg Ser Leu Arg Val Leu Asn Cys Gln Gly
                245                 250                 255

Lys Gly Thr Val Ser Gly Thr Leu Ile Gly Leu Glu Phe Ile Arg Lys
                260                 265                 270

Ser Gln Leu Val Gln Pro Val Pro Leu Val Val Leu Pro Leu Ala
                275                 280                 285

Gly Gly Tyr Ser Arg Val Leu Asn Ala Ala Cys Gln Arg Leu Ala Arg
                290                 295                 300

Ala Gly Val Val Leu Val Thr Ala Ala Gly Asn Phe Arg Asp Asp Ala
305                 310                 315                 320

Cys Leu Tyr Ser Pro Ala Ser Ala Pro Glu Val Ile Thr Val Gly Ala
                325                 330                 335

Thr Asn Ala Gln Asp Gln Pro Val Thr Leu Gly Thr Leu Gly Thr Asn
                340                 345                 350
```

```
Phe Gly Arg Cys Val Asp Leu Phe Ala Pro Gly Glu Asp Ile Ile Gly
            355                 360                 365
Ala Ser Ser Asp Cys Ser Thr Cys Phe Val Ser Gln Ser Gly Thr Ser
370                 375                 380
Gln Ala Ala His Val Ala Gly Ile Ala Ala Met Met Leu Ser Ala
385                 390                 395                 400
Glu Pro Glu Leu Thr Leu Ala Glu Leu Arg Gln Leu Ile His Phe Ser
            405                 410                 415
Ala Lys Asp Val Ile Asn Glu Ala Trp Phe Pro Glu Asp Gln Arg Val
            420                 425                 430
Leu Thr Pro Asn Leu Val Ala Ala Leu Pro Pro Ser Thr His Gly Ala
            435                 440                 445
Gly Trp Gln Leu Phe Cys Arg Thr Val Trp Ser Ala His Ser Gly Pro
    450                 455                 460
Thr Arg Met Ala Thr Ala Ile Ala Arg Cys Ala Pro Asp Glu Glu Leu
465                 470                 475                 480
Leu Ser Cys Ser Ser Phe Ser Arg Ser Gly Lys Arg Arg Gly Glu Arg
            485                 490                 495
Met Glu Ala Gln Gly Gly Lys Leu Val Cys Arg Ala His Asn Ala Phe
                500                 505                 510
Gly Gly Glu Gly Val Tyr Ala Ile Ala Arg Cys Cys Leu Leu Pro Gln
            515                 520                 525
Ala Asn Cys Ser Val His Thr Ala Pro Pro Ala Glu Ala Ser Met Gly
            530                 535                 540
Thr Arg Val His Cys His Gln Gln Gly His Val Leu Thr Gly Cys Ser
545                 550                 555                 560
Ser His Trp Glu Val Glu Asp Leu Gly Thr His Lys Pro Pro Val Leu
                565                 570                 575
Arg Pro Arg Gly Gln Pro Asn Gln Cys Val Gly His Arg Glu Ala Ser
            580                 585                 590
Ile His Ala Ser Cys Cys His Ala Pro Gly Leu Glu Cys Lys Val Lys
        595                 600                 605
Glu His Gly Ile Pro Ala Pro Gln Glu Gln Val Thr Val Ala Cys Glu
    610                 615                 620
Glu Gly Trp Thr Leu Thr Gly Cys Ser Ala Leu Pro Gly Thr Ser His
625                 630                 635                 640
Val Leu Gly Ala Tyr Ala Val Asp Asn Thr Cys Val Val Arg Ser Arg
                645                 650                 655
Asp Val Ser Thr Thr Gly Ser Thr Ser Glu Glu Ala Val Thr Ala Val
            660                 665                 670
Ala Ile Cys Cys Arg Ser Arg His Leu Ala Gln Ala Ser Gln Glu Leu
        675                 680                 685
Gln
```

NEUTRALIZING PROPROTEIN CONVERTASE SUBTILISIN KEXIN TYPE 9 (PCSK9) VARIANTS AND USES THEREOF

RELATED APPLICATIONS

The present application claims priority to U.S. Provisional Application 61/125,304, filed Apr. 23, 2008, the entirety of which is hereby incorporated by reference.

FIELD OF THE INVENTION

The present invention relates to variants of proprotein convertase subtilisin kexin type 9 (and molecules related thereto) and methods of using the variants (and molecules related thereto) for treating various disorders.

BACKGROUND OF VARIOUS EMBODIMENTS

Proprotein convertase subtilisin kexin type 9 (PCSK9) is a serine protease involved in regulating the levels of the low density lipoprotein receptor (LDLR) protein (Horton et al., 2007; Seidah and Prat, 2007). In vitro experiments have shown that adding PCSK9 to HepG2 cells lowers the levels of cell surface LDLR (Benjannet et al., 2004; Lagace et al., 2006; Maxwell et al., 2005; Park et al., 2004). Experiments with mice have shown that increasing PCSK9 protein levels decreases levels of LDLR protein in the liver (Benjannet et al., 2004; Lagace et al., 2006; Maxwell et al., 2005; Park et al., 2004), while PCSK9 knockout mice have increased levels of LDLR in the liver (Rashid et al., 2005). Additionally, various human PCSK9 mutations that result in either increased or decreased levels of plasma LDL have been identified (Kotowski et al., 2006; Zhao et al., 2006). PCSK9 has been shown to directly interact with the LDLR protein, be endocytosed along with the LDLR, and co-immunofluoresce with the LDLR throughout the endosomal pathway (Lagace et al., 2006). Degradation of the LDLR by PCSK9 has not been observed and the mechanism through which it lowers extracellular LDLR protein levels is uncertain.

PCSK9 is a prohormone-proprotein convertase in the subtilisin (S8) family of serine proteases (Seidah et al., 2003). Humans have nine prohormone-proprotein convertases that can be divided between the S8A and S8B subfamilies (Rawlings et al., 2006). Furin, PC1/PC3, PC2, PACE4, PC4, PC5/PC6 and PC7/PC8/LPC/SPC7 are classified in subfamily S8B. Crystal and NMR structures of different domains from mouse furin and PC1 reveal subtilisin-like pro- and catalytic domains, and a P domain directly C-terminal to the catalytic domain (Henrich et al., 2003; Tangrea et al., 2002). Based on the amino acid sequence similarity within this subfamily, all seven members are predicted to have similar structures (Henrich et al., 2005). SKI-1/S1P and PCSK9 are classified in subfamily S8A. Sequence comparisons with these proteins also suggest the presence of subtilisin-like pro- and catalytic domains (Sakai et al., 1998; Seidah et al., 2003; Seidah et al., 1999). In these proteins the amino acid sequence C-terminal to the catalytic domain is more variable and does not suggest the presence of a P domain.

Prohormone-proprotein convertases are expressed as zymogens and they mature through a multi step process. The function of the pro-domain in this process is two-fold. The pro-domain first acts as a chaperone and is required for proper folding of the catalytic domain (Ikemura et al., 1987). Once the catalytic domain is folded, autocatalysis occurs between the pro-domain and catalytic domain. Following this initial cleavage reaction, the pro-domain remains bound to the catalytic domain where it then acts as an inhibitor of catalytic activity (Fu et al., 2000). When conditions are correct, maturation proceeds with a second autocatalytic event at a site within the pro-domain (Anderson et al., 1997). After this second cleavage event occurs the pro-domain and catalytic domain dissociate, giving rise to an active protease.

Autocatalysis of the PCSK9 zymogen occurs between Gln152 and Ser153 (VFAQ|SIP) (Naureckiene et al., 2003), and has been shown to be required for its secretion from cells (Seidah et al., 2003). A second autocatalytic event at a site within PCSK9's pro-domain has not been observed. Purified PCSK9 is made up of two species that can be separated by non-reducing SDS-PAGE; the pro-domain at 17 Kd, and the catalytic plus C-terminal domains at 65 Kd. PCSK9 has not been isolated without its inhibitory pro-domain, and measurements of PCSK9's catalytic activity have been variable (Naureckiene et al., 2003; Seidah et al., 2003).

SUMMARY OF VARIOUS EMBODIMENTS

In some embodiments, the invention comprises a PCSK9 variant and/or a use thereof.

In some embodiments, the PCSK9 variant can be a neutralizing PCSK9 variant that can include a Pro/Cat domain, or fragment thereof, that binds to low density lipoprotein receptor (LDLR) and an inactive V domain to LDLR activity. The inactive V domain does not result in the degradation of LDLR.

In some embodiments, the invention comprises a nucleic acid molecule that encodes for a PCSK9 variant (or neutralizing variant).

In some embodiments, the invention comprises a host cell that comprises a herein disclosed nucleic acid molecule that encodes for a PCSK9 variant.

In some embodiments, the invention comprises a vector that comprises a herein disclosed nucleic acid molecule that encodes for a PCSK9 variant.

In some embodiments, the invention comprises a pharmaceutical composition comprising at least one neutralizing PCSK9 variant (or a nucleic acid sequence encoding for a neutralizing PCSK9 variant) and a pharmaceutically acceptable carrier and/or excipient.

In some embodiments, the invention comprises a method of treating or preventing a condition associated with elevated serum cholesterol in a patient. In some embodiments, the method can comprise administering to a patient in need thereof an effective amount of at least one of the herein disclosed compounds (including, for example, a neutralizing PCSK9 variant and/or a nucleic acid sequence encoding a neutralizing PCSK9 variant).

In some embodiments, the invention comprises a method of inhibiting the binding of endogenous PCSK9 to LDLR in a patient. In some embodiments, the method comprises administering an effective amount of at least one of the herein disclosed compounds (including, for example, a neutralizing PCSK9 variant and/or a nucleic acid sequence encoding a neutralizing PCSK9 variant) to a subject in need thereof.

In some embodiments, the invention comprises a method of treating or preventing a condition associated with elevated serum cholesterol in a subject. In some embodiments, the method can comprise administering to a subject in need thereof an effective amount at least one of the herein disclosed compounds (including, for example, a neutralizing PCSK9 variant and/or a nucleic acid sequence encoding a neutralizing PCSK9 variant) simultaneously or sequentially with an agent that elevates the availability of low density lipoprotein receptor (LDLR) protein.

In some embodiments, the invention comprises a method of lowering serum cholesterol in a subject. In some embodiments, the method can comprise administering to a subject an effective amount of at least one of the herein disclosed compounds (including, for example, a neutralizing PCSK9 variant and/or a nucleic acid sequence encoding a neutralizing PCSK9 variant).

In some embodiments, the invention comprises a method of lowering serum cholesterol in a subject. In some embodiments, the method can comprise administering to a subject an effective amount of at least one of the herein disclosed compounds (including, for example, a neutralizing PCSK9 variant and/or a nucleic acid sequence encoding a neutralizing PCSK9 variant) simultaneously or sequentially with an agent that elevates the availability of low density lipoprotein receptor (LDLR) protein.

In some embodiments, the invention comprises the use of at least one of the herein disclosed compounds (including, for example, a neutralizing PCSK9 variant and/or a nucleic acid sequence encoding a neutralizing PCSK9 variant) in the manufacture of a medicament for the treatment of hypercholesterolemia.

In some embodiments, the invention comprises at least one of the herein disclosed compounds (including, for example, a neutralizing PCSK9 variant and/or a nucleic acid sequence encoding a neutralizing PCSK9 variant) for use as a medicament.

In some embodiments, the invention comprises at least one of the herein disclosed compounds (including, for example, a neutralizing PCSK9 variant and/or a nucleic acid sequence encoding a neutralizing PCSK9 variant) for use in treating hypercholesterolemia.

In some embodiments, the invention comprises a pharmaceutical composition comprising a Pro/Cat domain, or fragment thereof, that binds to low density lipoprotein receptor (LDLR), and an inactive V domain to LDLR activity. The inactive V domain does not result in the degradation of LDLR. The pharmaceutical composition further comprises a pharmaceutically acceptable carrier or diluent.

In some embodiments, the invention comprises a pharmaceutical composition comprising a Pro/Cat domain, or fragment thereof, that binds to low density lipoprotein receptor (LDLR) and an inactive V domain to LDLR activity. The inactive V domain does not result in the degradation of LDLR. The pro/cat domain is present in an amount sufficient for the treatment of a cholesterol related disorder.

BRIEF DESCRIPTION OF THE FIGURES

FIG. 1A depicts an amino acid sequence of the mature form of the PCSK9 with the pro-domain underlined.

FIGS. $1B_1$-$1B_4$ depict amino acid and nucleic acid sequences of PCSK9 with the pro-domain underlined and the signal sequence in bold.

FIG. 1C is a comparison on the sequences of PCSK9 from various organisms. (Any "O" in FIGS. 1C-1E are actually "Q")

FIG. 1D is a continuation of FIG. 1C.

FIG. 1E is a continuation of FIG. 1D.

FIG. 1F is an alignment of the Cat domain of the PCSK9 protein of SEQ ID NO: 3 with another Cat domain of another PCSK9 protein.

FIG. 1G is an alignment of the Cat domain of the PCSK9 protein of SEQ ID NO: 3 with another Cat domain of another PCSK9 protein.

FIG. 1H is an alignment of the Cat domain of the PCSK9 protein of SEQ ID NO: 3 with another Cat domain of another PCSK9 protein.

Figure 1I:
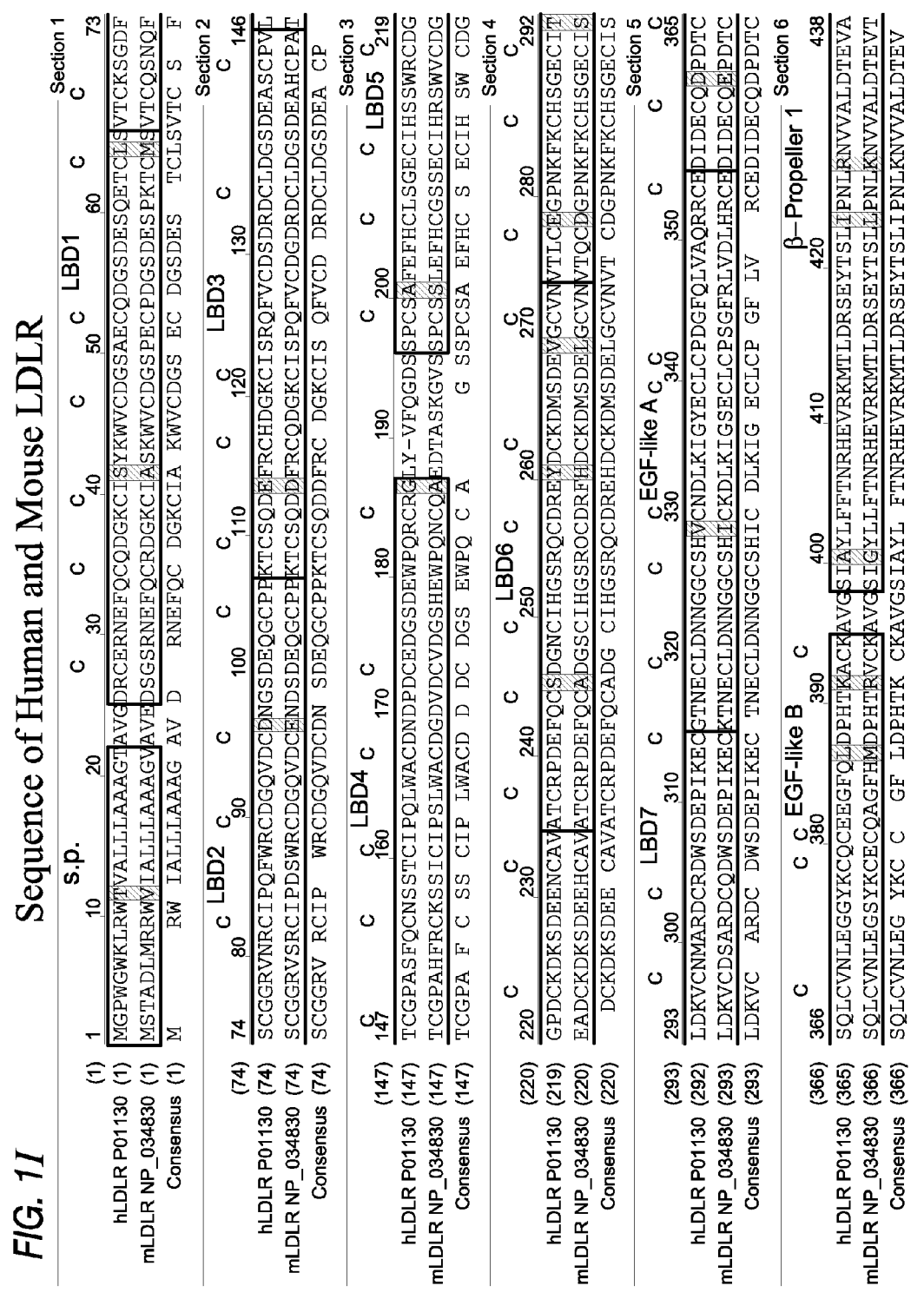

FIG. 1I is an alignment and consensus sequence for the amino acid sequence of LDLR.

FIG. 1J is a continuation of the alignment and consensus sequence for the amino acid sequence of LDLR presented in FIG. 1I.

FIG. 1K is an alignment and consensus sequence for the amino acid sequence of LDLR.

FIG. 1L is a continuation of the alignment and consensus sequence for the amino acid sequence of LDLR presented in FIG. 1K.

FIGS. $1M_1$ and $1M_2$ depict an embodiment of a PCSK9 protein.

FIGS. $1N_1$ and $1N_2$ depict an embodiment of a PCSK9 protein.

FIGS. $1O_1$ and $1O_2$ depict an embodiment of a PCSK9 protein.

FIGS. $1P_1$ and $1P_2$ depict an embodiment of a PCSK9 protein.

FIGS. $1Q_1$ and $1Q_2$ depict an embodiment of a PCSK9 protein.

FIGS. $1R_1$ and $1R_2$ depict an embodiment of a consensus sequence for a PCSK9 protein.

FIGS. $1S_1$ and $1S_2$ depict an embodiment of a human PCSK9 protein.

Figure 2:
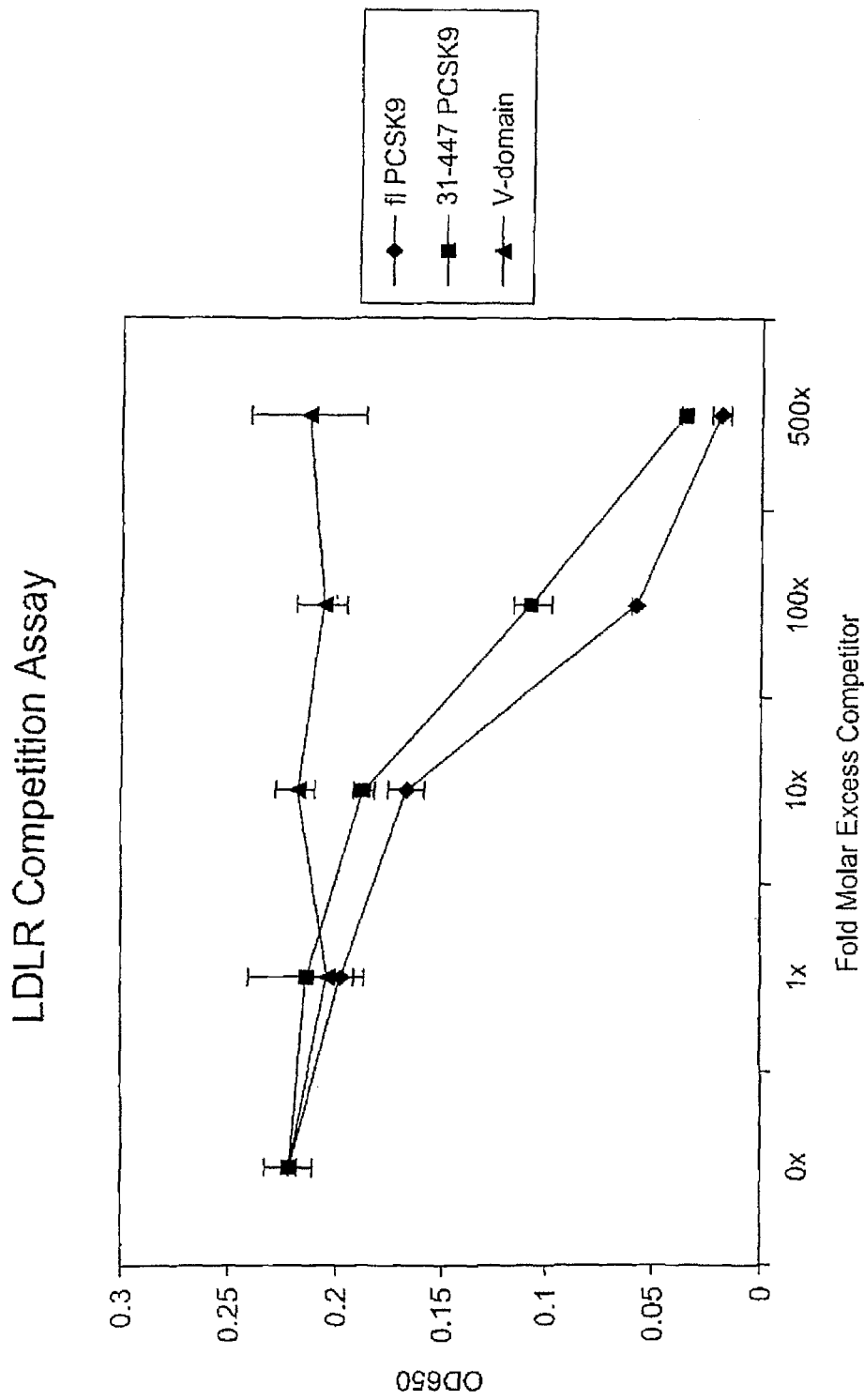

FIG. 2 is a graph depicting the results of a binding assay between LDLR and biotin-labeled full length PCSK9, competed with either a) unlabeled full length PCSK9, b) unlabeled residues 31-447 of PCSK9, or c) the unlabeled V domain of PCSK9 (residues 450-692).

Figure 3A:
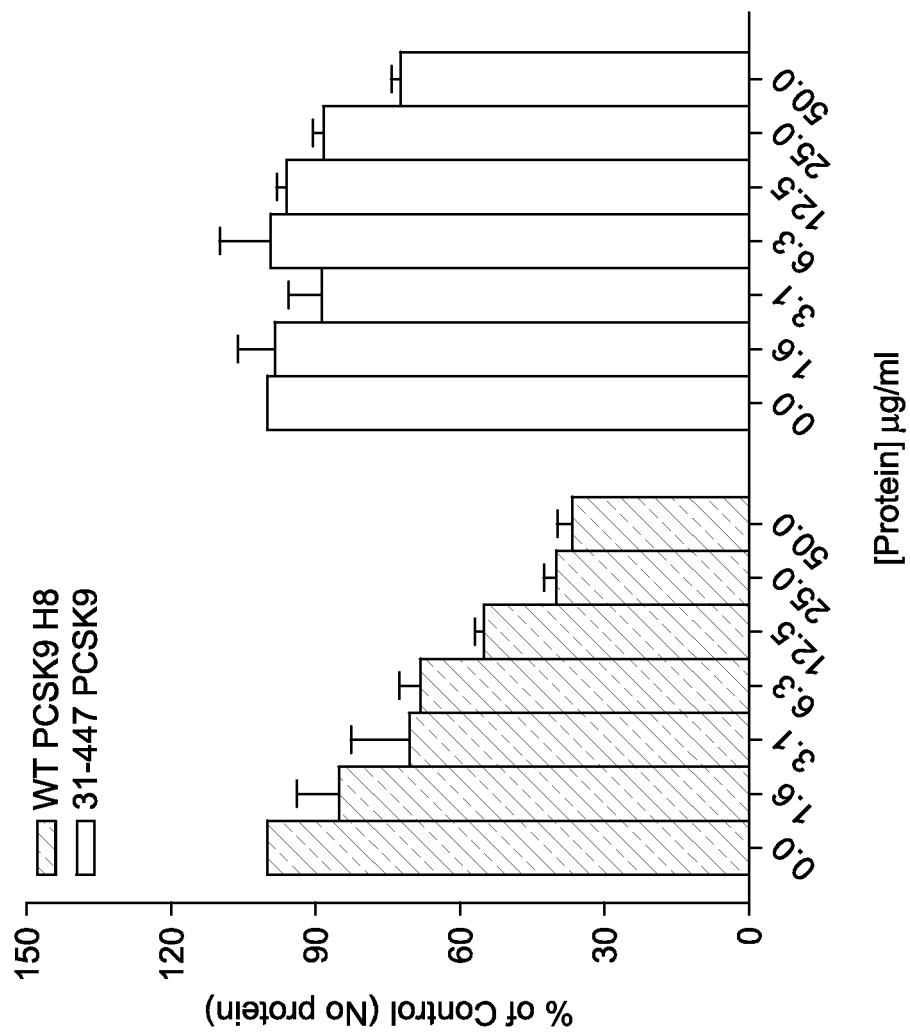

FIG. 3A is a graph depicting the results of the activity of residues 31-447 of PCSK9 on LDL uptake.

Figure 3B:
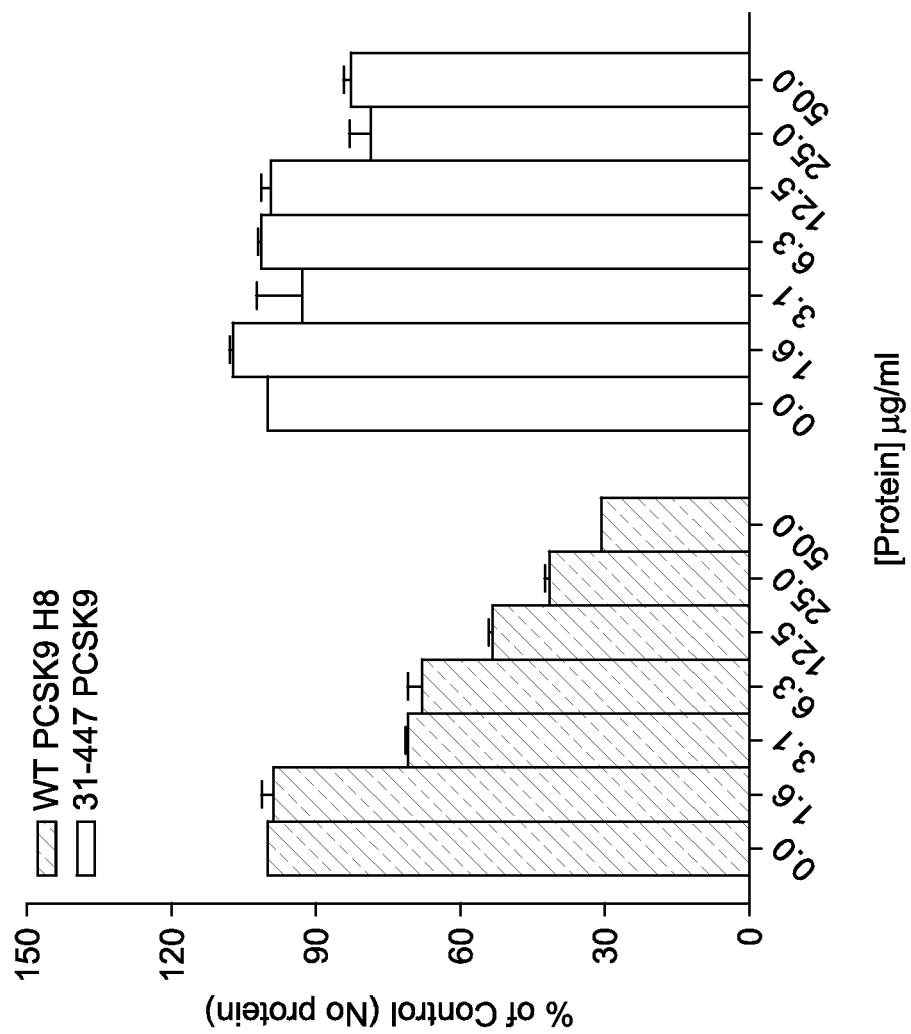

FIG. 3B is a graph depicting the results of the activity of residues 31-447 of PCSK9 on LDL uptake.

Figure 4:
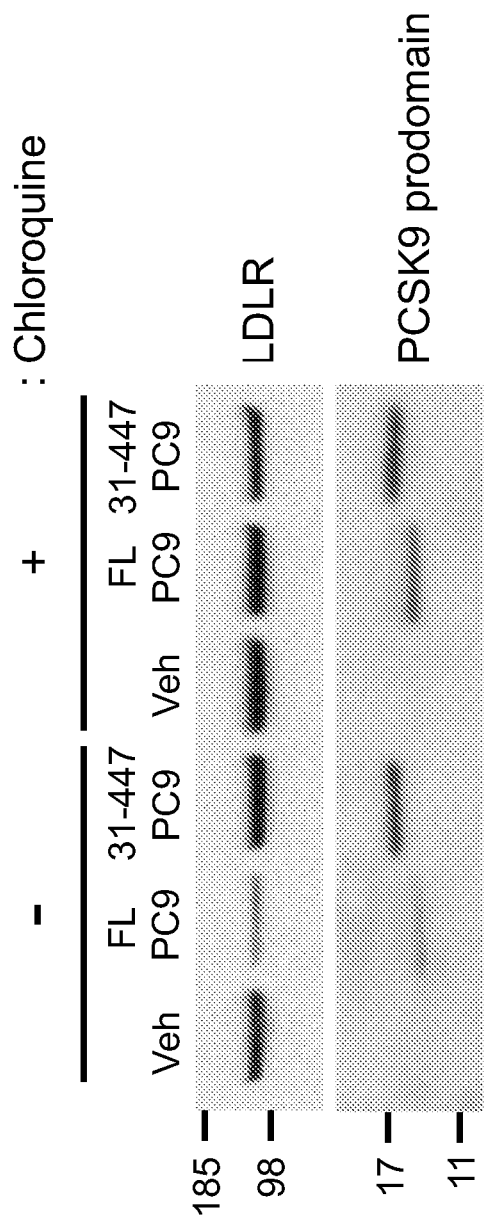

FIG. 4 is a depiction of a Western blot comparing the effect of full length PCSK9 vs. residues 31-447 of PCSK9 (a Pro/Cat fragment) on LDLR protein levels and PCSK9 uptake. As can be seen in the left-hand side of the gel, full length PCSK9 (FL PC9) results in a decrease in LDLR, while residues 31-447 of PCSK9 (a Pro/Cat fragment that functions as a neutralizing PCSK9 variant) does not result in a decrease in LDLR.

Figure 5:
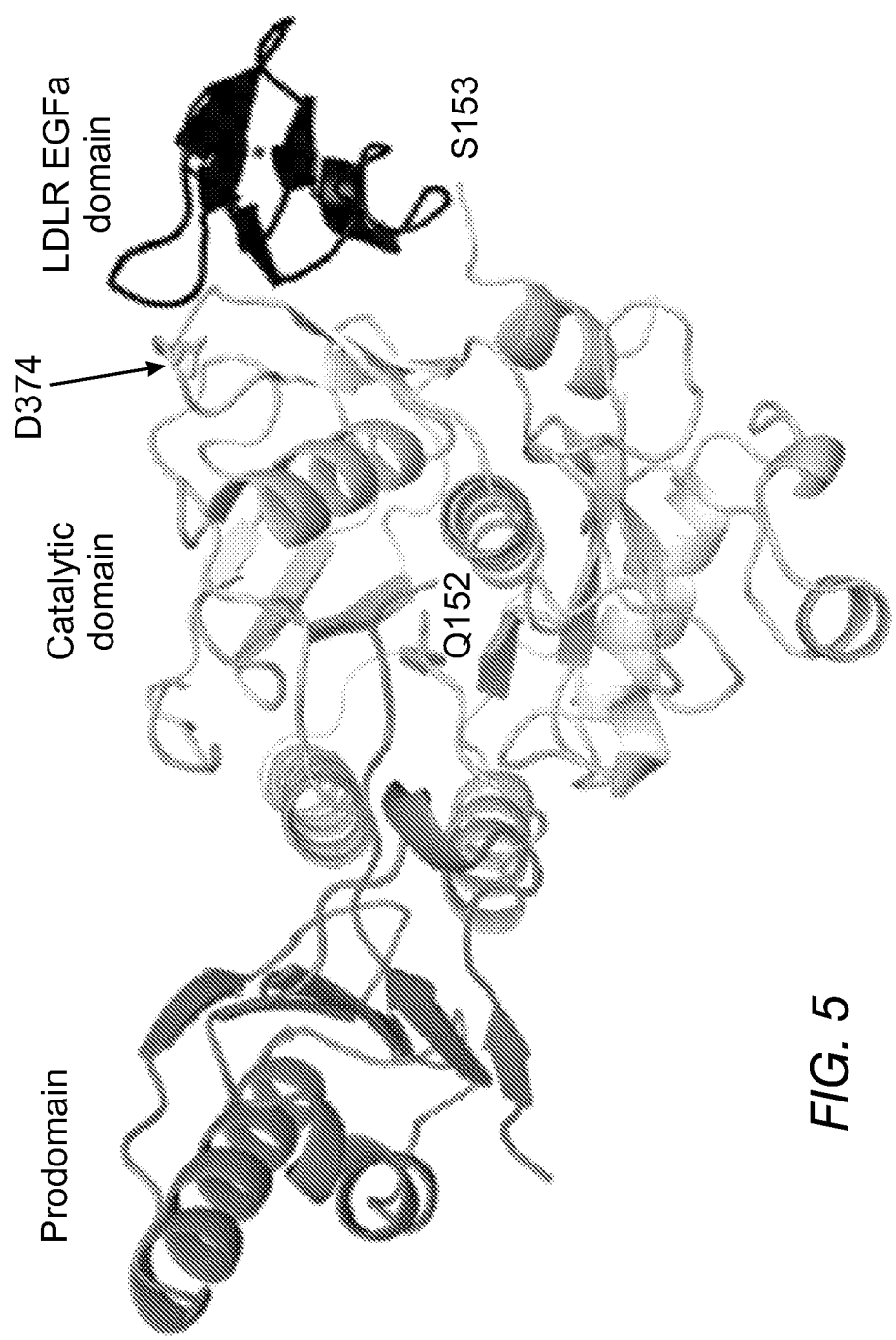

FIG. 5 is a depiction of the structure of PCSK9 and the EGFa section of LDLR.

Figure 6:
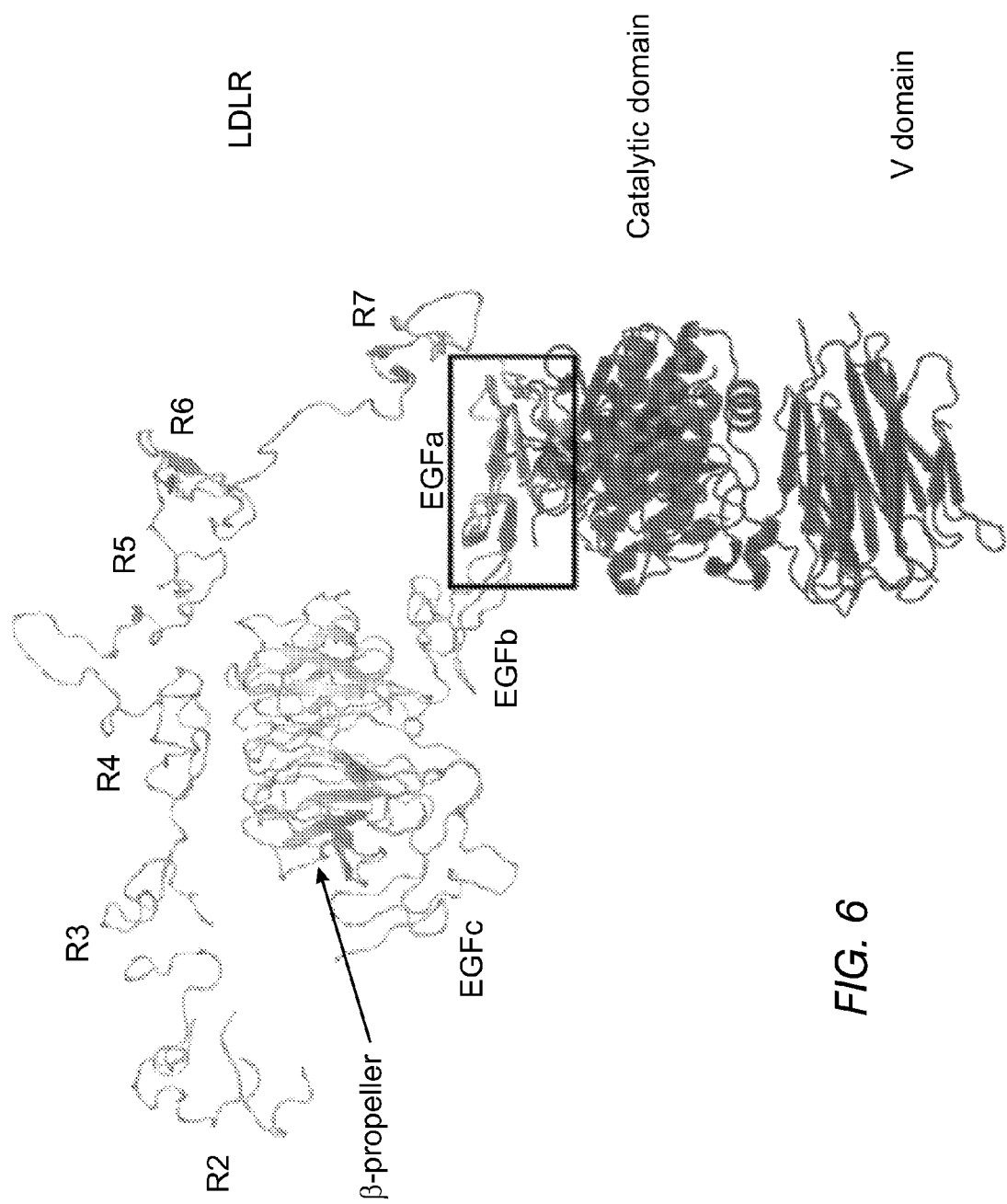

FIG. 6 is a depiction of a structural model of PCSK9 and LDLR.

Figure 7:
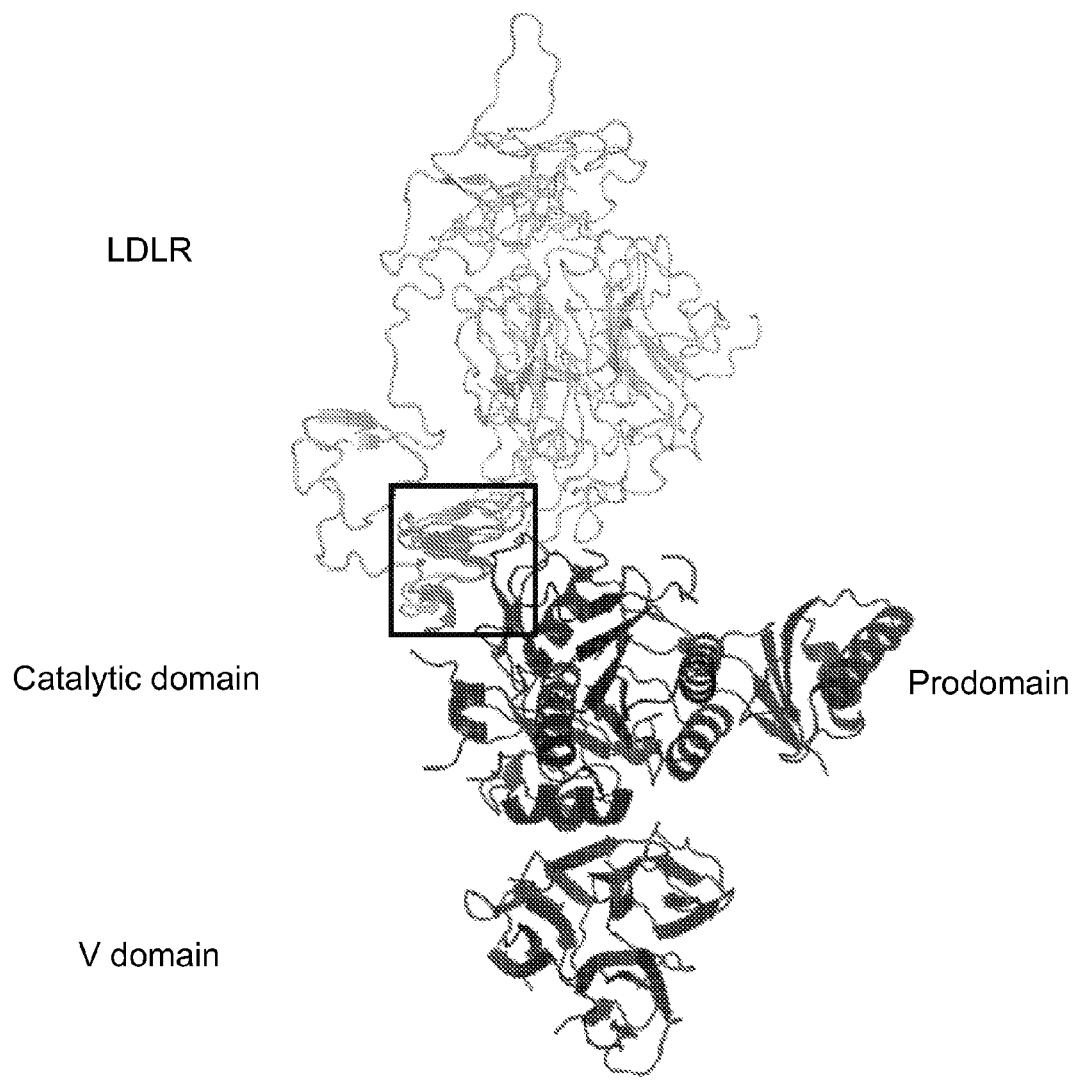

FIG. 7 is a depiction of the structural model of PCSK9 and LDLR from an alternative perspective.

Figure 8:
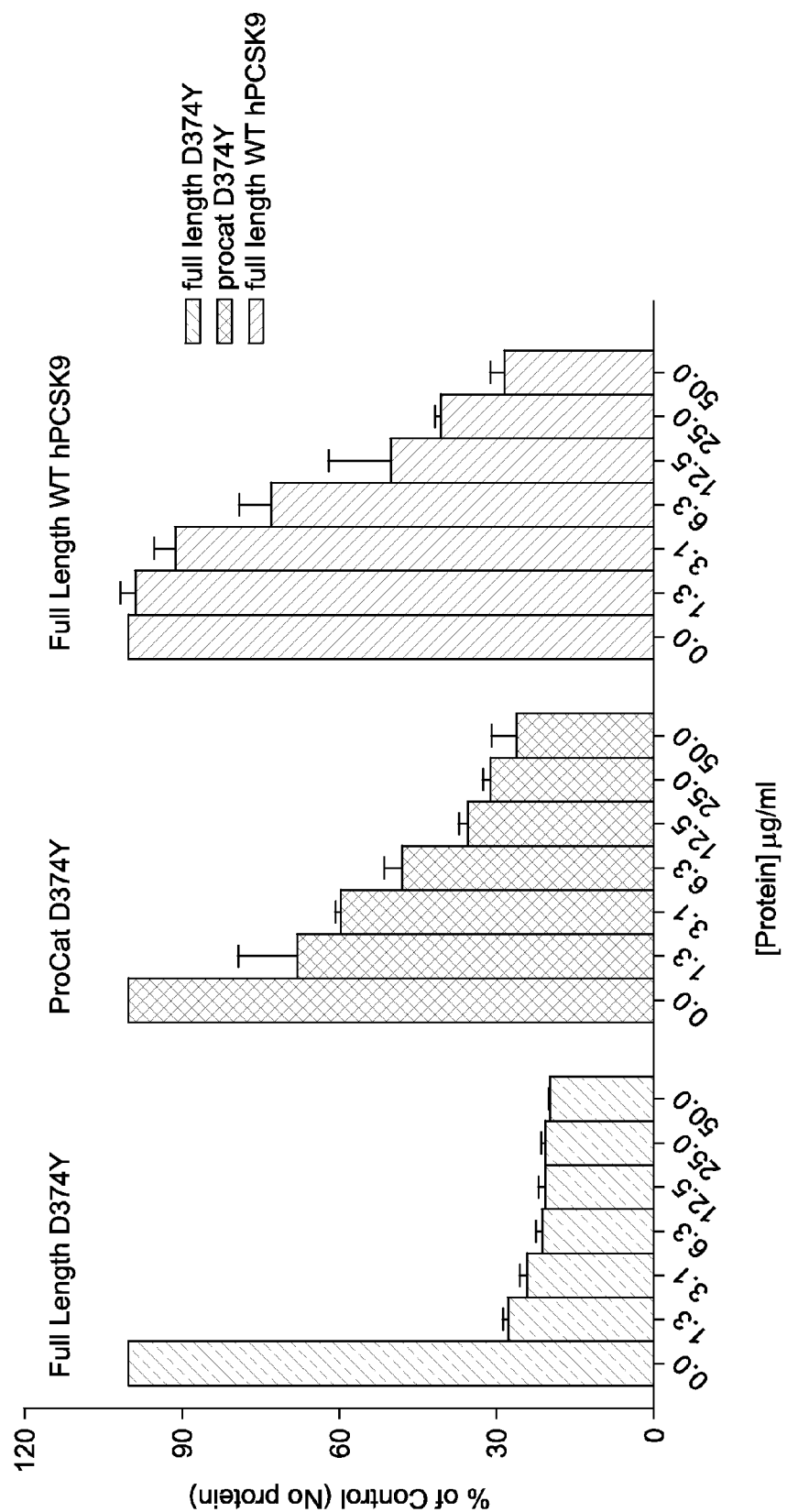

FIG. 8 is a graph depicting the results of the activity of the D374Y variant of residues 31-447 of PCSK9 (an example of another variant of the Pro/Cat domain) on LDL uptake.

Figure 9:
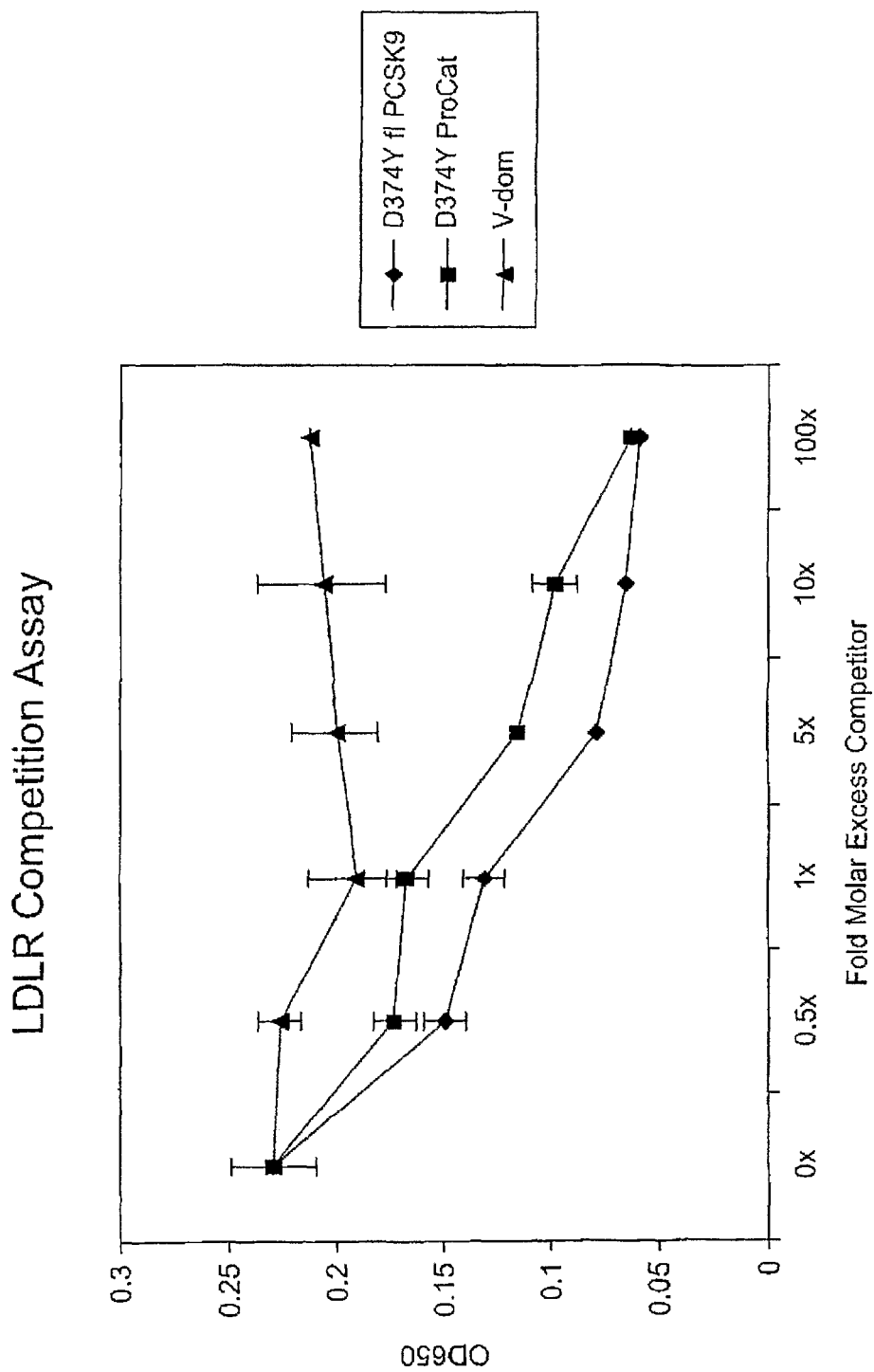

FIG. 9 is a graph depicting the results of a competition assay which included the D374Y variant of residues 31-447 of PCSK9.

DETAILED DESCRIPTION OF CERTAIN EXEMPLARY EMBODIMENTS

Proprotein convertase subtilisin kexin type 9 (PCSK9) is a serine protease involved in regulating the levels of the low density lipoprotein receptor (LDLR) protein. It is believed that native PCSK9 binds to LDLR in vivo and is involved in the degradation of LDLR. This can be problematic because the reduction in available LDLR results in less binding between LDLR and LDL, which in turn results in more LDL in the serum of the subject, resulting in an increase in serum cholesterol.

The full length PCSK9 protein includes a signal sequence (generally amino acids 1-30), a N-terminal prodomain ("Pro" domain, generally amino acids 31-152), a subtilisin-like catalytic domain ("Cat" domain, generally amino acids 153-446), a loop region (generally amino acids 447-453) and a C-terminal domain ("V" domain, generally amino acids 454-692).

Some embodiments of the invention relate to the discovery that the ability of PCSK9 (or variants thereof) to bind to LDLR can be separated from the ability of PCSK9 to effectively degrade or reduce the amount of available LDLR. It has been discovered that while parts of the Pro and/or Cat domains are involved in binding to PCSK9, the V domain is important for the effective degradation of LDLR. Furthermore, variants of PCSK9 that include an active part of the Pro and/or Cat domain can be used to block native PCSK9 from binding to LDLR. Thus, in some embodiments, the invention relates to a neutralizing PCSK9 variant that can block native PCSK9 from binding to LDLR, while the neutralizing PCSK9 variant itself will not effectively degrade LDLR. In some embodiments, the invention comprises a variant of PCSK9 that still includes an active Pro/Cat domain and that lacks a functional V domain (and thus lacks the ability to effectively lower LDLR in a subject). This variant can be used to prevent or reduce native PCSK9 from binding to LDLR. In turn, this can effectively elevate the level of LDLR in a subject and result in lower levels of LDL in the serum.

Some embodiments of the invention relate to the discovery that using a neutralizing PCSK9 variant (e.g., a variant that includes an active Pro/Cat domain and an inactive V domain) can result in the neutralizing PCSK9 variant competitively blocking and preventing native PCSK9 from binding to and degrading LDLR, while still allowing LDLR to perform its beneficial role of sequestering LDL. As such, neutralizing variants of PCSK9 can be used to lower serum LDL in a subject. Thus, in some embodiments, the invention comprises a neutralizing PCSK9 variant (or its use) that can bind to LDLR and prevent native PCSK9 from binding to LDLR, while still allowing LDLR to bind to and act on LDL.

Some embodiments of the invention relate to the discovery that using a neutralizing PCSK9 variant (e.g., a variant that includes an active Pro/Cat domain and an inactive V domain) can result in the neutralizing PCSK9 variant competitively blocking and preventing native PCSK9 from binding to and degrading LDLR, while still allowing LDLR to recycle (e.g., be endocytosed and then return back to the plasma membrane). Thus, in some embodiments, the invention comprises a neutralizing PCSK9 variant (or its use) that can bind to LDLR and prevent native PCSK9 from binding to LDLR, while still allowing LDLR to recycle.

In some embodiments, the neutralizing PCSK9 variant comprises, consists, or consists essentially of some or all of the Pro and/or Cat domains of PCSK9. In some embodiments, the neutralizing PCSK9 variant does not include some or all of the V domain. In some embodiments the neutralizing PCSK9 variant does not have a fully functional LDLR degrading V domain. In some embodiments the neutralizing PCSK9 variant has an inactive V domain. As will be appreciated by one of skill in the art, some of these embodiments can be beneficial in situations in which one wishes to lower the serum cholesterol in a subject, such as in hypercholesterolemia. Neutralizing PCSK9 variants can be used in various methods and compositions for treating subjects with elevated serum cholesterol levels, at risk of elevated serum cholesterol levels, or in those that could benefit from a reduction in their serum cholesterol levels. Thus, various methods and techniques for lowering, maintaining, or preventing an increase in serum cholesterol are also described herein.

Exemplary human PCSK9 amino acid sequences are presented as SEQ ID NOs: 1 and 3. An exemplary human PCSK9 coding sequence is presented as SEQ ID NO: 2, in FIG. 1A (depicting the "pro" domain of the protein as underlined) and FIG. 1B (depicting the signal sequence in bold and the pro domain underlined). Additional variants of PCSK9 (or the Cat domain of PCSK9) are shown in FIGS. 1C-1H. The structure of the PCSK9 protein has recently been solved by two groups (Cunningham et al., Nature Structural & Molecular Biology, 2007, and Piper et al., Structure, 15:1-8, 2007), the entireties of both of which are herein incorporated by reference.

For convenience, the following sections generally outline the various meanings of the terms used herein. Following this discussion, general aspects regarding neutralizing PCSK9 variants are discussed, followed by specific examples.

Definitions and Embodiments

It is to be understood that both the foregoing general description and the following detailed description are exemplary and explanatory only and are not restrictive of the invention as claimed. In this application, the use of the singular includes the plural unless specifically stated otherwise. In this disclosure, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

The term "proprotein convertase subtilisin kexin type 9" or "PCSK9" refers to a polypeptide as set forth in SEQ ID NO: 1 and/or 3 or fragments thereof, as well as related polypeptides, which include, but are not limited to, allelic variants, splice variants, derivative variants, substitution variants, and/or insertion variants including the addition of an N-terminal methionine, fusion polypeptides, and interspecies homologs. Examples of related proteins are put forth in FIGS. 1C-1H. In some embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to, the protein can be referred to as the "cleaved" or "processed" PCSK9. When only the inert form is being referred to, the protein can be referred to as the "inert", "pro-form", or "unprocessed" form of PCSK9. The term PCSK9 as used herein also includes naturally occurring alleles, such as the mutations D374Y, D374H, S127R, F216L, R46L, R237W, L253F, A443T, H553R, and others (Kotowski I K et al, A spectrum of PCSK9 alleles contributes to plasma levels of low-density lipoprotein cholesterol, Am J. Hum. Genet. 2006; 78:410-422). The term PCSK9 also encompasses PCSK9 molecules incorporating post-translational modifications of the PCSK9 amino acid sequence, such as PCSK9 sequences that have been glycosylated, PEGylated, PCSK9 sequences from which its signal sequence has been cleaved, PCSK9 sequence from which its pro domain has been cleaved from the catalytic domain but not separated from the catalytic domain (e.g., FIGS. 1A and 1B).

The term "PCSK9 activity" includes any biological effect of PCSK9. In some embodiments, PCSK9 activity includes the ability of PCSK9 to interact or bind to a substrate or receptor. In some embodiments, PCSK9 activity is represented by the ability of PCSK9 to bind to a LDL receptor (LDLR). In some embodiments, PCSK9 binds to and catalyzes a reaction involving LDLR. In some embodiments, PCSK9 activity includes the ability of PCSK9 to alter (e.g., reduce) the availability of LDLR. In some embodiments, PCSK9 activity includes the ability of PCSK9 to increase the amount of LDL in a subject. In some embodiments, PCSK9 activity includes the ability of PCSK9 to decrease the amount of LDLR that is available to bind to LDL. In some embodiments, "PCSK9 activity" includes any biological activity resulting from PCSK9 signaling. Exemplary activities include, but are not limited to, PCSK9 binding to LDLR, PCSK9 enzyme activity that cleaves LDLR or other proteins, PCSK9 binding to proteins other than LDLR that facilitate PCSK9 action, PCSK9 altering APOB secretion (Sun X-M et al, "Evidence for effect of mutant PCSK9 on apolipoprotein B secretion as the cause of unusually severe dominant hypercholesterolemia, Human Molecular Genetics 14: 1161-1169, 2005 and Ouguerram K et al, "Apolipoprotein B100 metabolism in autosomal-dominant hypercholesterolemia related to mutations in PCSK9, Arterioscler thromb Vasc Biol. 24: 1448-1453, 2004), PCSK9's role in liver regeneration and neuronal cell differentiation (Seidah N G et al, "The secretory proprotein convertase neural apoptosis-regulated convertase 1 (NARC-1): Liver regeneration and neuronal differentiation" PNAS 100: 928-933, 2003), and PCSK9s role in hepatic glucose metabolism (Costet et al., "Hepatic PCSK9 expression is regulated by nutritional status via insulin and sterol regulatory element-binding protein 1c" J. Biol. Chem. 281(10):6211-18, 2006). PCSK9 activity can be distinct from the terms "active Pro/Cat domain" or "inactive V domain" as defined herein.

The term "hypercholesterolemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced herein).

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass neutralizing PCSK9 variants, or sequences that have deletions from, additions to, and/or substitutions of one or more amino acid of the PCSK9 protein or variant. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In some embodiments, fragments are about five to 500 amino acids long. For example, fragments can be at least 5, 6, 7, 8, 9, 10, 10-14, 14-20, 20-50, 50-70, 70-100, 100-110, 110-150, 150-200, 200-250, 250-300, 300-350, 350-400, or 400-450 amino acids long.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

The term "amino acid" includes its normal meaning in the art and includes both naturally and non-naturally occurring amino acids.

A "variant" of a polypeptide (e.g., a neutralizing PCSK9 variant) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are typically aligned in a way that gives the largest match between the sequences. One example of a computer program that can be used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In some embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Examples of parameters that can be employed in determining percent identity for polypeptides or nucleotide sequences using the GAP program are the following:
  Algorithm: Needleman et al., 1970, *J. Mol. Biol.* 48:443-453
  Comparison matrix: BLOSUM 62 from Henikoff et al., 1992, supra
  Gap Penalty: 12 (but with no penalty for end gaps)
  Gap Length Penalty: 4
  Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, the twenty conventional (e.g., naturally occurring) amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:
  1) hydrophobic: norleucine, Met, Ala, Val, Leu, Ile;
  2) neutral hydrophilic: Cys, Ser, Thr, Asn, Gln;
  3) acidic: Asp, Glu;
  4) basic: His, Lys, Arg;
  5) residues that influence chain orientation: Gly, Pro; and
  6) aromatic: Trp, Tyr, Phe.

For example, non-conservative substitutions can involve the exchange of a member of one of these classes for a member from another class. Such substituted residues can be introduced, for example, into regions of a PCSK9 protein that are homologous with non-human PCSK9 proteins, or into the non-homologous regions of the molecule.

In making changes to the PCSK9 protein or variant thereof, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in some embodiments, the substitution of amino acids whose hydropathic indices are within ±2 is included. In some embodiments, those which are within ±1 are included, and in some embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In some embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in some embodiments, the substitution of amino acids whose hydrophilicity values are within ±2 is included, in some embodiments, those which are within ±1 are included, and in some embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In some embodiments, derivatives comprise covalent modifications, including, but not limited to, chemical bonding with polymers, lipids, or other organic or inorganic moieties. In some embodiments, a chemically modified neutralizing PCSK9 variant can have a greater circulating half-life than a neutralizing PCSK9 variant that is not chemically modified. In some embodiments, a chemically modified neutralizing PCSK9 variant can have improved targeting capacity for desired cells, tissues, and/or organs. In some embodiments, a derivative neutralizing PCSK9 variant is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In some embodiments, a derivative neutralizing PCSK9 variant comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In some embodiments, a derivative is covalently modified with polyethylene glycol (PEG) subunits. In some embodiments, one or more water-soluble polymer is bonded at one or more specific position, for example at the amino terminus, of a derivative. In some embodiments, one or more water-soluble polymer is randomly attached to one or more side chains of a derivative. In some embodiments, PEG is used to improve the therapeutic capacity for a neutralizing PCSK9 variant. In some embodiments, PEG is used to improve the therapeutic capacity of a molecule. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) can be used in some embodiments to generate more stable peptides. In addition, constrained peptides comprising a consensus sequence or a substantially identical consensus sequence variation can be generated by methods known in the art (Rizo and Gierasch, Ann. Rev. Biochem., 61:387 (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

A "recombinant neutralizing PCSK9 variant" is a protein made using recombinant techniques, i.e., through the expression of a recombinant nucleic acid as described herein. Methods and techniques for the production of recombinant proteins are well known in the art.

The term "neutralizing PCSK9 variant" refers to a PCSK9 variant that associates and/or binds to LDLR competitively with a full length human PCSK9. The neutralizing PCSK9 variant also has a reduced ability to degrade or remove LDLR from a system compared to wild-type PCSK9 (e.g., SEQ ID NO: 3). In some embodiments, the neutralizing PCSK9 variant lacks a fully functional LDLR degrading V domain (e.g., the PCSK9 protein has an inactive V domain). In some embodiments, the neutralizing PCSK9 variant has a reduced ability to degrade or take LDLR out of a system compared to a similar variant lacking a fully functional V domain. Stated another way, a neutralizing PCSK9 variant has the ability to directly or indirectly reduce the degradation of LDLR and thus maintain or increase LDLR levels in a system.

The term "pro" or "pro domain" is used to refer to at least a part of the prodomain of PCSK9. In some embodiments, the prodomain of PCSK9 is involved (either directly or indirectly (such as by allowing proper folding of the Cat domain)) in the binding of PCSK9 to LDLR. While the exact starting and ending residue of the pro domain can vary based on the specific embodiment, the pro domain will at least comprise residues 61-152 of SEQ ID NO: 3 and variants thereof. In some embodiments, the pro domain comprises amino acids 31-152 of SEQ ID NO: 3, or variants thereof. Variants of the Pro domain can be 50% or more (e.g., 50-60, 60-70, 70-80, 80-90, 90-95, 95-98, 98-99, or 99-100 percent identical to the corresponding Pro domain of SEQ ID NO: 3 and/or a consensus sequence (e.g., shown in FIG. 1C-1E).

The term "Cat" or "cat domain" is used to refer to at least a part of the catalytic domain of PCSK9. In some embodiments, the "cat domain" is involved in the binding of PCSK9 to LDLR. While the exact starting and ending residue of the Cat domain can vary based on the specific embodiment, the Cat domain will at least comprise residues 153-381 and in some embodiments will comprise at least residues 153-445 of SEQ ID NO: 3 and variants thereof. Variants of the Cat domain can be 50% or more (e.g., 50-60, 60-70, 70-80, 80-90, 90-95, 95-98, 98-99, or 99-100 percent) identical to the corresponding Cat domain of SEQ ID NO: 3. In some embodiments, the cat domain can starts at residue 153 of SEQ ID NO: 3 (and variants thereof) and ends at any one of residues 447, 448, 449, 450, 451, 452, or 453 of SEQ ID NO: 3 (and variants thereof). Thus, the Cat domain can include residues 153-447, 153-448, 153-449, 153-450, 153-451, 153-452, 153-453, or 153-454 of SEQ ID NO: 3 (and variants thereof) and/or a consensus sequences (e.g., shown in FIGS. 1C-1H and FIGS. 1R$_1$-1R$_2$, SEQ ID NOs: 9, 11, 13, 15, and 30 where FIGS. 1F-1H display examples of a Cat domain).

The term "Pro/Cat" or "Pro/Cat domain" is used to refer to the section of PCSK9 that is involved in binding to LDLR. The "Pro/Cat domain" need not include both the Pro and Cat domain. In particular, something referred to as the "Pro/Cat domain" can comprise the Pro domain without the Cat domain, or the Cat domain without the Pro domain. While the term also encompasses a PCSK9 protein that includes both the Pro and the Cat domain, when both of these domains are required to be present the phrase "Pro domain and Cat domain" or similar phrase is generally employed. In some embodiments, the pro/cat domain can start at residues 31 or 61 of SEQ ID NO: 3 (and variants thereof) and end at any one of residues 447, 448, 449, 450, 451, 452, or 453 of SEQ ID NO: 3 (and variants thereof). Thus, in some embodiments, the Pro/Cat domain can include residues 31-447, 31-448, 31-449, 31-450, 31-451, 31-452, 31-453, 61-447, 61-448, 61-449, 61-450, 61-451, 61-452, and 61-453 of SEQ ID NO: 3 (and variants thereof), and/or SEQ ID NOs: 4, 5, 6, 7, 8, 24-29 and/or 31 and/or a consensus sequence (e.g., shown in FIGS. 1C-1E and 1R$_1$-1R$_2$ SEQ ID NOs: 9 and 30 (and F—H for the Cat domain, SEQ ID Nos: 11, 13, and 15)). Of course, the "pro/cat" domain can also simply include the pro or cat regions noted above. In some embodiments, variants of the pro/cat domain can be 50% or more (e.g., 50-60, 60-70, 70-80, 80-90, 90-95, 95-98, 98-99, or 99-100 percent) identical to the corresponding pro/cat domain of SEQ ID NO: 3. In some embodiments, the pro/cat domain is at least 50, 55, 60, 65, 70, 75, 80, 85, 90, 95, 96, 97, 98, 99, or more percent identical for the conserved sections of the pro/cat domain. In some embodiments, while the sections of the pro/cat domain that are 100% conserved (shown in FIGS. 1C-1E) are conserved in the pro/cat variant, the remaining positions can be changed. In some embodiments, the changes in these remaining positions can result in a pro/cat variant that is 50-60, 60-70, 70-80, 80-90, 90-95, 95-98, 98-99, or 99-100 percent identical to the corresponding pro/cat domain of SEQ ID NO: 3. In some embodiments, the variable positions are those shown as spaces or gaps in the consensus sequence in FIGS. 1C-1E and FIG. 1R$_1$-1R$_2$ or non specific amino acids in FIGS. 1F-1H (and/or shown as "Xaa" in SEQ ID NOs: 9, 11, 13, 15, and 30).

As will be appreciated by one of skill in the art, the sequence alignment shown in the attached FIGS. 1C-1H and 1I-1L) denote the residues that, in some embodiments (including various neutralizing PCSK9 variants), can be conserved in order to obtain a functional Pro, Cat, Pro/Cat, or LDLR domain or protein and those that can be changed (and how they can be changed). In some embodiments, the sections denoted by spaces in the consensus sequences are amino acid(s) where conservation is not required and any or no amino acid can be used at these locations (e.g., variation is readily allowable at these locations). In some embodiments, the sections denoted by "+" can similarly be altered with any amino acid. In some embodiments, the sections denoted by "+" are conservative replacements, or the replacements noted for that position in the sequence listing (or in the various organisms for the sequence alignment). As noted herein, various consensus sequences are disclosed within FIGS. 1C-1L. Thus, consensus sequences in addition to the consensus sequence explicitly identified in the figures are also disclosed herein.

The term "V" or "V domain" is used to refer the section of the PCSK9 protein that is involved in the effective degradation of LDLR. While the exact starting and ending residues of the V domain can vary based on the specific embodiment, the V domain will at least comprise residues 455-682 of SEQ ID NO: 3 and variants thereof. In some embodiment the V domain will at least comprise residues 457-679, 454-692, 457-692, 457-682, 455-692, 455-679, 454-682, or 454-679. Variants of the V domain can be 55% or more (e.g., 55-60, 60-70, 70-80, 80-90, 90-95, 95-98, 98-99, or 99-100 percent identical to the corresponding V domain of SEQ ID NO: 3. Simply because there is an amino acid sequence on the c-terminal end of a pro/cat domain does not make that sequence a V domain or an active V domain. An active V domain will also have the above noted function in regard to LDLR. As will be appreciated by one of skill in the art, inactive V domains encompass a broader scope of possible domains, sequences, and structures than do active V domains. Any protein, or a lack of PCSK9 protein, that does not achieve the V domain's function noted above can be characterized as an inactive V domain.

The term "loop" is used to refer to the section between the V domain and the Cat domain. This section need not be called out explicitly in every embodiment. While the exact starting and ending residues of the loop can vary based on the specific embodiment, the loop can comprise residues 447-453 of SEQ ID NO: 3 and variants thereof. Variants of the loop can be 0% or more (e.g., 0-10, 10-20, 20-30, 30-40, 40-50 50-60, 60-70, 70-80, 80-90, 90-95, 95-98, 98-99, 99 percent identical to the loop of SEQ ID NO: 3. In some embodiments, any structure or section connecting the V domain to the Cat domain can be considered as a loop section. In some embodiments, the loop domain is not explicitly denoted as such and is simply part of either the Cat domain or the V domain.

The phrase "LDLR degrading" refers to the ability of the V domain (or subpart thereof), when part of a whole PCSK9 protein, to promote the degradation of LDLR. As will be appreciated by one of skill in the art in light of the present disclosure, the LDLR degrading ability of the V domain need not be a direct role. In particular, it can be possible for LDLR to be degraded by PCSK9 variants that lack the V domain. Thus, the LDLR "degrading role" or "ability" of the V domain denotes that this section of the PCSK9 protein is involved in the effective degradation of LDLR. The removal of the V domain need not completely prevent all LDLR degradation under all possible variables and circumstances (and, as noted below in the examples, in some circumstances, does not).

The phrase "fully functional LDLR degrading" or "fully functional LDLR degradation" refers to the amount of LDLR degradation that occurs from a PCSK9 protein that has the wild-type V domain following amino acid 450 of SEQ ID NO: 3. Thus, a "fully functional LDLR degrading V domain" will degrade LDLR at a rate equal to and/or greater than wild type PCSK9 (for example, SEQ ID NO: 3). Proteins that are not fully functional for LDLR degradation, that have an inactive V domain, or that lack a fully functional LDLR degrading V domain will degrade LDLR less effectively than the wild type PCSK9. Thus, for example, a variant of PCSK9 that is only 90% as effective as wild-type PCSK9 can be characterized as lacking a fully functional LDLR degrading V domain or as having an inactive V domain. A PCSK9 variant that lacks a V domain can also be described as lacking a fully functional LDLR degrading V domain or as having an inactive V domain. A PCSK9 protein that lacks a fully functional LDLR degrading V domain, that has an inactive V domain, or that lacks a V domain is less than 100% as effective as the wild type PCSK9 (SEQ ID NO: 3), include, for example, PCSK9 proteins that are 99-90, 90-80, 80-70, 70-60, 60-50, 50-40, 40-30, 30-20, 20-10, 10-5, 5-1, 1-0.1, 0.1-0.01, 0.01-0.001, 0.001-0.0001, and 0.0001 to 0% as effective as the wild type PCSK9 protein. As will be appreciated by one of skill in the art, a neutralizing PCSK9 variant can contain some or all of the V domain, as long as the V domain is not fully functional for LDLR degradation. The functionality of the V domain can be adjusted by various approaches, including, for example, removal, point mutations, insertions, deletions, etc.

The phrase term "active" as used in "active Pro domain," "active Pro/Cat domain," or "active Cat domain" denotes that the protein can bind to LDLR.

The term "inactive" as used in "inactive V domain" denotes that the molecule in question does not have a PCSK9 V domain that functions in LDLR degradation as effectively as the V domain in wild-type PCSK9. An inactive V domain does not require that the sequence of the V domain be present. In some embodiments, a neutralizing PCSK9 variant will have an inactive V domain if it lacks a V domain protein sequence.

The phrase "has an inactive V domain" denotes that the section of the V domain, if any section is present, is not as effective at degrading LDLR as the V domain in the full length PCSK9 protein. This does not require that any part of the V domain actually be present. Thus, a PCSK9 protein that lacks the entire V domain can also be characterized as "having an inactive V domain." As above, the definition does not require that the protein with the inactive V domain exhibit a complete absence of LDLR degrading ability. A PCSK9 protein that has an inactive V domain will be less than 100% as effective as the wild type PCSK9 (SEQ ID NO: 3). Examples of such lower levels of effectiveness include, for example, PCSK9 proteins having V domains that are 99-90, 90-80, 80-70, 70-60, 60-50, 50-40, 40-30, 30-20, 20-10, 10-5, 5-1, 1-0.1, 0.1-0.01, 0.01-0.001, 0.001-0.0001, and 0.0001 to 0% as effective as the wild type PCSK9 protein. Nonlimiting examples of inactive or inactivated V domains include, for example, proteins that lack V domains (e.g., the entire V domain is absent from the PCSK9 protein), proteins that lack 14 or more amino acids from the end (c-terminal) of the PCSK9 protein (e.g., SEQ ID NO: 3), proteins in which the V domain is improperly folded (in comparison to wild-type PCSK9; e.g., the C679X mutation).

The phrase "lacks the entirety of amino acids ###-###" denotes that the entire and exact amino acid sequence defined therein is absent from the protein. Subparts of the amino acid sequence or range can be present. For example, if the protein "lacks the entirety of amino acids 10-100 of SEQ ID NO: X," then amino acids 10-99 or 11-100 of SEQ ID NO: X can be present, although 10-100 are excluded from being present.

The phrase "attached adjacent to an amino acid ### of SEQ ID NO: X" denotes that whatever is (or is not) to be attached is (or is not) attached immediately adjacent to a specific amino acid (###). When the phrase is being used in a negative context (for example as an exclusion), then it denotes that, if amino acid ### is present, then the item in question is not attached adjacent to it. However, the use of this phrase does not imply or require that amino acid ### is actually present when used in its negative context. As an example, the phrase "lacks the entirety of amino acids 10-100 of SEQ ID NO: X attached adjacent to an amino acid 9 of SEQ ID NO: X" denotes that all 91 amino acids of amino acids 10-100 of SEQ ID NO: X are missing from the position adjacent to amino acid 9 of SEQ ID NO: X (if amino acid 9 is present). Thus, amino acids 11-100 can be present and attached adjacent to amino acid 9, amino acids 10-99 can be present and attached adjacent to amino acid 9, or amino acids 10-100 can be present and attached to either amino acid 8 or 11 of SEQ ID NO: 3. It is noted that, for the above type of exclusion, amino acid 9 does not need to be present. Thus, amino acids 1-5 of SEQ ID NO: X would also meet the above description, (as there is no amino acid 9 and there can be no amino acid adjacent to it). In addition, unless explicitly noted, the position "adjacent to" a specific amino acid is only the position that is greater than the noted amino acid. Thus, if the relevant amino acid is 9, then the only position adjacent to 9 is 10 (and thus position 8 is not considered "adjacent" to position 9 for the purposes of this definition). In other words, adjacent to only applies to the amino acid in the carboxy direction, not in the amino direction.

The phrase "at the appropriate position" as used in the phrase "at the appropriate position in the variant," denotes that, the appropriate position is present in the variant. For example, the phrase, "the neutralizing PCSK9 variant has a cysteine at position 30" denotes that the variant has an amino acid at position 30 and that it is a cysteine. When the phrase is used in reference to another SEQ ID NO:, it denotes that the variant is (or is not) similar to that other SEQ ID NO: in the manner described. When the phrase is used as an exclusion, then, as noted in the above definition, the position itself need not be present in the variant, but if it is, then it will not be the item described.

The term "target" refers to a molecule or a portion of a molecule capable of being bound by a neutralizing PCSK9 variant.

The terms "compete" or "competitive," when used in reference to "neutralizing PCSK9 variant" refers to the competition between a) native PCSK9 and b) PCSK9 variants for LDLR. Numerous types of competitive binding assays can be used to determine if one neutralizing PCSK9 variant competes with native PCSK9, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82).

As used herein, "substantially pure" means that the described species of molecule is the predominant species present, that is, on a molar basis it is more abundant than any other individual species in the same mixture. In some embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "agent" is used herein to denote a chemical compound, a mixture of chemical compounds, a biological macromolecule, or an extract made from biological materials.

As used herein, the terms "label" or "labeled" refers to incorporation of a detectable marker. Examples include incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In some embodiments, the label or marker can also be therapeutic. Various methods of labeling polypeptides and glycoproteins are known in the art and can be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The term "therapeutically effective amount" refers to the amount of a neutralizing PCSK9 variant determined to produce a therapeutic response in a mammal. Such therapeutically effective amounts are readily ascertained by one of ordinary skill in the art.

The term "modulator," as used herein, is a substance that changes or alters the activity or function of a molecule. For example, a modulator can cause an increase or decrease in the magnitude of a certain activity or function of a molecule compared to the magnitude of the activity or function observed in the absence of the modulator. In some embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human-animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms and/or underlying risk factors.

The term "prevent" does not require the 100% elimination of the possibility of an event. Rather, it denotes that the likelihood of the occurrence of the event has been reduced in the presence of the compound or method.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and can be any of the immunoglobulins, although IgG1 and IgG2 are preferred, Native Fc's are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that can be removed because they provide structural features or biological activity that are not required for the fusion molecules of PCSK9. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7)

antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means. In some embodiments, an Fc domain can be associated to a neutralizing PCSK9 variant (e.g., via a covalent bond between the Fc domain and the neutralizing PCSK9 variant).

The term "multimer" as applied to Fc domains or molecules comprising Fc domains refers to molecules having two or more polypeptide chains associated covalently, non-covalently, or by both covalent and non-covalent interactions. IgG molecules typically form dimers; IgM, pentamers; IgD, dimers; and IgA, monomers, dimers, trimers, or tetramers. Multimers can be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Neutralizing PCSK9 Variants

In some embodiments, the neutralizing PCSK9 variant provided herein is capable of inhibiting native PCSK9 from binding to LDLR. In some embodiments, this blocking results in a decrease in the degradation of LDLR in vivo; thereby resulting in a lowering of serum LDL in a subject.

As noted above, the ability of PCSK9 to bind to LDLR and the ability of wild-type PCSK9 to effectively degrade LDLR appear to be due to two different sections of the PCSK9 protein. As noted in the examples below, the ability of PCSK9 to effectively degrade LDLR appears to be linked to the V domain of PCSK9. Thus, in some embodiments, variants of PCSK9 that lack fully functional LDLR degrading V domains (or have an inactive V domain) can be introduced into a system or subject without adversely increasing the amount of LDLR degradation. Moreover, as described herein, the binding of PCSK9 to LDLR is mediated by sections of the Pro and/or Cat domains of PCSK9. Thus, neutralizing PCSK9 variants that contain sufficient sections of the Pro and/or Cat domain(s) can still bind to LDLR and compete with native PCSK9 for binding to LDLR. In some embodiments, when the variant also lacks a fully functional LDLR degrading V domain (or have an inactive V domain), then the PCSK9 variant will not only block native PCSK9, but will do so while lowering LDLR degradation, thereby increasing LDLR availability and in turn decreasing the amount of LDL in the serum. Thus, in some embodiments, a neutralizing PCSK9 variant is a PCSK9 protein that has an active Pro/Cat domain and an inactive V domain.

In some embodiments, the neutralizing PCSK9 variant includes, consists, or consists essentially of the Pro and/or Cat domain(s) of PCSK9. In some embodiments, the variant includes a signal sequence (for example, amino acids 1-30 of SEQ ID NO: 3). In some embodiments, the neutralizing PCSK9 variant comprises, consists, or consists essentially of amino acids 31-447 of SEQ ID NO: 3 (or a variant of amino acids 31-447). In some embodiments, the neutralizing PCSK9 variant comprises, consists, or consists essentially of amino acids 153-374 of SEQ ID NO: 3 (or a variant of amino acids 153-374). In some embodiments, the neutralizing PCSK9 variant comprises, consists, or consists essentially of amino acids 31-374 of SEQ ID NO: 3 (or a variant of amino acids 31-374). In some embodiments, the neutralizing PCSK9 variant comprises, consists, or consists essentially of amino acids 153-454 of SEQ ID NO: 3 (or a variant of amino acids 153-454). In some embodiments, the neutralizing PCSK9 variant comprises, consists, or consists essentially of amino acids 31-449 of SEQ ID NO: 3 (or a variant of amino acids 31-449). In some embodiments, the neutralizing PCSK9 variant comprises, consists, or consists essentially of amino acids 153-381 of SEQ ID NO: 3 (or a variant of amino acids 153-381). In some embodiments, the neutralizing PCSK9 variant comprises, consists, or consists essentially of amino acids 31-381 of SEQ ID NO: 3 (or a variant of amino acids 31-381). In some embodiments, the neutralizing PCSK9 variant comprises, consists, or consists essentially of amino acids 153-382 of SEQ ID NO: 3 (or a variant of amino acids 153-382). In some embodiments, the neutralizing PCSK9 variant comprises, consists, or consists essentially of amino acids 31-382 of SEQ ID NO: 3 (or a variant of amino acids 31-382). In some embodiments, the neutralizing PCSK9 variant comprises, consists, or consists essentially of an amino acid starting at either position 31, 61, or 153 of SEQ ID NO: 3 and ending at position 374, 381, 382, 447, 448, 449, 450, 451, 452, 453, 454, or 455 of SEQ ID NO: 3 (or a variant thereof). In some embodiments, variants can be at least 50 percent identical, for example 50-60, 60-70, 70-80, 80-90, 90-95, 95-98, 98-99 or greater identity, to the relevant section (e.g., any of the above noted sections) of SEQ ID NO: 3. In some embodiments, variants can have at least 70% homology, for example 50-60, 60-70, 70-80, 80-90, 90-95, 95-98, 98-99 or greater homology, to the relevant section of SEQ ID NO: 3.

In some embodiments, the V domain can be entirely removed. In some embodiments, a section of the V domain can be removed or altered. The section can be sufficient to prevent the neutralizing PCSK9 variant from significantly degrading LDLR In some embodiments, the variant lacks some or all of the V domain. In some embodiments, the V domain will be inactive and will not allow for wild-type levels of degradation of LDLR. In some embodiments, the neutralizing PCSK9 variant lacks the V domain completely. In some embodiments, the variant lacks residues 447-692, 448-692, 449-692, 450-692, 451-692, 452-692, 453-692, or 454-692 of SEQ ID NO: 3. In some embodiments, any of the above missing sections, can be present in the variant, but will not be placed immediately adjacent to the amino acid positioned in front of it in SEQ ID NO: 3. Thus, for example, 453-692, 454-692, 450-692, or 447-692 of SEQ ID NO: 3 can be present in the variant, but will not be positioned following amino acid 452, 453, 449, or 446 respectively of SEQ ID NO: 3. In some embodiments, at least the last 14 amino acids from the C-terminus of SEQ ID NO: 3 are missing (or different from the amino acids in SEQ ID NO: 3), thereby creating an inactive V domain. For example, 14-16, 16-20, 20-25, 25-30, 30-40, 40-50, 50-60, 60-70, 70-80, 80-90, 90-100, 100-120, 120-140, 140-160, 160-200, 200-220, 220-225 amino acids can be deleted from the C terminal portion of the V domain to produce an inactive V domain.

In some embodiments, the neutralizing PCSK9 variant includes a point mutation. In some embodiments, the point mutation is the D374Y point mutation that has an increased binding affinity to LDLR. In some embodiments, one or more other point mutations are also included in the neutralizing PCSK9 variant. For example, mutations such as I474V, R273W, H87N, A103D, G308R, S376G, D480G, R499c, D374X, where X can be Y, A, H, R, E, F, K, L, Y142X, C679X, R46L, L253F, A443T, A53V, H553R, Q619P, E670G and those disclosed in Kotowski I K et al, Am. J. Hum. Genet. 2006; 78:410-422, (incorporated herein by reference).

In some embodiments, any of the above variations (including mutations) and lengths of the V domain can be included or excluded from any of the above variations (including mutations) in the above noted pro and/or cat domains in order to produce a neutralizing PCSK9 variant. Thus, for example, the neutralizing variant can lack residues 453-692, 454-692, 450-692, or 447-692 of SEQ ID NO: 3 (or a variant thereof) positioned next to positions 452, 453, 449, or 446 respectively of SEQ ID NO: 3, while having any one of the above pro and/or cat regions (for example, 331-454, 31-447, 31-449, 153-374, 153-454, and 31-374 of SEQ ID NO: 3 (or a variant thereof)). In addition, any of the herein disclosed neutralizing PCSK9 variants can include a valine at 474 (instead of an isoleucine), a glycine at 670 (instead of a glutamate), and/or a glutamate at 620 (instead of a glycine). In some embodiments, the wild-type PCSK9 protein is that sequence defined in Genbank sequence NM_174936. Other SNP variants can be found in Kotowski I K et al, Am. J. Hum. Genet. 2006; 78:410-422 and include R46L, A53V, L253F, R237W, A443T, I474V, Q619P, E670G, and others.

In some embodiments, variants of neutralizing PCSK9 proteins are selected by comparing various PCSK9 sequences to one another in order to determine those positions that are conserved and those positions that vary between PCSK9 sequences. In some embodiments, amino acids in the pro and/or cat domains that are conserved between various organisms are conserved while amino acids that are not conserved across two or more species are allowed to vary. Such variants can still have pro and/or cat domain(s) that still compete with native PCSK9 for binding. An example of a sequence alignment between PCSK9 proteins of various organisms can be found in FIGS. 1C to 1E. As will be appreciated by one of skill in the art, the space(s) in the consensus sequence can be filled with any of the other amino acids in the comparison at the corresponding location, or, in some embodiments, any amino acid. FIGS. 1F-1H depict another series of alignments of just the cat domain (the top sequence in the figures are from SEQ ID NO: 3, where amino acid 1-153 (of SEQ ID NO: 3) and amino acid 321-454 (of SEQ ID NO: 3)). As will be appreciated by one of skill in the art, the space(s) in the consensus sequences can be filled with any of the other amino acids in the comparison at the corresponding location, or, in some embodiments, any amino acid. Given the similarity between the sequences in FIG. 1C-1H and SEQ ID NO: 3, the present invention contemplates that any of the above pro and/or cat domains can function as desired in a neutralizing PCSK9 variant (including variants that contain any one of the identified consensus sequences). As such, in some embodiments, any position that varies between the different PCSK9 sequences can be a position that can be altered in a neutralizing PCSK9 variant. In some embodiments, the position is altered to the other amino acid noted in the alignment. In some embodiments, the position is altered to a different amino acid. It is noted that the human PCSK9 sequence in FIGS. 1C-1E, while similar to SEQ ID NO: 3, includes an extra series of amino acids on the end of the sequence, including a glycine, followed by a proline, followed by 8 histidines. While the glycine or proline can be present or can be absent in various embodiments, the histidines are just part of a histidine tag, and are not a necessary part of the alignment or any of the proteins in the alignment. Thus, the consensus sequence need not have any of the histidines in it (all 8 can be removed in some embodiments as these are not structural elements of the protein). In some embodiments, the rat sequence in FIGS. 1C-1E has a glycine, followed by a proline, followed by 8 histidines on its end, just like the other sequences shown in FIG. 1E. Additional embodiments of PCSK9 sequences can be found in FIGS. $1M_1$-$1S_2$, SEQ ID Nos: 25-31.

As noted above, the consensus sequences shown in the attached FIGS. 1C-1H) indicate the residues that, in some embodiments, can be conserved in order to obtain a functional Pro/Cat domain and those that can be changed (and how they can be changed). In some embodiments, the sections of the consensus sequence denoted by spaces are amino acid(s) where conservation is not required and any or no amino acid can be used at these locations (e.g., variation is readily allowable at these locations). In some embodiments, the sections denoted by "+" can similarly be altered with any amino acid. In some embodiments, the sections denoted by "+" are conservative replacements, or the replacements noted for that position in the sequence listing (or in the various organisms for the sequence alignment).

In FIGS. 1C-1E, as more than two amino acid sequences have been aligned, the consensus sequence does not display spaces at each amino acid position that can be varied without the Pro/Cat domain losing its functionality. Thus, in this alignment, for some embodiments, even amino acids designated as a specific amino acid in the explicitly noted consensus sequence can be varied and still result in a functioning Pro/Cat domain. For example, in some embodiments, an amino acid position that is assigned a specific amino acid in the consensus sequence (in FIGS. 1C-1E), but varies between the various organisms, can be altered. Thus, in some embodiments, amino acid positions that are conserved between organisms (for example, as shown in FIGS. 1C-1E), are conserved in the neutralizing PCSK9 variant, but the other amino acid positions (those that are different between the various organisms) can be replaced with amino acids that are different from the amino acid denoted in their particular position of the consensus sequence. In some embodiments, the amino acid that replaces the amino acid in the consensus sequence is any amino acid (or none) and need not be limited to those amino acids appearing in the different sequences shown in FIGS. 1C-1E. In some embodiments, the amino acid change is to an amino acid that is the same as at least one of the amino acids shown in that position in the various amino acid sequences shown. In some embodiments, if the amino acids aligned for one position are different, but are conserved, then the amino acid position in the consensus sequence can be any amino acid having conserved properties (e.g., polar). In some embodiments, while amino acids that are identical between one or more of the species are present in the neutralizing PCK9 variant, one or more of the other amino acids at the other position(s) are varied. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, or more amino acids that are not identical between the various organisms in FIGS. 1C-1E can be replaced by any other amino acid. In some embodiments, while the amino acids that are identical across all of the species noted in the figures are kept the same, the amino acids at the other positions are allowed to vary, with as much as 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of these amino acids being altered to another amino acid. In some embodiments, the conserved amino acids noted in the figures can be altered or replaced by another amino acid(s).

In some embodiments, in creating a neutralizing PCSK9 variant, amino acids in the V domain that are conserved between various PCSK9 proteins of various organisms are altered while amino acids that are not conserved across one or more species are conserved, thereby producing a protein where the V domain is not active (or is inactive). An example of this comparison, between PCSK9 from various animals, can be found in FIGS. 1C to 1E. Thus, in some embodiments, any of the conserved amino acids in the V domain of PCSK9 can be altered while the conserved amino acids in the pro and/or cat domains can be maintained in order to produce a neutralizing PCSK9 variant. In some embodiments, the amino acid is altered to the other amino acid noted in the alignment. In some embodiments, the amino acid is altered to a different amino acid.

In some embodiments, residues that are important in the binding of PCSK9 to LDLR are maintained in the pro and/or cat domain(s). For example, those residues identified herein as part of the binding surface between LDLR and LDL or LDLR and PCSK9, or involved in the creation of the binding surface, as well as those residues discussed in "Molecular basis for LDL recognition by PCSK9" (PNAS, 105:1820-1825, 2008), such as Arg 194 and Phe 379 are maintained, if present within the fragment sequence. In some embodiments, the neutralizing PCSK9 variant includes at least residues 194-379.

In some embodiments, a neutralizing PCSK9 variant can inhibit, interfere with or modulate one or more biological activities of PCSK9. In one embodiment, the neutralizing PCSK9 variant competes with native PCSK9 for binding to LDLR. In some embodiments, the neutralizing PCSK9 variant reduces binding of native PCSK9 to LDLR by at least 1%, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent reduction of native PCSK9 binding to LDLR.

In some embodiments, the neutralizing PCSK9 variant has an $IC_{50}$ for blocking the binding of native PCSK9 to LDLR of less than 1 microMolar, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM. This $IC_{50}$ can be measured between native PCSK9 to LDLR and the neutralizing PCSK9 variant to LDLR.

In some embodiments, a neutralizing PCSK9 variant does not include a C679X and/or a Q554E point mutation. In some embodiments, the neutralizing PCSK9 variant does not include a His tag. In some embodiments, the neutralizing PCSK9 variant does not include a GST tag. In some embodiments, the neutralizing PCSK9 variant includes residue 453 of SEQ ID NO: 3, at the corresponding position in the variant. In some embodiments, the PCSK9 variant does not have the entirety of residues 453-692 removed from the protein. For example, in some embodiments, the neutralizing PCSK9 variant includes residues 31-453. In some embodiments, the neutralizing PCSK9 variant lacks residues such as 447, 448, 449, 450, 451, and 452 (or some combination thereof) of SEQ ID NO: 3. In some embodiments, the neutralizing PCSK9 variant lacks any amino acid at these positions. In some embodiments, the neutralizing PCSK9 variant lacks the corresponding amino acid at the specific position identified above in regard to SEQ ID NO: 3. In some embodiments, when explicitly stated, the neutralizing PCSK9 variants can exclude the PCSK9 variants disclosed in U.S. application Ser. No. 12/197,093, filed Aug. 22, 2008, hereby incorporated by reference in its entirety and especially in regard to its disclosure regarding antigen binding proteins and PCSK9 proteins and variants thereof. For example, when explicitly stated, the neutralizing PCSK9 variants can exclude a PCSK9 proteins/variants such as PCSK9 ProCat 31-449 and/or PCSK9 ProCat 31-454, with or without a his tag. In some embodiments, when explicitly stated, the neutralizing PCSK9 variants can exclude the PCSK9 variants that consist of residues 1-452 (having a His tag or a GST tag, (sequence numbering as defined in Fan et al., *American Chemical Society*, "Self-Association of Human PCSK9 Correlates with its LDLR-Degrading Activity"); residues 1-454, and 1-681 219-692 (sequence numbering as defined in Benjannet et al., *Journal of Biological Chemistry*, "NARC-1/PCSK9 and Its Natural Mutants," 279:48865-48875, 2004); residues 219-692 (sequence numbering as defined in Benhannet et al., *J. of Biol. Chemistry*, "The Proprotein Convertase (PC) PCSK9 is Inactivated by Furin and/or PC5/6A," 281 (41):30561-30572 (2006); residues 1-452 and 423-692 (sequence numbering as defined in Fan et al., *Biochemistry*, "Self-Assoication of Human PCSK9 Correlates with its LDLR-Degrading Activity," 47:1631-1639 2008); residues 1-455, 1-454, and/or residues 31-454 (sequence numbering as defined by Nassoury et al., *Traffic*, "The Cellular Trafficking of Secretory Proprotein Convertase PCSK9 and its Dependence on the LDLR," 8:718-732, 2007); any C terminal deletions in WO 2007/128121; residues 1-454 (sequence numbering as defined by Zhang et al., *PNAS*, "Structural Requirements for PCSK9-mediated degradation of the low-density lipoprotein Receptor," 105:13045-13050, 2008); residues 1-425, 1-453, 1-694, 31-453, and 1-507 (sequence numbering as defined by Naureckiene S. et al, *Archives of Biochemistry and Biophysics*, "Functional Characterization of Narc1, a Novel Proteinase Related to Proteinase K", 420:55-67, 2003); residues 31-451 and/or residues 53-451 (including variants of either of these, such as the following: P155G, W156L, N157K, L158A, I161A, R194A, D238A, D374Y, S386A, with or without a his tag) (sequence numbering as defined in Bottomley et al., *J. of Biological Chemistry*, "Structural and Biochemical Characterization of the Wild Type PCSK9/EGF-AB Complex and Natural FH mutants," 284:1313-23, 2008); an in-frame deletion of the eighth exon of 58 amino acids, e.g., deletion of residues 395-452 (keeping 1-394 and 453 to the end, as described in Schmidt et al., *DNA and Cell Biology*, "A Novel Splicing Variant of Proprotein Convertase Subtilisin/Kexin Type 9, 27:183-189, 2008); and/or residues 1-692 (human), 1-691 (rat), 1-316 (rat), 1-390 (rat), 1-390 (S385A, rat), 1-425 (rat), 1-453 (rat), 1-507 (rat), 31-691 (rat), 148-691 (rat), 1-691 (rat, including optional deletion of 31-147, optional deletion of 148-425, optional deletion of 219-395, histidine 225 to tryptophan, serine 385 to alanine, or histidine 225 to tryptophan and serine 385 to alanine), 1-142, and/or 1-679 (sequence numbering as defined in Bingham et al., *Cytometry A.*, "Proapoptotic effects of NARC 1 PCSK9), the gene encoding a novel serine proteinase," 69(11):1123-31, 2006). The entirety of the disclosure of each of the above noted references is incorporated herein by reference, especially in regard to their disclosures of the various PCSK9 sequences and discussion thereof. In some embodiments, any one or more of the abovevariants are encompassed within the group of useful neutralizing PCSK9 variants. In some embodiments, any or all of the above can be combined with or in a pharmaceutically acceptable carrier or be used for the preparation of a medicament.

In some embodiments, the neutralizing PCSK9 variant has a pro/cat domain that is different from the pro/cat domain in the cDNA sequence of NM-174936 or gi31317306. In some embodiments, the neutralizing PCSK9 variant includes point mutations at least one of the following positions: 474, 620, or 670. In some embodiments, the point mutation is Val474Iso, Gly670Glu, and/or Glu620Gly.

Vehicles

The term "vehicle" refers to a molecule that prevents degradation and/or increases half-life, reduces toxicity, reduces immunogenicity, or increases biological activity of a therapeutic protein when covatlently or non-covalently bound to the therapeutic protein. Exemplary vehicles include an Fc domain (including, for example, native Fcs, Fc variants, Fc domains, multimers, and dimers) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide; or any natural or synthetic protein, polypeptide or peptide that binds to a salvage receptor. Vehicles are further described in U.S. Pat. No. 6,660,843, herein incorporated by reference in its entirety. In some embodiments, multiple vehicles are used, for example, Fc's at each terminus or an Fc at a terminus and a PEG group at the other terminus or a sidechain. In some embodiments, the neutralizing PCSK9 variant is combined, associated, mixed, or bonded to any one or more of the above vehicles.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles can also be used. Various means for attaching chemical moieties useful as vehicles are currently available, see e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

In some embodiments, the polymer vehicle is polyethylene glycol (PEG). The PEG group can be of any convenient molecular weight and can be linear or branched. The average molecular weight of the PEG will preferably range from about 2 kiloDalton ("kD") to about 100 kDa and more preferably from about 5 kDa to about 50 kDa. The PEG groups will generally be attached to the neutralizing PCSK9 variant via acylation or reductive alkylation through a reactive group on the PEG moiety (e.g., an aldehyde, amino, thiol, or ester group) to a reactive group on the inventive compound (e.g., an aldehyde, amino, or ester group).

In some embodiments, a useful strategy for the PEGylation of synthetic peptides involves combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which can be used for protein modification. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water soluble polymer for use as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD can be used.

In another embodiment a vehicle is a non-Fc peptide or polypeptide known or believed to prevent degradation and/or increases half-life, reduces toxicity, reduces immunogenicity, or increases biological activity of a therapeutic protein. Example of such a protein vehicle include transthyretin or HSA protein fusions. These vehicles can be fused to a PCSK9 variant.

Linkers

Any "linker" group is optional. When present, its chemical structure is not critical, since it serves primarily as a spacer. The linker can be made up of amino acids linked together by peptide bonds. Thus, in some embodiments, the linker is made up of from 1 to 20 amino acids linked by peptide bonds, wherein the amino acids are selected from the 20 naturally occurring amino acids. Some of these amino acids can be glycosylated, as is well understood by those in the art. In some embodiments, the 1 to 20 amino acids are selected from glycine, alanine, proline, asparagine, glutamine, and lysine. In some embodiments, a linker is made up of a majority of amino acids that are sterically unhindered, such as glycine and alanine. In some embodiments, linkers are polyglycines (particularly $(Gly)_4$, $(Gly)_5$), poly(Gly-Ala), and polyalanines. Other specific examples of linkers are: $(Gly)_3$ $Lys(Gly)_4$; $(Gly)_3$ $AsnGlySer(Gly)_2$; $(Gly)_3$ Cys $(Gly)_4$; and GlyProAsnGlyGly.

To explain the above nomenclature, for example, $(Gly)_3$ $Lys(Gly)_4$ means Gly-Gly-Gly-Lys-Gly-Gly-Gly-Gly. Combinations of Gly and Ala are also preferred. The linkers shown here are exemplary and can be much longer and can include other residues.

Non-peptide linkers are also possible. For example, alkyl linkers such as $—NH—(CH_2)_s—C(O)—$, wherein s=2-20 could be used. These alkyl linkers can further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker, wherein the linker has a molecular weight of 100 to 5000 kD, for example, 100 to 500 kD. The peptide linkers can be altered to form derivatives in the same manner as described above.

Derivatives

In some embodiments, the neutralizing PCSK9 variant (and/or the vehicle) is derivatized. Such derivatives can improve the solubility, absorption, biological half life, and the like of the compounds. The moieties can alternatively eliminate or attenuate any undesirable side-effect of the compounds and the like. In some embodiments, the moiety can add additional properties to the molecule as a whole. Exemplary derivatives are provided herein.

The neutralizing PCSK9 variant or some portion thereof is cyclic. For example, the peptide portion can be modified to contain two or more Cys residues (e.g., in the linker), which could cyclize by disulfide bond formation.

The neutralizing PCSK9 variant is cross-linked or is rendered capable of cross-linking between molecules. For example, the peptide portion can be modified to contain one Cys residue and thereby be able to form an intermolecular disulfide bond with a like molecule. The compound can also be cross-linked through its C-terminus.

One or more peptidyl [—C(O)NR—] linkages (bonds) is replaced by a non-peptidyl linkage. Exemplary non-peptidyl linkages are —CH$_2$-carbamate [—CH$_2$—OC(O)NR—], phosphonate, —CH$_2$-sulfonamide [—CH$_2$—S(O)$_2$NR—], urea [—NHC(O)NH—], —CH$_2$-secondary amine, and alkylated peptide [—C(O)NR$_6$— wherein R$_6$ is lower alkyl].

The N-terminus is derivatized. Typically, the N-terminus can be acylated or modified to a substituted amine. Exemplary N-terminal derivative groups include —NRR$_1$ (other than —NH$_2$), —NRC(O)R$_4$, —NRC(O)OR$_1$, —NRS(O)$_2$R$_1$, —NHC(O)NHR$_1$, succinimide, or benzyloxycarbonyl-NH— (CBZ—NH—), wherein R and R$_1$ are each independently hydrogen or lower alkyl and wherein the phenyl ring can be substituted with 1 to 3 substituents selected from the group consisting of $C_1$-$C_4$ alkyl, $C_1$-$C_4$ alkoxy, chloro, and bromo.

The free C-terminus is derivatized. Typically, the C-terminus is esterified or amidated. For example, one can use methods described in the art to add (NH—CH$_2$—CH$_2$—NH$_2$)$_2$ to neutralizing PCSK9 variants. Likewise, one can use methods described in the art to add —NH$_2$ to neutralizing PCSK9 variants. Exemplary C-terminal derivative groups include, for example, —C(O)R$_2$ wherein R$_2$ is lower alkoxy or —NR$_3$, R$_4$ wherein R$_3$ and R$_4$ are independently hydrogen or $C_1$-$C_8$ alkyl (preferably $C_1$-$C_4$ alkyl).

A disulfide bond is replaced with another, preferably more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9. 8. One or more individual amino acid residues are modified. Various derivatizing agents are known to react specifically with selected sidechains or terminal residues, as described in detail below.

Lysinyl residues and amino terminal residues can be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues can be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents can react with the groups of lysine as well as the arginine epsilon-amino group. Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Carboxyl sidechain groups (aspartyl or glutamyl) can be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions. Glutaminyl and asparaginyl residues can be deamidated to the corresponding glutamyl and aspartyl residues. Alternatively, these residues are deamidated under mildly acidic conditions. Cysteinyl residues can be replaced by amino acid residues or other moieties either to eliminate disulfide bonding or, conversely, to stabilize cross-linking. See, e.g., Bhatnagar et al. (1996), J. Med. Chem. 39: 3814-9.

Derivatization with bifunctional agents can be useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming cross-links in the presence of light. Alternatively, reactive water-insoluble matrices such as cyanogen bromide-activated carbohydrates and the reactive substrates described in U.S.

Pat. Nos. 3,969,287; 3,691,016; 4,195,128; 4,247,642; 4,229,537; and 4,330,440 are employed for protein immobilization.

Carbohydrate (oligosaccharide) groups can be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, can confer acidic properties to the glycosylated compound. Such site(s) can be incorporated in the linker of the neutralizing PCSK9 variant and can be glycosylated by a cell during recombinant production of the polypeptide compounds (e.g., in mammalian cells such as CHO, BHK, COS). However, such sites can further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, Proteins: Structure and Molecule Properties (W. H. Freeman & Co., San Francisco), pp. 79-86 (1983).

In some embodiments, cysteine(s), arginine(s), and/or lysine(s) can be introduced into the neutralizing PCSK9 variant as a cite(s) of pegylation.

Neutralizing PCSK9 variants can be changed at the DNA level, as well. The DNA sequence of any portion of the compound can be changed to codons more compatible with the chosen host cell. Codons can be substituted to eliminate restriction sites or to include silent restriction sites, which can aid in processing of the DNA in the selected host cell. The vehicle, linker and peptide DNA sequences can be modified to include any of the foregoing sequence changes.

In some embodiments, neutralizing PCSK9 variants include glycosylation wherein the number and/or type of glycosylation site has been altered compared to the amino acid sequences of a parent polypeptide. In some embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred variants include cysteine variants wherein one or more cysteine residues are deleted from or substituted for another amino acid (e.g., serine) as compared to the parent amino acid sequence. Cysteine variants generally have fewer cysteine residues than the native protein, and typically have an even number to minimize interactions resulting from unpaired cysteines.

In some embodiments, the neutralizing PCSK9 variant is associated with at least a part of an antibody. In some embodiments, the neutralizing PCSK9 variant is part of an antibody fusion protein. As will be appreciated by one of skill in the art, a fusion protein can include various antibody sequences. In some embodiments, the neutralizing PCSK9 variant is fused to a full length antibody. In some embodiments, the neutralizing PCSK9 variant is fused to an antibody that binds to LDLR, thereby further increasing the likelihood that the neutralizing PCSK9 variant will be directed to its target. Non-neutralizing antibody fusions also form an aspect of the present invention. In this embodiment the non-neutralizing antibody fused to a PCSK9 variant can perform the function of increasing the half life of the PCSK9 variant.

In some embodiments, as noted above, the neutralizing PCSK9 variant is fused to a fragment of an antibody, such as a Fc domain. In some embodiments, the fusion protein will comprise, consist, or consist essentially of a Fe domain. In some embodiments, the fusion protein will comprise, consist, or consist essentially of a native Fc region. In some embodiments, the antibody or binding fragment thereof that is attached or fused to the neutralizing PCSK9 variant will bind to LDLR.

In some embodiments, any of the herein disclosed neutralizing PCSK9 variants, including antibody fusions, can be made from nucleic acid sequences encoding such protein sequences. Thus, nucleic acid sequences, vectors, and cells comprising these compounds are also contemplated herein.

In some embodiments, the neutralizing PCSK9 variant binds to a LDLR variant. In some embodiments, the variants of LDLR are at least 50% identical to human LDLR. It is noted that variants of LDLR are known to those of skill in the art (e.g., Brown M S et al, "Calcium cages, acid baths and recycling receptors" Nature 388: 629-630, 1997). In some embodiments, the neutralizing PCSK9 variant can raise the level of effective LDLR in heterozygote familial hypercholesterolemia (where a loss-of function variant of LDLR is present). Three exemplary LDLR sequences are shown in FIGS. 1I-1L (mouse, cynomolgus monkey, and human amino acid sequences). In some embodiments, the neutralizing PCSK9 variant will bind to a protein comprising at least one of the sequences in FIG. 1I-1L. In some embodiments the native PCSK9 variant will bind to a LDLR variant that comprises, consists, or consists essentially of the consensus sequence in FIGS. 1I-1L. In some embodiments, the LDLR variant will comprise each of the conserved amino acids identified in the consensus sequence in FIGS. 1I-1L. As will be appreciated by one of skill in the art, the space(s) in the consensus sequence can be filled with any of the other amino acids in the comparison at the corresponding location, or, in some embodiments, any amino acid.

In some embodiments, the neutralizing PCSK9 variant binds to and blocks LDLR from binding to other variants of PCSK9. These variants of PCSK9 are at least 50%, 50-60, 60-70, 70-80, 80-90, 90-95, 95-99, or greater percent identity to the form of PCSK9 depicted in FIG. 1A. In some embodiments, the neutralizing PCSK9 variant is a human variant, such as variants at position 474. In some embodiments, the amino acid at position 474 is valine (as in other humans) or threonine (as in cyno and mouse).

In some embodiments, variants of PCSK9 are contemplated, wherein one freely mutates the amino acids on the exterior of PCSK9, while conservatively altering those inside of PCSK9. In some embodiments, variants of PCSK9 are contemplated where one does not or only conservatively alters those residues on the binding surface between PCSK9 and LDLR, while freely or conservatively altering the residues on the rest of the PCSK9 surface or the inside of the protein. Various neutralizing PCSK9 variants are discussed herein and in the above sections.

In some embodiments, the neutralizing PCSK9 variant comprises a protein that has a sequence that start at residues 31 or 61 of SEQ ID NO: 3 (and variants thereof) and ends at any one of residues 447, 448, 449, 450, 451, 452, or 453 of SEQ ID NO: 3 (and variants thereof). Thus, in some embodiments, the neutralizing PCSK9 variant can include residues 31-447, 31-448, 31-449, 31-450, 31-451, 31-452, 31-453, 61-447, 61-448, 61-449, 61-450, 61-451, 61-452, and 61-453 of SEQ ID NO: 3 (and variants thereof) and/or a consensus sequence (e.g., shown in FIGS. 1C-1E, FIG. 1R$_1$-1R$_2$ (SEQ ID NO: 30) and FIG. F-H (for the Cat domain). In some embodiments, variants can be 50% or more (e.g., 50-60, 60-70, 70-80, 80-90, 90-95, 95-98, 98-99, or 99-100 percent) identical to the pro/cat domain of SEQ ID NO: 3 over the specific sequence length. In some embodiments, the neutralizing PCSK9 variant is at least 50, 55, 60, 65, 70, 75, 80, 85, 90, 95, 96, 97, 98, 99%, or more identical for the conserved sections of the pro/cat domain. In some embodiments, while the sections of the pro/cat domain in the neutralizing PCSK9 variant that are 100% conserved (e.g., as shown in FIGS. 1C-1E) are present, the remaining positions can be changed. In some embodiments, the changes in these remaining positions can result in a pro/cat section in the neutralizing PCSK9 variant that is 50-60, 60-70, 70-80, 80-90, 90-95, 95-98, 98-99, or 99-100 percent identical to the corresponding pro/cat domain of SEQ ID NO: 3.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure. In view of such information, one skilled in the art can predict the alignment of amino acid residues of a protein fragment with respect to its three dimensional structure. In some embodiments, one skilled in the art can choose not to make radical changes to amino acid residues predicted to be on the surface of the protein, since such residues can be involved in important interactions with other molecules. Moreover, one skilled in the art can generate and test variants containing a single amino acid substitution at each desired amino acid residue. The variants can then be screened using activity assays known to those skilled in the art, or as described in the Examples disclosed herein. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999).

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci. USA, 84(13): 4355-4358 (1987)), and "evolutionary linkage" (See Holm, supra (1999), and Brenner, supra (1997)).

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiocochemical or functional properties on such polypeptides. According to certain embodiments, single or multiple amino acid substitutions (in some embodiments, conservative amino acid substitutions) can be made in the naturally-occurring sequence (in some embodiments, in the portion of the polypeptide outside the domain(s) forming intermolecular contacts). In some embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden & J. Tooze, eds., Garland Publishing, New York, N.Y. (1991)); and Thornton et al., Nature, 354:105 (1991), which are each incorporated herein by reference.

In some embodiments, the neutralizing PCSK9 variant (or nucleic acid sequence encoding it) is a variant if the nucleic acid sequence that encodes the particular neutralizing PCSK9 variant can selectively hybridize to any of the nucleic acid sequences that encode the protein in SEQ ID NO: 3 under moderately stringent or stringent conditions. In one embodiment, suitable moderately stringent conditions include prewashing in a solution of 5×SSC; 0.5% SDS, 1.0 mM EDTA (pH 8:0); hybridizing at 50° C., –65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode a variant that is encoded by a hybridizing DNA sequence and the amino acid sequences that are encoded by these nucleic acid sequences. In some embodiments, suitable high stringency conditions are used and include hybridization at about 65° C. in 0.1×SSC. In some embodiments, suitable high stringency conditions include washing in 0.1×SSPE and 0.2% SDS at 65° C. for 15 minutes. In some embodiments, suitable high stringency conditions include 31% v/v to 50% v/v formamide and 0.01M to 0.15M salt at 42° C. and washing conditions of 0.1×SCC, 0.5% w/v SDS at 60° C. Such hybridizing DNA sequences are also within the scope of this invention, as are nucleotide sequences that, due to code degeneracy, encode a variant that is encoded by a hybridizing DNA sequence and the amino acid sequences that are encoded by these nucleic acid sequences.

The phrase "selectively hybridize" referred to in this context means to detectably and selectively bind. Such, polynucleotides, oligonucleotides, and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine and/or arginine, as has been previously described for "alanine scanning mutagenesis" and "arginine scanning mutagenesis."

Desired amino acid substitutions (whether conservative or non-conservative) can be determined by those skilled in the art at the time such substitutions are desired. In some embodiments, amino acid substitutions can be used to identify important residues of PCSK9, or to increase or decrease the affinity of the neutralizing PCSK9 variant as described herein.

Antibodies to Neutralizing PCSK9 Variants

In some embodiments, antibodies to any of the sequences or neutralizing PCSK9 variants described herein can be made and used. These antibodies are selective for the neutralizing PCSK9 variant over native PCSK9. In some embodiments, the antibody binds to a neutralizing PCSK9 variant that consists essentially of the Pro/Cat domain of PCSK9. In some embodiments, the antibody is selective for this neutralizing PCSK9 variant over wild-type PCSK9.

As will be appreciated by one of skill in the art, the antibodies can be created by raising antibodies to the neutralizing PCSK9 variant and then identifying those antibodies that will not bind (or will not bind as effectively as antibodies to native PCSK9) to native PCSK9. In some embodiments, the antibodies will bind to the neutralizing PCSK9 variant with a $K_D$ that is at least 1, 1-10, 10-50, or 50-100% better than the $K_D$ of the antibody to human PCSK9. In some embodiments, the antibodies will bind to the neutralizing PCSK9 variant with a $K_D$ that is at least 2-5, 5-10, 10-50, 50-100, 100-1000, 1000-10,000, 10,000-100, 000, or 100,000-$10^6$ better than the $K_D$ of the antibody for the native PCSK9. As will be appreciated by one of skill in the art, as the neutralizing PCSK9 variant will have an inactive V domain that can be structurally different (and even absent) from the wild type PCSK9 protein, such selective antibodies will be readily attainable given the present disclosure. In some embodiments, an adjuvant is used with the neutralizing PCSK9 variant to create the above antibodies.

As will be appreciated by one of skill in the art, the antibodies can be used to selectively observe the amount of the neutralizing PCSK9 variant without inadvertently detecting native PCSK9 as well.

Cell Lines and Expression of Neutralizing PCSK9 Variants

In some embodiments, neutralizing PCSK9 variants can be expressed in cell lines. In some embodiments, sequences encoding particular neutralizing PCSK9 variants can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In some embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In some embodiments, cell lines can be selected through determining which cell lines have high expression levels. Appropriate expression vectors for mammalian host cells are well known.

In some embodiments, any of a variety of expression vector/host systems can be utilized to express polynucleotide molecules encoding polypeptides comprising one or more protein segments. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In some embodiments, a polypeptide comprising one or more neutralizing PCSK9 variant is recombinantly expressed in yeast. Certain such embodiments use commercially available expression systems, e.g., the Pichia Expression System (Invitrogen, San Diego, Calif.), following the manufacturer's instructions. In some embodiments, such a system relies on the pre-pro-alpha sequence to direct secretion. In some embodiments, transcription of the insert is driven by the alcohol oxidase (AOX1) promoter upon induction by methanol.

In some embodiments, a secreted polypeptide comprising one or more neutralizing PCSK9 variant is purified from yeast growth medium. In some embodiments, the methods used to purify a polypeptide from yeast growth medium is the same as those used to purify the polypeptide from bacterial and mammalian cell supernatants.

In some embodiments, a nucleic acid encoding a polypeptide comprising one or more neutralizing PCSK9 variant is cloned into a baculovirus expression vector, such as pVL1393 (PharMingen, San Diego, Calif.). In some embodiments, such a vector can be used according to the manufacturer's directions (PharMingen) to infect Spodoptera frugiperda cells in sF9 protein-free media and to produce recombinant polypeptide. In some embodiments, a polypeptide is purified and concentrated from such media using a heparin-Sepharose column (Pharmacia).

In some embodiments, a polypeptide comprising one or more neutralizing PCSK9 variant is expressed in an insect system. Certain insect systems for polypeptide expression are well known to those of skill in the art. In one such system, Autographa californica nuclear polyhedrosis virus (AcNPV) is used as a vector to express foreign genes in Spodoptera frugiperda cells or in Trichoplusia larvae. In some embodiments, a nucleic acid molecule encoding a polypeptide can be inserted into a nonessential gene of the virus, for example, within the polyhedrin gene, and placed under control of the promoter for that gene. In some embodiments, successful insertion of a nucleic acid molecule will render the nonessential gene inactive. In some embodiments, that inactivation results in a detectable characteristic. For example, inactivation of the polyhedrin gene results in the production of virus lacking coat protein.

In some embodiments, recombinant viruses can be used to infect S. frugiperda cells or Trichoplusia larvae. See, e.g., Smith et al., J. Virol., 46: 584 (1983); Engelhard et al., Proc. Nat. Acad. Sci. (USA), 91: 3224-7 (1994).

In some embodiments, polypeptides comprising one or more neutralizing PCSK9 variant made in bacterial cells are produced as insoluble inclusion bodies in the bacteria. In some embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In some embodiments, the lysate is cleared by sonication, and cell debris is pelleted by centrifugation for 10 minutes at 12,000×g. In some embodiments, the polypeptide-containing pellet is resuspended in 50 mM Tris, pH 8, and 10 mM EDTA; layered over 50% glycerol; and centrifuged for 30 minutes at 6000×g. In some embodiments, that pellet can be resuspended in standard phosphate buffered saline solution (PBS) free of $Mg^{++}$ and $Ca^{++}$. In some embodiments, the polypeptide is further purified by fractionating the resuspended pellet in a denaturing SDS polyacrylamide gel (See, e.g., Sambrook et al., supra). In some embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In some embodiments, such GST fusion protein is purified using a GST Purification Module (Pharmacia).

In some embodiments, it is desirable to "refold" certain polypeptides, e.g., polypeptides comprising one or more neutralizing PCSK9 variant. In some embodiments, such polypeptides are produced using certain recombinant systems discussed herein. In some embodiments, polypeptides are "refolded" and/or oxidized to form desired tertiary structure and/or to generate disulfide linkages. In some embodiments, such structure and/or linkages are related to certain biological activity of a polypeptide. In some embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In some embodiments, the refolding/oxidation solution also contains a reducing agent and the oxidized form of that reducing agent. In some embodiments, the reducing agent and its oxidized form are present in a ratio that will generate a particular redox potential that allows disulfide shuffling to occur. In some embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In some embodiments, a co-solvent is used to increase the efficiency of refolding. Exemplary cosolvents include, but are not limited to, glycerol, polyethylene glycol of various molecular weights, and arginine.

In some embodiments, a polypeptide comprising one or more neutralizing PCSK9 variants is substantially purified. Certain protein purification techniques are known to those of skill in the art. In some embodiments, protein purification involves crude fractionation of polypeptide fractionations from non-polypeptide fractions. In some embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In some embodiments, a polypeptide is purified by fast protein liquid chromatography or by high pressure liquid chromatography (HPLC). In some embodiments, purification steps can be changed or certain steps can be omitted, and still result in a suitable method for the preparation of a substantially purified polypeptide.

In some embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In some embodiments, the results of such a calculation are expressed as "fold purification." The units used to represent the amount of binding activity depend upon the particular assay performed.

In some embodiments, a polypeptide comprising one or more neutralizing PCSK9 variants is partially purified. In some embodiments, partial purification can be accomplished by using fewer purification steps or by utilizing different forms of the same general purification scheme. For example, in some embodiments, cation-exchange column chromatography performed utilizing an HPLC apparatus will generally result in a greater "fold purification" than the same technique utilizing a low-pressure chromatography system. In some embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al., Biochem. Biophys. Res. Comm., 76: 425 (1977). It will be appreciated that under different electrophoresis conditions, the apparent molecular weights of purified or partially purified polypeptide can be different.

Examples of Therapeutic uses and Pharmaceutical Compositions

In certain instances, PCSK9 activity correlates with a number of human disease states. For example, in certain instances, too much or too little PCSK9 activity correlates with certain conditions, such as hypercholesterolemia. Therefore, in certain instances, modulating PCSK9 activity can be therapeutically useful.

In some embodiments, a neutralizing PCSK9 variant is used to modulate at least one native PCSK9 activity (e.g., binding of native PCSK9 to LDLR). Such methods can treat and/or prevent and/or reduce the risk of disorders that relate to elevated serum cholesterol levels or in which elevated cholesterol levels are relevant.

As will be appreciated by one of skill in the art, in light of the present disclosure, disorders that relate to, involve, or can be influenced by varied cholesterol, LDL, or LDLR levels can be addressed by various embodiments of the neutralizing PCSK9 variants. The neutralizing PCSK9 variants can be used in a variety of therapeutic applications. For example, in some embodiments the neutralizing PCSK9 variants are useful for treating conditions associated with PCSK9, such as cholesterol related disorders (or "serum cholesterol related disorders") such as hypercholesterolemia, as further described herein. Some of the neutralizing PCSK9 variants described herein are useful in treating consequences, symptoms, and/or the pathology associated with PCSK9 activity.

In some embodiments, a "cholesterol related disorder" (which includes "serum cholesterol related disorders") includes any one or more of the following: hypercholesterolemia, heart disease, metabolic syndrome, diabetes, coronary heart disease, stroke, cardiovascular diseases, Alzheimers disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using a neutralizing PCSK9 variant, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apoplipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. Neutralizing PCSK9 variants can also be useful in preventing or treating atherosclerotic diseases, such as, for example, coronary heart disease, coronary artery disease, peripheral arterial disease, stroke (ischaemic and hemorrhagic), angina pectoris, or cerebrovascular disease and acute coronary syndrome, myocardial infarction. In some embodiments, the neutralizing PCSK9 variant is useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In some embodiments, a neutralizing PCSK9 variant of PCSK9 and methods can be used to reduce the risk of recurrent cardiovascular events.

As will be appreciated by one of skill in the art, diseases or disorders that are generally addressable (either treatable or preventable) through the use of statins can also benefit from the application of the instant neutralizing PCSK9 variants. In addition, in some embodiments, disorders or diseases that can benefit from the prevention of cholesterol synthesis or increased LDLR expression can also be treated by various embodiments of the neutralizing PCSK9 variants. In addition, as will be appreciated by one of skill in the art, the use of the neutralizing PCSK9 variants can be especially useful in the treatment of Diabetes. Not only is Diabetes a risk factor for coronary heart disease, but insulin increases the expression of PCSK9. That is, people with Diabetes have elevated plasma lipid levels (which can be related to high PCSK9 levels) and can benefit from lowering those levels or modulating the activity of those levels. This is generally discussed in more detail in Costet et al. ("Hepatic PCSK9 Expression is Regulated by Nutirtional Status via Insulin and Sterol Regulatiory Element-binding Protein 1C", J. Biol. Chem., 281: 6211-6218, 2006), the entirety of which is incorporated herein by reference.

In some embodiments, the neutralizing PCSK9 variant is administered to those who have diabetes mellitus, abdominal aortic aneurysm, atherosclerosis and/or peripheral vascular disease in order to decrease their serum cholesterol levels to a safer range. In some embodiments, the neutralizing PCSK9 variant is administered to patients at risk of developing any of the herein described disorders. In some embodiments, the neutralizing PCSK9 variants are administered to subjects that smoke, have hypertension or a familial history of early heart attacks.

In some embodiments, a subject is administered a neutralizing PCSK9 variant if they are at a moderate risk or higher on the 2004 NCEP treatment goals. In some embodiments, the neutralizing PCSK9 variant is administered to a subject if the subject's LDL cholesterol level is greater than 160 mg/dl. In some embodiments, the neutralizing PCSK9 variant is administered if the subject's LDL cholesterol level is greater than 130 (and they have a moderate or moderately high risk according to the 2004 NCEP treatment goals). In some embodiments, the neutralizing PCSK9 variant is administered if the subjects LDL cholesterol level is greater than 100 (and they have a high or very high risk according to the 2004 NCEP treatment goals). In some embodiments, the neutralizing PCSK9 variant is administered if the subjects LDL cholesterol level does not reach a goal of less than 90, or less than 80, or less than 70 mg/dl. In some embodiments, the neutralizing PCSK9 variant is administered if the subject is intolerant or resistant to other lipid modifying regimens and medications.

A physician will be able to select an appropriate treatment based on the indications and target lipid levels depending on the individual profile of a particular patient. One well-accepted standard for guiding treatment of hyperlipidemia is the Third Report of the National Cholesterol Education Program (NCEP) Expert Panel on Detection, Evaluation, and Treatment of the High Blood Cholesterol in Adults (Adult Treatment Panel III) Final Report, National Institutes of Health, NIH Publication No. 02-5215 (2002), the printed publication of which is hereby incorporated by reference in its entirety.

In some embodiments, neutralizing PCSK9 variants to PCSK9 are used to decrease the amount of PCSK9 activity (degradation of PCSK9) from an abnormally high level or even a normal level. In some embodiments, neutralizing PCSK9 variants to PCSK9 are used to treat or prevent hypercholesterolemia and/or in the preparation of medicaments therefore and/or for other cholesterol related disorders (such as those noted herein). In some embodiments, a neutralizing PCSK9 variant is used to treat or prevent conditions such as hypercholesterolemia in which PCSK9 activity is normal. In such conditions, for example, reduction of PCSK9 activity to below normal can provide a therapeutic effect.

In some embodiments, more than one neutralizing PCSK9 variant is used to modulate native PCSK9 activity.

In some embodiments, methods are provided of treating a cholesterol related disorder, such as hypercholesterolemia comprising administering a therapeutically effective amount of one or more neutralizing PCSK9 variants and another therapeutic agent.

In some embodiments, a neutralizing PCSK9 variant is administered alone. In some embodiments, a neutralizing PCSK9 variant is administered prior to the administration of at least one other therapeutic agent. In some embodiments, a neutralizing PCSK9 variant is administered concurrent with the administration of at least one other therapeutic agent. In some embodiments, a neutralizing PCSK9 variant is administered subsequent to the administration of at least one other therapeutic agent. In other embodiments, a neutralizing PCSK9 variant is administered prior to the administration of at least one other therapeutic agent. Therapeutic agents (apart from the neutralizing PCSK9 variant), include, but are not limited to, at least one other cholesterol-lowering (serum and/or total body cholesterol) agent or an agent. In some embodiments, the agent increases the expression of LDLR, have been observed to increase serum HDL levels, lower serum LDL levels or lower triglyceride levels. Exemplary agents include, but are not limited to, statins (atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), Combining nicotinic acid with statin (ADVICOR (LOVASTATIN and NIASPAN), Combining a statin with an absorption inhibitor (VYTORIN (ZOCOR and ZETIA) and/or lipid modifying agents. In some embodiments, the neutralizing PCSK9 variant is combined with PPAR gamma agonists, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors), ApoB modulators, MTP inhibitors and/or arteriosclerosis obliterans treatments. In some embodiments, the neutralizing PCSK9 variant is combined with an agent that increases the level of LDLR protein in a subject, such as statins, certain cytokines like oncostatin M, estrogen, and/or certain herbal ingredients such as berberine. In some embodiments, the neutralizing PCSK9 variant is combined with an agent that increases serum cholesterol levels in a subject (such as certain anti-psycotic agents, certain HIV protease inhibitors, dietary factors such as high fructose, sucrose, cholesterol or certain fatty acids and certain nuclear receptor agonists and antagonists for RXR, RAR, LXR, FXR). In some embodiments, the neutralizing PCSK9 variant is combined with an agent that increases the level of PCSK9 in a subject, such as statins and/or insulin. The combination of the two can allow for the undesirable side-effects of other agents to be mitigated by the neutralizing PCSK9 variant. As will be appreciated by one of skill in the art, in some embodiments, the neutralizing PCSK9 variant is combined with the other agent/compound. In some embodiments, the neutralizing PCSK9 variant and other agent are administered concurrently. In some embodiments, the neutralizing PCSK9 variant and other agent are not administered simultaneously, with the neutralizing PCSK9 variant being administered before or after the agent is administered. In some embodiments, the subject receives both the neutralizing PCSK9 variant and the other agent (that increases the level of LDLR) during a same period of prevention, occurrence of a disorder, and/or period of treatment.

Pharmaceutical compositions can be administered in combination therapy, i.e., combined with other agents. In some embodiments, the combination therapy comprises a neutralizing PCSK9 variant, in combination with at least one anti-cholesterol agent. Agents include, but are not limited to, in vitro synthetically prepared chemical compositions, antibodies, antigen binding regions, and combinations and conjugates thereof. In some embodiments, an agent can act as an agonist, antagonist, allosteric modulator, or toxin. In some embodiments, an agent can act to inhibit or stimulate its target (e.g., receptor or enzyme activation or inhibition), and thereby promote increased expression of LDLR or decrease serum cholesterol levels.

In some embodiments, a neutralizing PCSK9 variant can be administered prior to, concurrent with, and subsequent to treatment with a cholesterol-lowering (serum and/or total cholesterol) agent. In some embodiments, a neutralizing PCSK9 variant can be administered prophylactically to prevent or mitigate the onset of hypercholesterolemia, heart disease, diabetes, and/or any of the cholesterol related disorder. In some embodiments, a neutralizing PCSK9 variant can be administered for the treatment of an existing hypercholesterolemia condition. In some embodiments, the neutralizing PCSK9 variant delays the onset of the disorder and/or symptoms associated with the disorder. In some embodiments, the neutralizing PCSK9 variant is provided to a subject lacking any symptoms of any one of the cholesterol related disorders or a subset thereof.

In some embodiments, a neutralizing PCSK9 variant is used with particular therapeutic agents to treat various cholesterol related disorders, such as hypercholesterolemia. In some embodiments, in view of the condition and the desired level of treatment, two, three, or more agents can be administered. In some embodiments, such agents can be provided together by inclusion in the same formulation. In some embodiments, such agent(s) and a neutralizing PCSK9 variant can be provided together by inclusion in the same formulation. In some embodiments, such agents can be formulated separately and provided together by inclusion in a treatment kit. In some embodiments, such agents and a neutralizing PCSK9 variant can be formulated separately and provided together by inclusion in a treatment kit. In some embodiments, such agents can be provided separately. In some embodiments, when administered by gene therapy, the genes encoding protein agents and/or a neutralizing PCSK9 variant can be included in the same vector. In some embodiments, the genes encoding protein agents and/or a neutralizing PCSK9 variant can be under the control of the same promoter region. In some embodiments, the genes encoding protein agents and/or a neutralizing PCSK9 variant can be in separate vectors.

In some embodiments, a pharmaceutical composition comprising a neutralizing PCSK9 variant is combined with a pharmaceutically acceptable diluent, carrier, solubilizer, emulsifier, preservative and/or adjuvant.

In some embodiments, a pharmaceutical compositions comprising a neutralizing PCSK9 variant and a therapeutically effective amount of at least one additional therapeutic agent are combined together with a pharmaceutically acceptable diluent, carrier, solubilizer, emulsifier, preservative and/or adjuvant.

In some embodiments, a neutralizing PCSK9 variant can be used with at least one therapeutic agent for inflammation. In some embodiments, a neutralizing PCSK9 variant can be used with at least one therapeutic agent for an immune disorder. Exemplary therapeutic agents for inflammation and immune disorders include, but are not limited to cyclooxygenase type 1 (COX-1) and cyclooxygenase type 2 (COX-2) inhibitors small molecule modulators of 38 kDa mitogen-activated protein kinase (p38-MAPK); small molecule modulators of intracellular molecules involved in inflammation pathways, wherein such intracellular molecules include, but are not limited to, jnk, NF-κB, ZAP70, and lck. Certain exemplary therapeutic agents for inflammation are described, e.g., in C. A. Dinarello & L. L. Moldawer *Proinflammatory and Anti-Inflammatory Cytokines in Rheumatoid Arthritis: A Primer for Clinicians* Third Edition (2001) Amgen Inc. Thousand Oaks, Calif.

In some embodiments, pharmaceutical compositions will include more than one different neutralizing PCSK9 variant(s). In some embodiments, pharmaceutical compositions will include more than one neutralizing PCSK9 variant wherein the neutralizing PCSK9 variants bind more than one epitope. In some embodiments, the various neutralizing PCSK9 variants will not compete with one another for binding to PCSK9.

In some embodiments, acceptable formulation materials preferably are nontoxic to recipients at the dosages and concentrations employed. In some embodiments, the formulation material(s) are for s.c. and/or I.V. administration. In some embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In some embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1995).

As noted above, in some embodiments, a neutralizing PCSK9 variant and/or a therapeutic molecule is linked to a half-life extending vehicle known in the art. Such vehicles include, but are not limited to, polyethylene glycol, glycogen (e.g., glycosylation of the neutralizing PCSK9 variant), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In some embodiments, the optimal pharmaceutical composition can be determined by one skilled in the art depending upon, for example, the intended route of administration, delivery format and desired dosage. See, for example, *Remington's Pharmaceutical Sciences*, supra. In some embodiments, such compositions may influence the physical state, stability, rate of in vivo release and rate of in vivo clearance of the variants of PCSK9.

In some embodiments, the primary vehicle or carrier in a pharmaceutical composition can be either aqueous or non-aqueous in nature. For example, in some embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In some embodiments, neutral buffered saline or saline mixed with serum albumin are further exemplary vehicles. In some embodiments, pharmaceutical compositions comprise Tris buffer of about pH 7.0-8.5, or acetate buffer of about pH 4.0-5.5, which can further include sorbitol or a suitable substitute therefore. In some embodiments, a composition comprising a neutralizing PCSK9 variant, with or without at least one additional therapeutic agents, can be prepared for storage by mixing the selected composition having the desired degree of purity with optional formulation agents (*Remington's Pharmaceutical Sciences*, supra) in the form of a lyophilized cake or an aqueous solution. Further, in some embodiments, a composition comprising a neutralizing PCSK9 variant, with or without at least one additional therapeutic agent, can be formulated as a lyophilizate using appropriate excipients such as sucrose.

In some embodiments, the pharmaceutical composition can be selected for parenteral delivery. In some embodiments, the compositions can be selected for inhalation or for delivery through the digestive tract, such as orally. The preparation of such pharmaceutically acceptable compositions is within the ability of one skilled in the art.

In some embodiments, the formulation components are present in concentrations that are acceptable to the site of administration. In some embodiments, buffers are used to maintain the composition at physiological pH or at a slightly lower pH, typically within a pH range of from about 5 to about 8.

In some embodiments, when parenteral administration is contemplated, a therapeutic composition can be in the form of a pyrogen-free, parenterally acceptable aqueous solution comprising a desired neutralizing PCSK9 variant, with or without additional therapeutic agents, in a pharmaceutically acceptable vehicle. In some embodiments, a vehicle for parenteral injection is sterile distilled water in which a neutralizing PCSK9 variant, with or without at least one additional therapeutic agent, is formulated as a sterile, isotonic solution, properly preserved. In some embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In some embodiments, hyaluronic acid can also be used, and can have the effect of promoting sustained duration in the circulation. In some embodiments, implantable drug delivery devices can be used to introduce the desired molecule.

In some embodiments, a pharmaceutical composition can be formulated for inhalation. In some embodiments, a neutralizing PCSK9 variant, with or without at least one additional therapeutic agent, can be formulated as a dry powder for inhalation. In some embodiments, an inhalation solution comprising a neutralizing PCSK9 variant, with or without at least one additional therapeutic agent, can be formulated with a propellant for aerosol delivery. In some embodiments, solutions can be nebulized. Pulmonary administration is further described in PCT application no. PCT/US94/001875, which describes pulmonary delivery of chemically modified proteins.

In some embodiments, it is contemplated that formulations can be administered orally. In some embodiments, a neutralizing PCSK9 variant, with or without at least one additional therapeutic agents, that is administered in this fashion can be formulated with or without those carriers customarily used in the compounding of solid dosage forms such as tablets and capsules. In some embodiments, a capsule can be designed to release the active portion of the formulation at the point in the gastrointestinal tract when bioavailability is maximized and pre-systemic degradation is minimized. In some embodiments, at least one additional agent can be included to facilitate absorption of a neutralizing PCSK9 variant and/or any additional therapeutic agents. In some embodiments, diluents, flavorings, low melting point waxes, vegetable oils, lubricants, suspending agents, tablet disintegrating agents, and binders can also be employed.

In some embodiments, a pharmaceutical composition can involve an effective quantity of a neutralizing PCSK9 variant, with or without at least one additional therapeutic agent, in a mixture with non-toxic excipients which are suitable for the manufacture of tablets. In some embodiments, by dissolving the tablets in sterile water, or another appropriate vehicle, solutions can be prepared in unit-dose form. In some embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving neutralizing PCSK9 variants, with or without at least one additional therapeutic agent(s), in sustained- or controlled-delivery formulations. In some embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In some embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly(2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In some embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In some embodiments, this can be accomplished by filtration through sterile filtration membranes. In some embodiments, where the composition is lyophilized, sterilization using this method can be conducted either prior to or following lyophilization and reconstitution. In some embodiments, the composition for parenteral administration can be stored in lyophilized form or in a solution. In some embodiments, parenteral compositions generally are placed into a container having a sterile access port, for example, an intravenous solution bag or vial having a stopper pierceable by a hypodermic injection needle. In some embodiments, the pharmaceutical composition is sterile.

In some embodiments, the pharmaceutical composition will comprise at least a sufficient amount of the neutralizing PCSK9 variant to reduce an amount of native PCSK9 from binding in a human, in vivo. In some embodiments the pharmaceutical composition will comprise at least a sufficient amount of the neutralizing PCSK9 variant to reduce a symptom of a "cholesterol related disorder" (which includes "serum cholesterol related disorders"). In some embodiments the pharmaceutical composition will comprise at least a sufficient amount of the neutralizing PCSK9 variant to modulate at least one native PCSK9 activity (e.g., binding of native PCSK9 to LDLR).

In some embodiments, the pharmaceutical composition comprises at least an amount of a neutralizing PCSK9 variant sufficient for treating any one or more of the cholesterol related disorders disclosed herein.

In some embodiments, the pharmaceutical composition comprises at least an amount of a neutralizing PCSK9 variant sufficient to treat a symptom of a cholesterol related disorder of an adult male and/or female. In some embodiments the amount of the neutralizing PCSK9 variant is at least sufficient to treat (e.g., reduce a symptom of) an adult male weighing between 10 and 250 kg. In some embodiments, the amount is at least sufficient to treat a 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kg subject so as to lessen a symptom of at least any one of the cholesterol related disorders, to raise the level of LDLR in the subject, or to lower the level of LDL in the subject. In some embodiments, the amount of a neutralizing PCSK9 variant present in the pharmaceutical composition is at least sufficient to raise the level of LDLR in a subject by some detectable amount. In some embodiments, the level of LDLR in a subject is raised by at least 1, 2, 3, 4, 5, 6, 7, 8, 9, 10, 10, 15, 20, 25, 30, 35, 40, 45, 50, 55, 60, 65, 70, 75, 80, 85, 90, 95, 100 percent. In some embodiments the level of LDLR in a subject is increased by at least 2, 3, 4, 5, 6, 7, 8, 9, 10, 20, 30, 40, 50, 60, 70, 80, 90, or 100 fold over an untreated healthy subject and/or over an untreated subject that has a cholesterol related disorder. In yet other embodiments the neutralizing PCSK9 variant is sufficient to maintain the level of LDLR in a subject at a desired level. The appropriate level can be determined by the subject's health care provider and can take into account particular aspects of the subject's physical condition and health issues and concerns.

In some embodiments, the amount of neutralizing PCSK9 variant present in the pharmaceutical composition is at least sufficient to block a significant amount of the activity of the native PCSK9 in vivo. In some embodiments, the amount is sufficient to block at least 1% of the activity of native PCSK9, for example, at least 1, 1-10, 10-20, 20-30, 30-40, 40-50, 50-60, 60-70, 70-80, 80-90, 90-95, 95-98, 98-99, 99-100 percent of the native PCSK9 is blocked by the amount of PCSK9 present in the pharmaceutical composition.

In some embodiments, the amount of neutralizing PCSK9 variant present in the pharmaceutical composition is at least sufficient to lower serum LDL in a subject. In some embodiments, the amount is sufficient to lower the amount of serum LDL in a subject by at least 1% of the native level of serum LDL, for example, at least 1, 1-10, 10-20, 20-30, 30-40, 40-50, 50-60, 60-70, 70-80, 80-90, 90-95, 95-98, 98-99, 99-100 percent of the level of serum LDL for the subject, for a subject having a cholesterol related disorder, or for a healthy subject.

In some embodiments, the amount of neutralizing PCSK9 variant present in the pharmaceutical composition is a significant amount. In some embodiments, the amount of neutralizing PCSK9 variant present in a pharmaceutical dose to be given to a subject is at least 1 ng, for example, the amount is at least 1, 10, 20, 50, 100, 500, 1000, 10,000, $10^5$, $10^6$, $10^7$, $10^8$, $10^9$, $10^{10}$, or $10^{11}$ nanograms, including any amount defined between any two of the previous numbers and any amount above any of the previous numbers. In some embodiments the amount is in a single pill. In some embodiments, the amount is in multiple pills. In some embodiments, the amount of the neutralizing PCSK9 variant administered is from about 1 to 500 mg, 50 to 400 mg, or 100 to 300 mg.

In some embodiments, the neutralizing PCSK9 variant is included in a solid form, such as in a tablet or pill.

In some embodiments, the amount of the neutralizing PCSK9 variant is a dosage sufficient to achieve any of the herein described goals (or amounts) for at least 1 hour. In some embodiments, the amount is sufficient to treat a cholesterol related disorder for at least one hour, for example, 1, 2, 3, 4, 5, 6, 7, 8, 9, 10, 11, 12, 13, 14, 15, 16, 17, 18, 19, 20, 21, 22, 23, or 24 hours. In some embodiments, the amount of the neutralizing PCSK9 variant that is present is sufficient to achieve any of the herein described goals for at least one day. Thus, in some embodiments, the dosage is a once daily amount.

In some embodiments, the neutralizing PCSK9 variant is relatively pure. In some embodiments, apart from a pharmaceutical acceptable carrier or diluent and the neutralizing PCSK9 variant, nothing else is present in the composition. In some embodiments, a compound comprising the neutralizing PCSK9 variant is at least 0.01% neutralizing PCSK9 variant (by weight). In some embodiments, at least $1\times10^{-8}$, $1\times10^{-7}$, $1\times10^{-6}$, $1\times10^{-5}$, 0.0001, 0.001, 0.01, 0.1, 1, 2, 3, 4, 5, 6, 7, 8, 9, 10, 15, 20, 25, 30, 35, 40, 45, 50, 55, 60, 65, 70, 75, 80, 85, 90, 95, 98, 99, or 100 percent of the compound is a neutralizing PCSK9 variant. In some embodiments, the percent is a range defined between any two of the previous percents.

As will be appreciated by one of skill in the art, any of the above parameters describing the amount of the neutralizing PCSK9 variant present can be combined with any of the other parameters. For example, any of the parameters regarding the percent of native PCSK9 blocked in vivo can be combined for any of the specific weights supplied for the subjects.

In some embodiments, the pharmaceutical composition does not include ingredients that are harmful to a subject.

In some embodiments, the pharmaceutical composition does not include 50 mM sodium phosphate and/or 50 mM sodium chloride. In some embodiments, the pharmaceutical composition does not include sodium phosphate and/or sodium chloride. In some embodiments the pharmaceutical composition does not contain cell lysates. In some embodiments the pharmaceutical composition does not contain cell medium. In some embodiments, the pharmaceutical composition does not include BS3 (bis[sulfosuccinimidyl]suberate). In some embodiments, the pharmaceutical composition does not include potassium formate. In some embodiments, the pharmaceutical composition does not include PEG 3350. In some embodiments, the pharmaceutical composition does not include 0.2 M potassium formate. In some embodiments, the pharmaceutical composition does not include 20% PEG 3350. In some embodiments, the pharmaceutical composition does not include 50 mM Tris. In some embodiments, the pharmaceutical composition does not include 4 mM EDTA. In some embodiments, the pharmaceutical composition does not include 0.01-2% Triton X-100. In some embodiments, the pharmaceutical composition does not include 0.5 sodium deoxycholate. In some embodiments, the pharmaceutical composition does not include 0.1-2% sodium dodecyl sulfate. In some embodiments, the pharmaceutical composition does not include 10-20% glycerol. In some embodiments, the pharmaceutical composition does not include 1M NDSB. In some embodiments, the pharmaceutical composition does not include 1-20 mM calcium chloride. In some embodiments, the pharmaceutical composition does not include $KH_2PO_4$/NaOH. In some embodiments, the pharmaceutical composition does not include citric acid and sodium phosphate. In some embodiments, the pharmaceutical composition does not include $Na_2HPO_4$ and NaOH. In some embodiments, the pharmaceutical composition does not include the combination of two or more of the above ingredients. In some embodiments, the pharmaceutical composition does not include the combination of three or more of the above ingredients. In some embodiments, the pharmaceutical composition does not include the combination of four or more of the above ingredients. In some embodiments, the pharmaceutical composition does include one or more of the above ingredients.

In some embodiments, the neutralizing PCSK9 variant is not created in *E. coli*. In some embodiments, any of the herein disclosed neutralizing PCSK9 variants is a self-processed or self-cleaved protein. In some embodiments, any of the herein disclosed neutralizing PCSK9 variants is a processed or cleaved protein.

In some embodiments, once the pharmaceutical composition has been formulated, it can be stored in sterile vials as a solution, suspension, gel, emulsion, solid, or as a dehydrated or lyophilized powder. In some embodiments, such formulations can be stored either in a ready-to-use form or in a form (e.g., lyophilized) that is reconstituted prior to administration.

In some embodiments, kits are provided for producing a single-dose administration unit. In some embodiments, the kit can contain both a first container having a dried protein and a second container having an aqueous formulation. In some embodiments, kits containing single and multi-chambered pre-filled syringes (e.g., liquid syringes and lyosyringes) are included.

In some embodiments, the effective amount of a pharmaceutical composition comprising a neutralizing PCSK9 variant, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a neutralizing PCSK9 variant, with or without at least one additional therapeutic agent, is being used, the route of administration, and the size (body weight, body surface or organ size) and/or condition (the age and general health) of the patient. In some embodiments, a clinician can titer the dosage and modify the route of administration to obtain the optimal therapeutic effect. In some embodiments, a typical dosage can range from about 0.1 µg/kg to up to about 100 mg/kg or more, depending on the factors mentioned above. In some embodiments, the dosage can range from 0.1 µg/kg up to about 100 mg/kg; or 1 µg/kg up to about 100 mg/kg; or 5 µg/kg up to about 100 mg/kg.

In some embodiments, the frequency of dosing will take into account the pharmacokinetic parameters of a neutralizing PCSK9 variant and/or any additional therapeutic agents in the formulation used. In some embodiments, a clinician will administer the composition until a dosage is reached that achieves the desired effect. In some embodiments, the composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In some embodiments, appropriate dosages can be ascertained through use of appropriate dose-response data. In some embodiments, the amount and frequency of administration can take into account the desired cholesterol level (serum and/or total) to be obtained and the subject's present cholesterol level, LDL level, and/or LDLR levels, all of which can be obtained by methods that are well known to those of skill in the art.

In some embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In some embodiments, the compositions can be administered by bolus injection or continuously by infusion, or by implantation device. In some embodiments, the composition is configured for administration via any of these routes.

In some embodiments, the composition can be administered locally via implantation of a membrane, sponge or another appropriate material onto which the desired molecule has been absorbed or encapsulated. In some embodiments, where an implantation device is used, the device can be implanted into any suitable tissue or organ, and delivery of the desired molecule can be via diffusion, timed-release bolus, or continuous administration.

In some embodiments, it can be desirable to use a pharmaceutical composition comprising a neutralizing PCSK9 variant, with or without at least one additional therapeutic agent, in an ex vivo manner. In such instances, cells, tissues and/or organs that have been removed from the patient are exposed to a pharmaceutical composition comprising a neutralizing PCSK9 variant, with or without at least one additional therapeutic agent, after which the cells, tissues and/or organs are subsequently implanted back into the patient.

In some embodiments, a neutralizing PCSK9 variant and/or any additional therapeutic agents can be delivered by implanting certain cells that have been genetically engineered, using methods such as those described herein, to express and secrete the polypeptides. In some embodiments, such cells can be animal or human cells, and can be autologous, heterologous, or xenogeneic. In some embodiments, the cells can be immortalized. In some embodiments, in order to decrease the chance of an immunological response, the cells can be encapsulated to avoid infiltration of surrounding tissues. In some embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Based on the ability of a neutralizing PCSK9 variant to significantly neutralize PCSK9 activity (as demonstrated in the Examples below), these neutralizing PCSK9 variants will have therapeutic effects in treating and preventing symptoms and conditions resulting from PCSK9-mediated activity, such as hypercholesterolemia.

EXAMPLES

The following examples, including the experiments conducted and results achieved, are provided for illustrative purposes only and are not to be construed as limiting the present invention.

Example 1

Demonstration of a Neutralizing PCSK9 Variant Binding to the LDL Receptor-LDLR Competition Assay This example is directed to the ability of a neutralizing PCSK9 variant to compete with full length PCSK9 for binding to LDLR.

Clear, 96 well plates (Nunc) were coated overnight with 2 micrograms/ml of goat anti-LDL receptor antibody (R&D Systems) diluted in buffer A (100 mM sodium cacodylate, pH 7.4). Plates were washed thoroughly with buffer A and then blocked for 2 hours with buffer B (1% milk in buffer A). After washing, plates were incubated for 1.5 hours with 2.0 ug/ml of LDL receptor (R&D Systems) diluted in buffer C (buffer B supplemented with 10 mM CaCl2). Concurrent with this incubation, 100 ng/ml of biotinylated wild-type human PCSK9 (hPCSK9), diluted in buffer C, was incubated with various concentrations of non-biotinylated competitor proteins (e.g. 31-447 of PCSK9 (SEQ ID NO: 3), full length PCSK9, and the V-domain of PCSK9, residues 450-692) also diluted in buffer C, or buffer C alone (control). The LDL receptor containing plates were washed. The biotinylated PCSK9/competitor protein mixture was transferred to the plates and incubated for 1 hour at room temperature. Binding of the biotinylated PCSK9 to the LDL receptor was detected by incubation with streptavidin-HRP (Biosource) at 500 ng/ml in buffer C followed by TMB substrate (KPL). The absorbance at 650 nm was measured.

The results are presented in FIG. 2. Both the neutralizing PCSK9 variant (amino acids 31-447 of SEQ ID NO: 3), and the full length PCSK9 (fl PCSK9), competed against biotin-labeled full length PCSK9 for binding to the immobilized LDLR. The V-domain protein did not. This data demonstrates that no more than amino acids 31-447 (of SEQ ID NO: 3) are required for binding to the LDLR.

Example 2

Effect of a Neutralizing PCSK9 Variant on Cell LDL Uptake

The example is directed to the ability of one neutralizing PCSK9 variant to impact LDL uptake. HepG2 cells were seeded in 96-well plates (Costar) at a concentration of $5 \times 10^5$ cells per well in DMEM medium (Mediatech, Inc) supplemented with 10% fetal bovine serum (FBS) and incubated overnight at 37° C. (5% CO2). The next day, cells were washed twice with PBS. A serial 1:2 dilution of wild-type PCSK9 or the neutralizing PCSK9 variant (31-447 of SEQ ID NO: 3) was made, ranging from 1.6 ug/ml to 50 ug/ml, and was added to cells. Following the addition of 6 ug/ml of BODIPY-LDL (Invitrogen) and incubation for 3 hours at 37° C. (5% CO2), the cells were washed thoroughly with PBS. Lastly, the cellular associated fluorescence signal was detected by Safire (TECAN) at 480~520 nm (excitation) and 520~600 nm (emission).

The results are presented in FIGS. 3A and 3B which represent two separate experiments of identical design performed on different dates. As can be observed in the figures, full length PCSK9 (having a H8 histidine purification tag) blocked the uptake of labeled LDL in to the cultured cells as evidenced by the decrease in fluorescence from the cells with increasing PCSK9 levels added to the culture medium. In contrast, the neutralizing PCSK9 variant allows for the cells to take up LDL.

Example 3

Western Blot Analysis of the Cellular Effects of a Neutralizing PCSK9 Variant This example is directed to the cellular effects of the presence of a neutralizing PCSK9 variant.

HepG2 cells in 6 well plates were grown to confluency at 37° C. in DMEM medium with 10% fetal bovine serum (FBS). Some cells were pretreated for 30 minutes with 100 uM chloroquine to inhibit acidification of endosomes. Cells were then treated with either vehicle (PBS, less than 50 ul), full length PCSK9 (50 ug/ml, 0.65 uM), or neutralizing PCSK9 variant (31-447 of SEQ ID NO: 3) (30 micrograms/ml, 0.65 uM) in 750 ul of DMEM with 1% FBS for 4 hours at 37° C. Cells were washed three times with PBS and whole cell lysate was prepared using lysis buffer (125 mM Tris, 2 mM CaCl2, 1% triton X-100, pH 8.5). Fifty ug of cell supernatant protein was resolved by SDS PAGE and LDLR levels determined using rabbit anti-human LDLR polyclonal antibody (RDI-PRO61099, Fitzgerald Industries International Inc.). Recombinant PCSK9 associated with the cells was detected by anti-human PCSK9 monoclonal antibody that detects the ~14 kDa prodomain of PCSK9. HRP-conjugated secondary antibodies (Santa Cruz Biotechnology Inc.) and ECL (GE Healthcare) were used for detecting signal. (Veh=vehicle (PBS), FL=full length, PC9=PCSK9).

The results are shown in FIG. 4. As can be seen in the figure, the neutralizing PCSK9 variant (31-447 of SEQ ID NO: 3) associated with cells but did not cause degradation of LDLR, unlike full length PCSK9.

As will be appreciated by one of skill in the art, the data from the above Examples indicate that while a neutralizing PCSK9 variant (e.g., 31-447 of SEQ ID NO: 3) can bind to the LDLR it does not prevent LDL binding and LDL uptake by cells and does not cause LDLR degradation. In addition, the neutralizing PCSK9 variant (31-447 of SEQ ID NO: 3) allows LDLR recycling, preserving the normal function of the LDLR.

Given the present results, it is apparent that neutralizing PCSK9 variants can bind to the LDLR at the cell surface preventing the interaction of full length (wild-type) PCSK9 with the LDLR. Because the neutralizing PCSK9 variant preserves normal LDLR function it acts as a therapeutic protecting the LDLR from the effects of endogenous full length PCSK9.

Example 4

Uses of a Neutralizing PCSK9 Variant for the Treatment of Cholesterol Related Disorders A human patient exhibiting a Cholesterol Related Disorder (in which a reduction in cholesterol (such as serum cholesterol) can be beneficial) is administered a therapeutically effective amount of a neutralizing PCSK9 variant. At periodic times during the treatment, the patient is monitored to determine whether a symptom of the disorder has subsided. Following treatment, it is found that patients undergoing treatment with the neutralizing PCSK9 variant have reduced serum cholesterol levels, in comparison to patients that are not treated.

Example 5

Uses of a Neutralizing PCSK9 Variant for the Treatment of Hypercholesterolemia

A human patient exhibiting symptoms of hypercholesterolemia is administered a therapeutically effective amount of a neutralizing PCSK9 variant. At periodic times during the treatment, the human patient is monitored to determine whether the serum cholesterol level (either as total cholesterol or more specifically LDL cholesterol) has declined. Following treatment, it is found that the patient receiving the treatment with a neutralizing PCSK9 variant has reduced serum cholesterol levels in comparison to arthritis patients not receiving the treatment.

Example 6

Uses of a Neutralizing PCSK9 Variant for the Prevention of Coronary Heart Disease and/or Recurrent Cardiovascular Events A human patient at risk of developing coronary heart disease is identified. The patient is administered a therapeutically effective amount of a neutralizing PCSK9 variant, either alone, concurrently or sequentially with a statin, e.g., simvastatin. At periodic times during the treatment, the human patient is monitored to determine whether the patient's total serum cholesterol level changes. Throughout the preventative treatment, it is found that the patient receiving the treatment with the neutralizing PCSK9 variant has reduced serum cholesterol thereby reducing their risk to coronary heart diseases or recurrent cardiovascular events in comparison to patients not receiving the treatment.

Example 7

Use of a Neutralizing PCSK9 Variant for the Prevention of Hypercholesterolemia

A human patient exhibiting a risk of developing hypercholesterolemia is identified via family history analysis and/or lifestyle, and/or current cholesterol levels. The subject is regularly administered (e.g., one time weekly) a therapeutically effective amount of a neutralizing PCSK9 variant. At periodic times during the treatment, the patient is monitored to determine whether serum cholesterol levels have decreased. Following treatment, it is found that subjects undergoing preventative treatment with a neutralizing PCSK9 variant have lowered serum cholesterol levels, in comparison to subjects that are not treated.

Example 8

Mouse Model for PCSK9

The present example describes how to generate a mouse model for testing various neutralizing PCSK9 variants. To generate mice which over-expressed human PCSK9, three week old WT C57Bl/6 mice were injected via tail vein administration with various concentrations of adenoassociated virus (AAV), recombinantly modified to express human PCSK9, to determine the correct titer which would provide a measurable increase of LDL-cholesterol in the mice. Using this particular virus which expressed human PCSK9, it was determined that $4.5 \times 10^{12}$ pfu of virus would result in an LDL-cholesterol level of approximately 40 mg/dL in circulating blood (normal levels of LDL in a WT mice are approximately 10 mg/dL). The human PCSK9 levels in these animals were found to be approximately 13 ug/mL. A colony of mice was generated using this injection criteria.

One week after injection, mice were assessed for LDL-cholesterol levels.

Example 9

The mice from Example 8 can be used to test various neutralizing PCSK9 variants to determine how effective they are and which variants work in vivo.

A neutralizing PCSK9 variant can be administered, via tail vein injection, in a single bolus injection, or by AAV induced over-expression Subgroups of animals (n=6-7) can then be euthanized at 24 and 48 hours after neutralizing PCSK9 variant administration. LDL levels can then be examined and optionally compared with various controls (e.g., wild-type PCSK9, a water or unrelated protein injection, and the pro/cat domain). Completive PCSK9 variants that result in mice with lower serum LDL levels will be variants that can be effective in lowering serum LDL levels.

Example 10

The LDLR EGFa Domain Binds to the Catalytic Domain of PCSK9

The present example presents the solved crystal structure of PCSK9 Pro/Cat (31-454) bound to the LDLR EGFa domain (293-334) at 2.9 Å resolution (the conditions for which are described in the below Examples).

A representation of the structure of PCSK9 bound to EGFa is shown in FIG. 5. The crystal structure (and its depiction in FIG. 5) reveals that the EGFa domain of LDLR binds to the catalytic domain of PCSK9. In addition, the interaction of PCSK9 and EGFa appears to occur across a surface of PCSK9 that is between residues D374 and S153 in the structure depicted in FIG. 5.

Specific core PCSK9 amino acid residues of the interaction interface with the LDLR EGFa domain were defined as PCSK9 residues that are within 5 Å of the EGFa domain. The core residues are as follows: S153, I154, P155, R194, D238, A239, I369, S372, D374, C375, T377, C378, F379, V380, and S381.

Boundary PCSK9 amino acid residues of the interaction interface with the LDLR EGFa domain were defined as PCSK9 residues that are 5-8 Å from the EGFa domain. The boundary residues are as follows: W156, <u>N157</u>, L158, E159, H193, E195, <u>H229</u>, R237, G240, K243, D367, I368, <u>G370</u>, A371, S373, S376, and Q382. Residues that are underlined are nearly or completely buried within PCSK9.

As will be appreciated by one of skill in the art, the results from this example demonstrate where PCSK9 and EGFa interact. Thus, neutralizing PCSK9 variants that interact with or block any of these residues can be useful to inhibit the interaction between native PCSK9 and the EGFa domain of LDLR (and/or LDLR generally). In some embodiments, neutralizing PCSK9 variants that, when bound to PCSK9, interact with or block any of the above residues or are within 15-8, 8, 8-5, or 5 angstroms of the above residues are contemplated to provide useful inhibition of PCSK9 binding to LDLR.

Example 11

Structural Interaction of LDLR and PCSK9

A model of full length PCSK9 protein bound to a full length representation of the LDLR was made using the PCSK9 Pro/Cat 31-454/EGFa complex structure. The structure of full length PCSK9 (Piper, D. E. et al. The crystal structure of PCSK9: a regulator of plasma LDL-cholesterol. *Structure* 15, 545-52 (2007)) was overlaid onto the PCSK9 Pro/Cat 31-454 from the complex and the structure of the LDLR in its low pH conformation (Rudenko, G. et al. Structure of the LDL receptor extracellular domain at endosomal pH. *Science* 298, 2353-8 (2002)) was overlaid onto the EGFa domain from the complex. Depictions of the model are shown in FIGS. 6 and 7. The EGFa domain from the PCSK9 Pro/Cat 31-454/EGFa complex is enclosed within the box. The figures show regions of the LDLR outside of the immediate EGFa binding domain that lie in close proximity to PCSK9.

Example 12

Expression and Purification of Protein Samples

The present example describes some methods by which the various embodiments of the PCSK9 proteins/variants were made and purified (including the LDLR EGFa domain). PCSK9 proteins/variants (e.g., PSCK9 31-692 N533A, PCSK9 449TEV and PCSK9 Pro/Cat 31-454) were expressed in baculovirus infected Hi-5 insect cells with an N-terminal honeybee melittin signal peptide followed by a $His_6$ tag. The PCSK9 proteins were purified by nickel affinity chromatography, ion exchange chromatography and size exclusion chromatography. The melittin-$His_6$ tag was removed during purification by cleavage with TEV protease. The construct PCSK9 449TEV was used to generate PCSK9 Pro/Cat (31-449 and V domain (450-692) samples. This construct had a TEV protease cleavage site inserted between PCSK9 residues 449 and 450.

The LDLR EGFa domain (293-334) was expressed as a GST fusion protein in *E. coli*. The EGFa domain was purified by ion exchange chromatography, glutathione sepharose affinity chromatography and size exclusion chromatography. The GST protein was removed during the purification by cleavage with PreScission protease.

Example 13

Complex Formation and Crystallization

The present example describes how complexes and crystals used in the above structure examination Examples were made.

The PCSK9 31-454/EGFa complex was made by mixing a 1.2 molar excess of EGFa domain with PCSK9 31-454. The PCSK9 31-454/EGFa domain complex crystallized in 0.2 M potassium formate, 20% PEG 3350.

Example 14

Data Collection and Structure Determination

The present example describes how the datasets were collected and the structures determined for the above structure examination Examples.

The PCSK9 31-454/EGFa dataset was collected at the Berkeley Advanced Light Source beamline 5.0.2. All datasets were processed with denzo/scalepack or HKL2000 (Otwinowski, Z., Borek, D., Majewski, W. & Minor, W. Multiparametric scaling of diffraction intensities. *Acta Crystallogr A* 59, 228-34 (2003)).

PCSK9/EGFa domain crystals grew in the space group $P6_522$ with unit cell dimensions a=b=70.6, c=321.8 Å and diffract to 2.9 Å resolution. The PCSK9/EGFa domain structure was solved by molecular replacement with the program MOLREP using the PCSK9 Pro/Cat as the starting search model. Analysis of the electron density maps showed clear electron density for the EGFa domain. The LDLR EGFa domain was fit by hand and the model was improved with multiple rounds of model building with Quanta and refinement with cnx.

Core interaction interface amino acids were determined as being all amino acid residues with at least one atom less than or equal to 5 Å from the PCSK9 partner protein. 5 Å was chosen as the core region cutoff distance to allow for atoms within a van der Waals radius plus a possible water-mediated hydrogen bond. Boundary interaction interface amino acids were determined as all amino acid residues with at least one atom less than or equal to 8 Å from the PCSK9 partner protein but not included in the core interaction list. Less than or equal to 8 Å was chosen as the boundary region cutoff distance to allow for the length of an extended arginine amino acid. Amino acids that met these distance criteria were calculated with the program PyMOL. (DeLano, W. L. The PyMOL Molecular Graphics System. (Palo Alto, 2002)).

The coordinates for the crystal structures discussed in the above Examples are presented in Table 35.2 of U.S. Prov. Pat. App. No. 61/010,630, filed Jan. 9, 2008, the entirety of which is incorporated by reference. Neutralizing PCSK9 variants that interact with the relevant areas or residues of the structure of PCSK9 (including those areas or residues within 15, 15-8, 8, 8-5, 5, or fewer angstroms from where EGFa interacts with PCSK9) depicted in the figures and/or their corresponding positions on the structures from the coordinates are also contemplated.

Example 15

Additional Neutralizing PCSK9 Variants

This example describes the ability of the D374Y point mutation in a neutralizing PCSK9 variant (amino acids 31-447 of SEQ ID NO: 3) to alter cell LDL uptake (FIG. 8) and compete with full length PCSK9 for binding to the LDLR (FIG. 9).

The protocol followed was generally similar to that outlined above regarding LDL uptake in the presence of the neutralizing PCSK9 variant (amino acids 31-447 of SEQ ID NO: 3), except that full length D374Y PCSK9, a neutralizing PCSK9 variant (amino acids 31-447 of SEQ ID NO: 3) having the D374Y point mutation, and a full length wild-type hPCSK9 were used. The results are shown in FIG. 8.

In addition to the above experiment, LDLR was also captured in an ELISA plate via an LDLR antibody (2 ug/ml). Following this, biotin-WT PCSK9 (100 ng/ml) and various concentrations of unbiotinylated full length D374Y PCSK9, V domain (V domain), and D374Y Pro/Cat (31-447) were added to the plate. Bound biotin-PCSK9 was detected by streptavidin-HRP. The results are presented in FIG. 9 and demonstrate the ability of the D374Y Pro/Cat domain and the D374Y full length PCSK9 to compete with the full length WT PCSK9 for binding to the LDLR.

As can be seen in the results displayed in FIGS. 8 and 9, neutralizing PCSK9 variants will also work to increase the amount of LDL uptake with respect to uptake that occurs in the presence of other forms of PCSK9.

Incorporation by Reference

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

Equivalents

The foregoing written specification is considered to be sufficient to enable one skilled in the art to practice the invention. The foregoing description and examples detail certain embodiments of the invention. It will be appreciated, however, that no matter how detailed the foregoing may appear in text, the invention may be practiced in many ways.

What is claimed is:

1. An isolated neutralizing PCSK9 variant comprising:
   a Pro/Cat domain that binds to low density lipoprotein receptor (LDLR) wherein the Pro/Cat domain consists of an amino acid sequence starting at position 31 or 61 of SEQ ID NO:3 and ending at position 374, 381, 382, 447, 448, 449, 450, 451, 452, or 453 of SEQ ID NO: 3; and
   an inactive V domain, wherein the inactive V domain does not result in the degradation of LDLR, and wherein the inactive V-domain lacks amino acids 454 to 692 of SEQ ID NO:3.

2. The neutralizing PCSK9 variant of claim 1, wherein the Pro/Cat domain consists of amino acids 31 to 374 of SEQ ID NO: 3.

3. The neutralizing PCSK9 variant of claim 1, wherein the Pro/Cat domain consists of amino acids 61 to 447 of SEQ ID NO: 3.

4. The neutralizing PCSK9 variant of claim 1, wherein the Pro/Cat domain consists of amino acids 31 to 449 of SEQ ID NO: 3.

5. A neutralizing PCSK9 variant of claim 1, wherein the Pro/Cat domain consists of amino acids 61 to 374 of SEQ ID NO:3.

6. A pharmaceutical composition comprising at least one neutralizing PCSK9 variant according to any one of claims 1, 2-4 and 5, and a pharmaceutically acceptable excipient.

7. The neutralizing PCSK9 variant of claims 1, 2-4 or 5, for use as a medicament.

8. The neutralizing PCSK9 variant of claims 1, 2-4, or 5, for use in treating hypercholesterolemia.

9. A pharmaceutical composition comprising at least one neutralizing PCSK9 variant according to any one of claims 1, 2-4, and 5, wherein the neutralizing PCSK9 variant is present in an amount effective for the treatment of a cholesterol related disorder.

10. The pharmaceutical composition of claim 9, wherein the effective amount comprises an amount effective for lowering the level of LDL in a human.

11. The pharmaceutical composition of claim 9, wherein the effective amount comprises an amount that elevates the availability of low density lipoprotein receptor (LDLR) protein in a human.

12. The pharmaceutical composition of claim 11, wherein the elevation is at least 5%.

13. The pharmaceutical composition of claim 11, wherein the elevation is at least 20%.

14. The pharmaceutical composition of claim 11, wherein the elevation is at least 50%.

15. The pharmaceutical composition of claim 11, wherein the elevation is at least 100%.

16. The pharmaceutical composition of claim 11, wherein the elevation is at least 300%.

17. The pharmaceutical composition of claim 11, wherein the human is a 100 kg male.

18. The pharmaceutical composition of claim 11, wherein the human is a 50 kg male.

19. A pharmaceutical composition comprising:
an isolated protein that binds to a low density lipoprotein receptor (LDLR) wherein the isolated protein consists of an amino acid sequence starting at position 31 or 61 of SEQ ID NO:3 and ending at position 374, 381, 382, 447, 448, 449, 450, 451, 452, or 453 of SEQ ID NO: 3, wherein the isolated protein is neutralizing to PCSK9 activity, and wherein the isolated protein is present in an amount effective for blocking PCSK9 activity at a level sufficient to elevate availability of LDLR protein by at least 5%.

* * * * *

UNITED STATES PATENT AND TRADEMARK OFFICE
CERTIFICATE OF CORRECTION

PATENT NO. : 9,994,923 B2
APPLICATION NO. : 12/989404
DATED : June 12, 2018
INVENTOR(S) : Mark Simon Jackson et al.

It is certified that error appears in the above-identified patent and that said Letters Patent is hereby corrected as shown below:

On the Title Page

In Column 2, item (56), Other Publications, Line 15, delete "degredation" and insert --degradation--.

In Column 2, item (56), Other Publications, Line 20, delete "porprotein" and insert --proprotein--.

In Column 2, item (56), Other Publications, Line 30, delete "(37:" and insert --(37):--.

In the Specification

In Column 3, Line 62, delete ""Q")" and insert --"Q").--.

In Column 6, Line 65, delete "NARC1" and insert --NARC 1--.

In Column 7, Line 12, delete "al," and insert --al.,--.

In Column 7, Line 44, delete "al," and insert --al.,--.

In Column 7, Line 45, delete "apoliprotein" and insert --apolipoprotein--.

In Column 7, Line 47, delete "al," and insert --al.,--.

In Column 7, Line 52, delete "al," and insert --al.,--.

In Column 7, Line 55, delete "PCSK9s" and insert --PCSK9's--.

In Column 8, Line 10 (Approx.), delete "phoshoraniladate" and insert --phosphoroaniladate--.

In Column 15, Line 3, delete "percent" and insert --percent)--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,994,923 B2

In Column 15, Line 66, delete "non specific" and insert --nonspecific--.

In Column 16, Line 2, after "attached" insert --figures (--.

In Column 16, Line 32, delete "percent" and insert --percent)--.

In Column 16, Line 51, delete "percent" and insert --percent)--.

In Column 22, Line 56, delete "LDLR" and insert --LDLR.--.

In Column 23, Line 19, delete "R499c," and insert --R499C,--.

In Column 23, Line 21, delete "al," and insert --al.,--.

In Column 24, Line 29, after "attached" insert --figures (--.

In Column 26, Line 41, delete "tag," and insert --tag),--.

In Column 26, Line 48, delete "(2006);" and insert --(2006));--.

In Column 26, Line 52, delete "Assoication" and insert --Association--.

In Column 26, Line 64, delete "al," and insert --al.,--.

In Column 26, Line 65, delete "Narc1" and insert --Narc 1--.

In Column 27, Line 20, delete "1 PCSK9)" and insert --1 (=PCSK9)--.

In Column 27, Line 26, delete "abovevariants" and insert --above variants--.

In Column 27, Line 42, delete "covatlently" and insert --covalently--.

In Column 29, Line 33, delete "half life" and insert --half-life--.

In Column 30, Line 5, delete "$NR_3$, $R_4$" and insert --$NR_3$ $R_4$--.

In Column 30, Line 36 (approx.), delete "N-acetylimidizole" and insert --N-acetylimidazole--.

In Column 30, Line 42 (approx.), delete "ethyl)" and insert --ethyl))--.

In Column 32, Line 14, delete "half life" and insert --half-life--.

In Column 32, Line 19, delete "Fe" and insert --Fc--.

In Column 32, Line 34, delete "al," and insert --al.,--.

CERTIFICATE OF CORRECTION (continued)
U.S. Pat. No. 9,994,923 B2

In Column 33, Line 16, delete "domain)." and insert --domain)).--.

In Column 34, Lines 27-28, delete "physiocochemical" and insert --physicochemical--.

In Column 38, Line 66, delete "chromotography" and insert --chromatography--.

In Column 40, Line 3, delete "Alzheimers" and insert --Alzheimer's--.

In Column 40, Line 14, delete "apoplipoprotein" and insert --apolipoprotein--.

In Column 40, Line 56, delete "Nutirtional" and insert --Nutritional--.

In Column 40, Line 57, delete "Regulatiory" and insert --Regulatory--.

In Column 42, Line 8, delete "(fenofibrate)," and insert --(fenofibrate)),--.

In Column 42, Line 13, delete "NIASPAN)," and insert --NIASPAN)),--.

In Column 42, Line 14, delete "ZETIA)" and insert --ZETIA))--.

In Column 42, Line 28, delete "anti-psycotic" and insert --anti-psychotic--.

In Column 43, Line 54, after "jnk," insert --IKK,--.

In Column 44, Line 34, delete "tyloxapal" and insert --tyloxapol--.

In Column 54, Lines 3-4, delete "adenoassociated" and insert --adeno-associated--.

In Column 55, Line 46, delete "449" and insert --449)--.

In Column 56, Line 65, delete "biotin-WT PCSK9" and insert --biotin-WT_PCSK9--.

In the Claims

In Column 155, Line 61, Claim 1, delete "NO:3" and insert --NO: 3--.

In Column 155, Line 67, Claim 1, delete "NO:3." and insert --NO: 3.--.

In Column 156, Line 67, Claim 5, delete "NO:3." and insert --NO: 3.--.

In Column 158, Line 15 (approx.), Claim 19, delete "NO:3" and insert --NO: 3--.